US012076332B2

(12) United States Patent
Bitan et al.

(10) Patent No.: US 12,076,332 B2
(45) Date of Patent: Sep. 3, 2024

(54) TREATMENT OF LYSOSOMAL STORAGE DISORDERS

(71) Applicants: The Regents of the University of California, Oakland, CA (US); Fondazione Telethon, Rome (IT)

(72) Inventors: Gal Bitan, Encino, CA (US); Alessandro Fraldi, Rome (IT); Irene Sambri, Rome (IT); Antonio Monaco, Rome (IT)

(73) Assignees: The Regents of the University of California, Oakland, CA (US); FONDAZIONE TELETHON ETS, Rome (IT)

( * ) Notice: Subject to any disclaimer, the term of this patent is extended or adjusted under 35 U.S.C. 154(b) by 320 days.

(21) Appl. No.: 17/050,406

(22) PCT Filed: Apr. 25, 2019

(86) PCT No.: PCT/US2019/029222
§ 371 (c)(1),
(2) Date: Oct. 23, 2020

(87) PCT Pub. No.: WO2020/023094
PCT Pub. Date: Jan. 30, 2020

(65) Prior Publication Data

US 2021/0052611 A1 Feb. 25, 2021

Related U.S. Application Data

(60) Provisional application No. 62/663,964, filed on Apr. 27, 2018.

(51) Int. Cl.
*A61K 31/663* (2006.01)
*A61K 31/10* (2006.01)
*A61K 31/19* (2006.01)
*A61K 31/6615* (2006.01)
*A61P 25/00* (2006.01)

(52) U.S. Cl.
CPC ............ *A61K 31/663* (2013.01); *A61K 31/10* (2013.01); *A61K 31/19* (2013.01); *A61K 31/6615* (2013.01); *A61P 25/00* (2018.01)

(58) Field of Classification Search
CPC ........ A61K 31/10; A61K 31/19; A61K 31/66; A61K 31/661; A61K 31/6615; A61K 31/663; A61P 25/00; A61P 25/28; A61P 43/00
See application file for complete search history.

(56) References Cited

U.S. PATENT DOCUMENTS 10,918,657 B2 2/2021 Morgan et al.
2011/0237538 A1 9/2011 De Moor et al.
2012/0108548 A1 5/2012 Bitan et al.
2015/0057320 A1 2/2015 Petrukhin
2015/0202222 A1 7/2015 Morgan et al.
2016/0038448 A1 2/2016 Raleigh et al.
2018/0306813 A1 10/2018 Dobson et al.
2020/0164021 A1 5/2020 Kopke et al.
2021/0069217 A1 3/2021 Bitan et al.
2021/0122771 A1 4/2021 Bitan et al.
2021/0137861 A1 5/2021 Kopke

FOREIGN PATENT DOCUMENTS

EP 3112466 A1 1/2017
WO WO-2006056182 A1 6/2006
WO WO-2010015816 A2 2/2010
WO WO-2010102248 A2 9/2010
WO WO-2010135004 A1 11/2010
WO WO-2020006489 A1 1/2020
WO WO-2020023094 A2 1/2020
WO WO-2020036656 A2 2/2020

OTHER PUBLICATIONS

Ohmi et. al., PNAS, vol. 106(20), pp. 8332-8337, publ. 2009 (Year: 2009).*

Aoyagi-Scharber et. al., Mol. Ther. Methods & Clin. Develop., vol. 6, pp. 43-53, publ. Sep. 2017 (Year: 2017).*

Attar, A. et al., “Disrupting Self-Assembly and Toxicity of Amyloidogenic Protein Oligomers by “Molecular Tweezers”—from the Test Tube to Animal Models”, Current Pharmaceutical Design, 2014, vol. 20, No. 15, pp. 2469-2483.

Attar, A. et al., “Protection of primary neurons and mouse brain from Alzheimer’s pathology by molecular tweezers”, Brain, Dec. 2012, vol. 135, No. 12, pp. 3735-3748.

Biase, D.D. et al., “Amyloid Precursor Protein, Lipofuscin Accumulation and Expression of Autophagy Markers in Aged Bovine Brain”, BMC Veterinary Research, Apr. 13, 2017, vol. 13, No. 102, 9 pages.

Boland, B. et al., “Autophagy Induction and Autophagosome Clearance in Neurons: Relationship to Autophagic Pathology in Alzheimer’s Disease”, Journal of Neuroscience, Jul. 2, 2008, vol. 28, No. 27, pp. 6926-6937.

Boyer, N.P. et al., “Lipofuscin and N-Retinylidene-N-Retinylethanolamine (A2E) Accumulate in Retinal Pigment Epithelium in Absence of Light Exposure: Their Origin is 11-cis-retinal”, Journal of Biological Chemistry, Jun. 22, 2012, vol. 287, No. 26, pp. 22276-22286.

Cai, S. et al., “EGCG Inhibited Lipofuscin Formation Based on Intercepting Amyloidogenic βSheet-Rich Structure Conversion”, PLoS ONE, 2016, vol. 11, No. 3, e0152064, 13 pages.

(Continued)

*Primary Examiner* — Sarah Pihonak

(74) *Attorney, Agent, or Firm* — Foley Hoag LLP; David P. Halstead; Alexander Berne

(57) ABSTRACT

In various embodiments methods are provided for the treatment or prophylaxis of liposomal storage diseases. In certain embodiments the methods involve administering to a subject in need thereof one or more molecular tweezers that inhibit protein aggregation.

12 Claims, 28 Drawing Sheets

(56) References Cited

OTHER PUBLICATIONS

Ciechanover, A. et al., "Degradation of Misfolded Proteins in Neurodegenerative Diseases: Therapeutic Targets and Strategies", Experimental & Molecular Medicine, 2015, vol. 47, No. 3, e147, 16 pages.
Extended European Search Report dated Dec. 20, 2021, in Application No. EP19850534.9.
Extended European Search Report dated Jan. 27, 2022, in Application No. EP19841367.6.
Hohn, A. et al., "Lipofuscin: Formation, Effects and Role of Macroautophagy", Redox Biology, Jan. 19, 2013, vol. 1, No. 1, pp. 140-144.
Iannuzzi, C. et al., "The Effect of Glycosaminoglycans (GAGs) on Amyloid Aggregation and Toxicity", Molecules, Feb. 2015, vol. 20, No. 2, pp. 2510-2528.
International Preliminary Report on Patentability dated Oct. 27, 2020, in PCT Application No. PCT/US2019/029221.
International Preliminary Report on Patentability dated Oct. 27, 2020, in PCT Application No. PCT/US2019/029222.
International Search Report and Written Opinion dated Feb. 14, 2020 in PCT Application No. PCT/US2019/029222.
International Search Report and Written Opinion dated Jan. 30, 2020 in PCT Application No. PCT/US2019/029221.
Klionsky, D.J. et al. "Guidelines for the Use and Interpretation of Assays for Monitoring Autophagy (3rd edition)", Autophagy, 2016, vol. 12, No. 1, pp. 1-222.
Kovács, G. et al., "Involvement of the Endosomal-Lysosomal System Correlates With Regional Pathology in Creutzfeldt-Jakob Disease", Jul. 1, 2007, Journal of Neuropathology and Experimental Neurology, vol. 66, No. 7, pp. 628-636.
Lau, A.A. et al., "Open Field Locomotor Activity and Anxiety-related Behaviors in Mucopolysaccharidosis Type IIIA Mice", Behavioural Brain Research, Aug. 2008, vol. 191, No. 1, pp. 130-136.
Lie, P. et al., "Lysosome Trafficking and Signaling in Health and Neurodegenerative Diseases", Neurobiology of Disease, Feb. 2019, vol. 122, pp. 94-105. [HHS Public Access—Author manuscript—28 pages].
Maday, S. et al., "Autophagosomes Initiate Distally and Mature During Transport Toward the Cell Soma in Primary Neurons", Journal of Cell Biology, Feb. 20, 2012, vol. 196, No. 4, pp. 407-417.
Petrukhin, K., "Pharmacological Inhibition of Lipofuscin Accumulation in the Retina as a Therapeutic Strategy for Dry AMD Treatment", Drug Discovery Today Therapeutic Strategies, 2013, vol. 10, No. 1, pp. e11-e20.
Prabhudesai, S. et al., "A Novel "Molecular Tweezer" Inhibitor of $\alpha$-Synuclein Neurotoxicity in Vitro and in Vivo", Neurotherapeutics, Apr. 2012, vol. 9, No. 2, pp. 464-476.
Pu, J. et al., "Mechanisms and Functions of Lysosome Positioning", Journal of Cell Science, Dec. 1, 2016, vol. 129, No. 23, pp. 4329-4339.
Rahimi, F. et al., "Structure-Function Relationships of Pre-Fibrillar Protein Assemblies in Alzheimer's Disease and Related Disorders", Current Alzheimer Research, Jun. 2008, vol. 5, No. 3, pp. 319-341. [NIH Public Access—Author Manuscript—43 pages].
Ratnayaka, j.A., et al., "Dementia of the eye: The Role of Amyloid Beta in Retinal Degeneration", Eye, 2015, vol. 29, pp. 1013-1026.
Richter, F. et al., "A Molecular Tweezer Ameliorates Motor Deficits in Mice Overexpressing $\alpha$-Synuclein" Neurotherapeutics, Oct. 2017, vol. 14, No. 4, pp. 1107-1119.
Sambri, I. et al., "Lysosomal Dysfunction Disrupts Presynaptic Maintenance and Restoration of Presynaptic Function Prevents Neurodegeneration in Lysosomal Storage Diseases", EMBO Molecular Medicine, Jan. 2017, vol. 9, No. 1, pp. 112-132.
Schrader, T. et al., "Molecular Tweezers for Lysine and Arginine—Powerful Inhibitors of Pathologic Protein Aggregation", Chemical Communications, Oct. 15, 2016, vol. 52, No. 76, pp. 11318-11334.
Serpell, L.C., "Alzheimer's Amyloid Fibrils: Structure and Assembly", Biochimica et Biophysica Acta, Jul. 26, 2000, vol. 1502, No. 1, pp. 16-30.
Settembre, C. et al., "A Block of Autophagy in Lysosomal Storage Disorders", Human Molecular Genetics, Jan. 1, 2008, vol. 17, No. 1, pp. 119-129.
Sinha, S. et al., "Lysine-Specific Molecular Tweezers are Broad-Spectrum Inhibitors of Assembly and Toxicity of Amyloid Proteins", Journal of The American Chemical Society, Oct. 26, 2011, vol. 133, No. 42, pp. 16958-16969, Retrieved from the Internet [URL: https://pubs.acs.org/doi/pdf/10.1021/ja206279b].
Sorrentino, N.C. et al., "A Highly Secreted Sulphamidase Engineered to Cross the Blood-brain Barrier Corrects Brain Lesions of Mice With Mucopolysaccharidoses Type IIIA", EMBO Molecular Medicine, May 2013, vol. 5, No. 5, pp. 675-690.
Terman, A. et al., "Lipofuscin", International Journal of Biochemistry and Cell Biology, Aug. 2004, vol. 36, pp. 1400-1404.
Uchida, K., "Lipofuscin-like Fluorophores Originated From Malondialdehyde", Free Radical Research, Dec. 2006, vol. 40, No. 12, pp. 1335-1338.
U.S. Non-Final office Action dated Jan. 24, 2023 in U.S. Appl. No. 17/050,401.
Whyte, L.S. et al., "Endo-lysosomal and Autophagic Dysfunction: a Driving Factor in Alzheimer's Disease", Journal of Neurochemistry, Mar. 2017, vol. 140, No. 5, pp. 703-717.
Wikipedia, "lipofuscin", Dec. 12, 2017, retrieved on Jan. 2, 2020 https://en.wikipedia.org/w/index.php?title=Lipofuscin&oldid=815019571.
Wilkinson, F.L. et al., "Neuropathology in Mouse Models of Mucopolysaccharidosis Type I, IIIA and IIIB", PloS one, 2012, vol. 7, No. 4, e35787, 18 pages.
Acharya, S., et al., "Molecular Basis for Preventing $\alpha$-Synuclein Aggregation by a Molecular Tweezer", Journal of Biological Chemistry, 2014, vol. 289, pp. 10727-10737.
Attar, A., et al., "Safety and Pharmacological characterization of the Molecular Tweezer CLR01, BMC Pharmacol," Toxicol, 2014, vol. 15, No. 23, DOI:10.1186/2050-6511-15-23.
Attar, A., et al., "Modulators of Amyloid Protein Aggregation and Toxicity: EGCG and CLR01", Translational neuroscience, 2013, vol. 4, pp. 385-409.
Brunk, T., et al., "Lipofuscin: Mechanisms of Age-related Accumulation and Influence on Cell Function," Free Radical Biology & Medicine, 2002, vol. 33(5), pp. 611-619.
Dutt, S. et al., "Linker Effects on Amino Acid and Peptide Recognition by Molecular Tweezers: Recognition by Molecular Tweezers", European Journal of Organic Chemistry, Dec. 1, 2013, vol. 2013, No. 34, pp. 7705-7714.
Dutt, S., "Molecular Tweezers with Additional Binding Sites Against Protein Aggregation", Dissertation, Jan. 1, 2012, pp. 1-227.
European Office Action dated Oct. 11, 2022 for EP Application No. EP19824953.4.
Extended European Search Report dated Feb. 3, 2022 in Application No. EP19824953.4.
Ferreira, N., et al., "Molecular Tweezers Targeting Transthyretin Amyloidosis", Neurotherapeutics, 2014, vol. 11, pp. 450-461.
Fogerson, S.M., et al., "Reducing Synuclein Accumulation After Spinal Cord Injury Improves Neuronalsurvival and Axon Regeneration", Experimental Neurology, 2016, vol. 278, pp. 105-115.
Fokkens, M., et al., "A Molecular Tweezer for Lysine and Arginine", Journal of the American Chemical Society, Oct. 19, 2005, vol. 127, Issue 41, pp. 14415-14421.
Fradinger, E.A., "C-Terminal Peptides Coassemble into A$\beta$42 Oligomers and Protect Neurons Against A$\beta$42-Induced Neurotoxicity", Proceedings of the National Academy of Sciences of the United States of America, 2008, vol. 105, No. 37, pp. 14175-14180.
Heid, C., "Molekulare Pinzetten Zur Proteinoberflachenerkennung", Dissertation, Feb. 1, 2018, pp. 1-371.
Her, C., et al., "Real-Time Enzyme Kinetics by Quantitative NMR Spectroscopy and Determination of the Michaelis-Menten Constant Using the Lambert-W Function", Journal of Chemical Education, 2015, vol. 92, No. 11, pp. 1943-1948.
Herzog, G., et al, "The Lys-Specific Molecular Tweezer, CLR01, Modulates Aggregation of Mutant p53 DNA Binding Domain and Inhibits its Toxicity", Biochemistry, 2015, vol. 54, pp. 3729-3738.
International Preliminary Report on Patentability dated Jan. 7, 2021 in PCT Application No. PCT/US2019/039943.

(56) References Cited

OTHER PUBLICATIONS

International Search Report and Written Opinion dated Aug. 30, 2019 in PCT Application No. PCT/US2019/039943.
JP Office Action dated Apr. 17, 2023 in Application No. JP2020-560381 with English translation.
JP Office Action dated Apr. 17, 2023 in Application No. JP2020-560382 with English translation.
JP Office Action dated Sep. 19, 2023 in Application No. JP2020-560382 with English Translation.
Liu, J.B., et al., "Silver-Mediated Oxidative Trifluoromethylation of Phenols: Direct Synthesis of Aryl Trifluoromethyl Ethers", Angewandte Chemie International Edition, 2015, vol. 54, No. 40, pp. 11839-11842.
Lopes, D.H.J., et al., "Molecular Tweezers Inhibit Isletamyloid Polypeptide Assembly and Toxicity by a New Mechanism", ACS Chemical Biology, 2015, vol. 10, pp. 1555-1569.
Lulla, A., et al., "Neurotoxicity of the Parkinson's Disease-Associated Pesticide Ziram isSynuclein-Dependent in Zebrafish Embryos", Environmental Health Perspectives, 2016, vol. 124, pp. 1766-1775.
Lump, E., et al., "A Molecular Tweezer Antagonizes Seminal Amyloids and HIV Infection," eLife, Aug. 18, 2015, 4:e05397, pp. 1-33.
Malik, R., et al., "Using Moleculartweezers to Remodel Abnormal Protein Self-assembly and Inhibit the Toxicity of Amyloidogenic Proteins", Methods in Molecular Biology, 2018, vol. 1777, pp. 369-386.
Malishev, R., et al., "Toxicity Inhibitors Protect Lipid Membranes from Disruption by Aβ42", ACS Chemical Neuroscience, 2015, vol. 6, pp. 1860-1869.
Rocker, A.E., et al., "The Molecular Tweezer CLR01 Inhibits Ebola and Zika Virus Infection", Antiviral Research, 2018, vol. 152, pp. 26-35.
Sinha, S., et al, "Comparison of Three Amyloidassembly Inhibitors—the Sugar Scyllo-Inositol, the Polyphenol Epigallocatechin Gallate, and the Moleculartweezer CLR01", ACS Chemical Neuroscience, 2012, vol. 3, pp. 451-458.
Talbiersky, P., et al., "Molecular Clip and Tweezer Introduce New Mechanisms of Enzyme Inhibition", Journal of the American Chemical Society, 2008, vol. 130, No. 30, pp. 9824-9828.
U.S. Final office Action dated Oct. 10, 2023 in U.S. Appl. No. 17/050,401.
U.S. Restriction requirement dated Sep. 20, 2023, in U.S. Appl. No. 17/255,963.
Vopel, T., "Inhibition of Huntingtin Aggregation by the Molecular Tweezer CLR01", Journal of the American Chemical Society, 2017, vol. 139, pp. 5640-5643.
Warburton, S., et al., "Examining the Proteins of Functional Retinal Lipofuscin Using Proteomic Analysis as a Guide for Understanding Its Origin," Molecular Vision, 2005, vol. 11, pp. 1122-1134.
Xu, N. et al., "Inhibition of Mutant αB Crystallin-Induced Protein Aggregation by a Molecular Tweezer", Journal of the American Heart Association, Jan. 1, 2017, vol. 6, e006182, pp. 1-13.
Zheng, X., et al., "Amyloid β-protein Assembly: The Effect of Molecular Tweezers CLR01 and CLR03", The Journal of Physical Chemistry B, 2015, vol. 119, pp. 4831-4841.

* cited by examiner

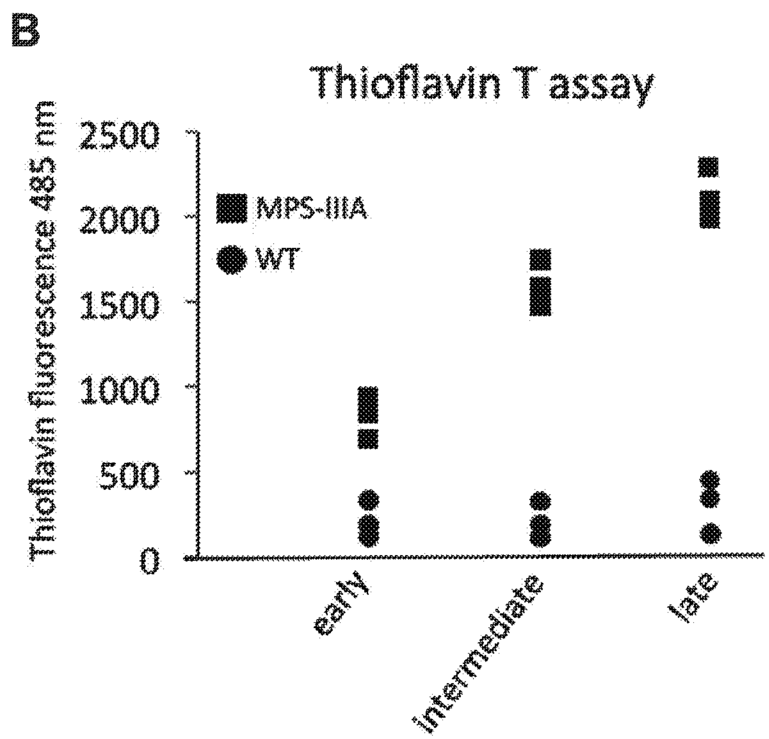
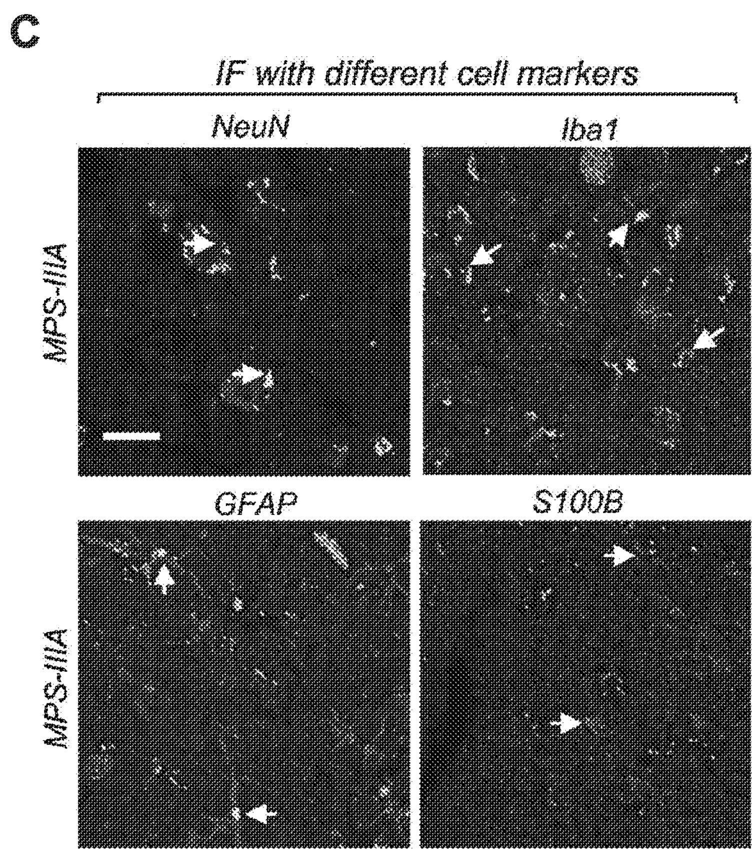
*Fig. 1, cont'd.*

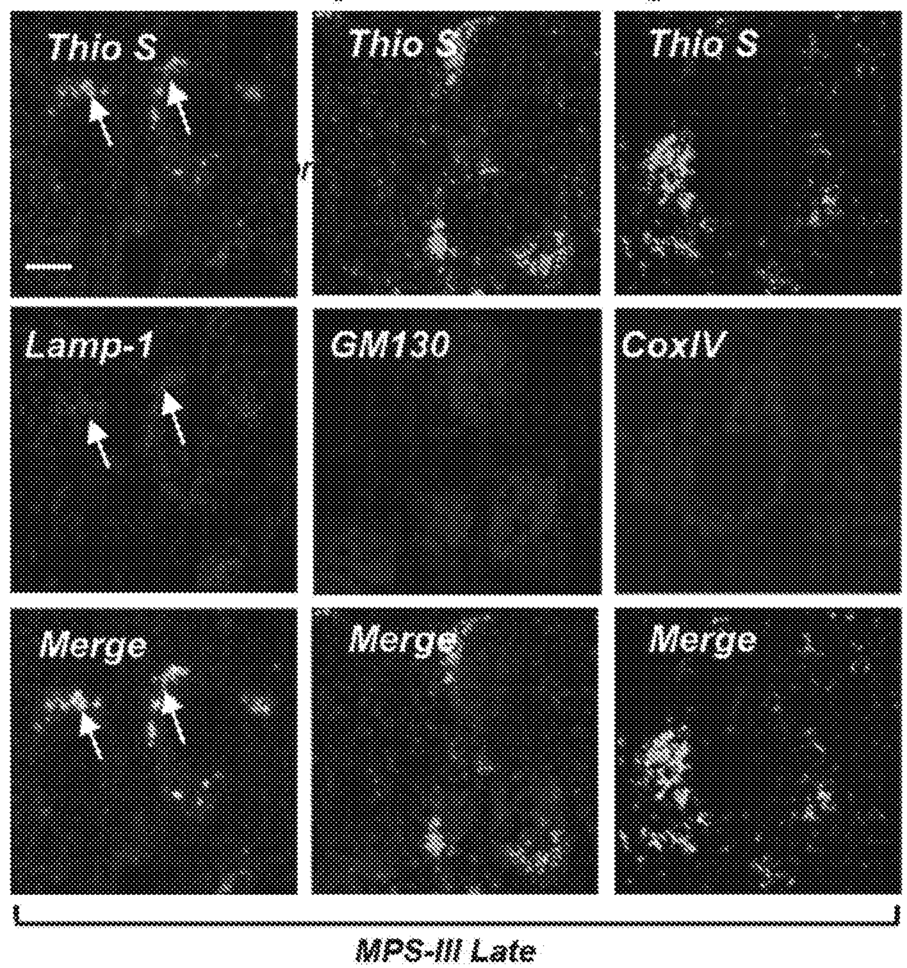
Fig. 1, cont'd.

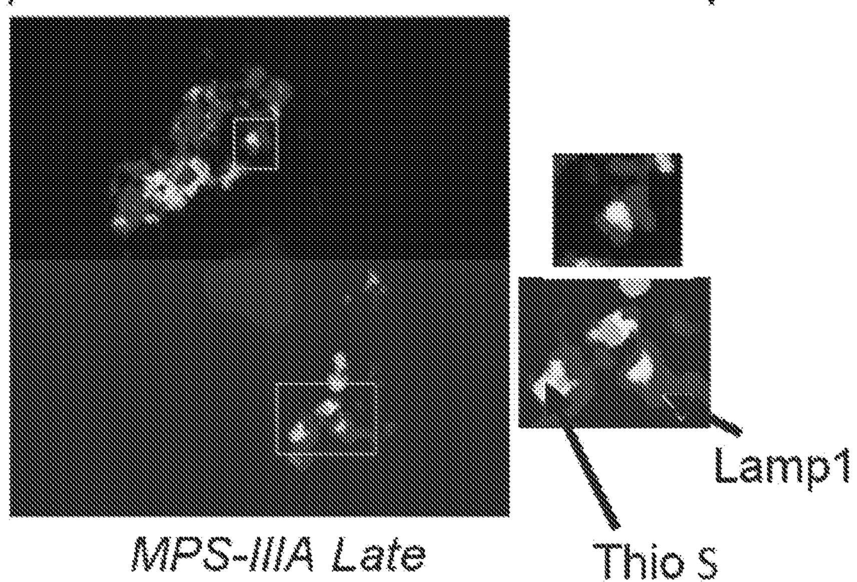
Fig. 1, cont'd.

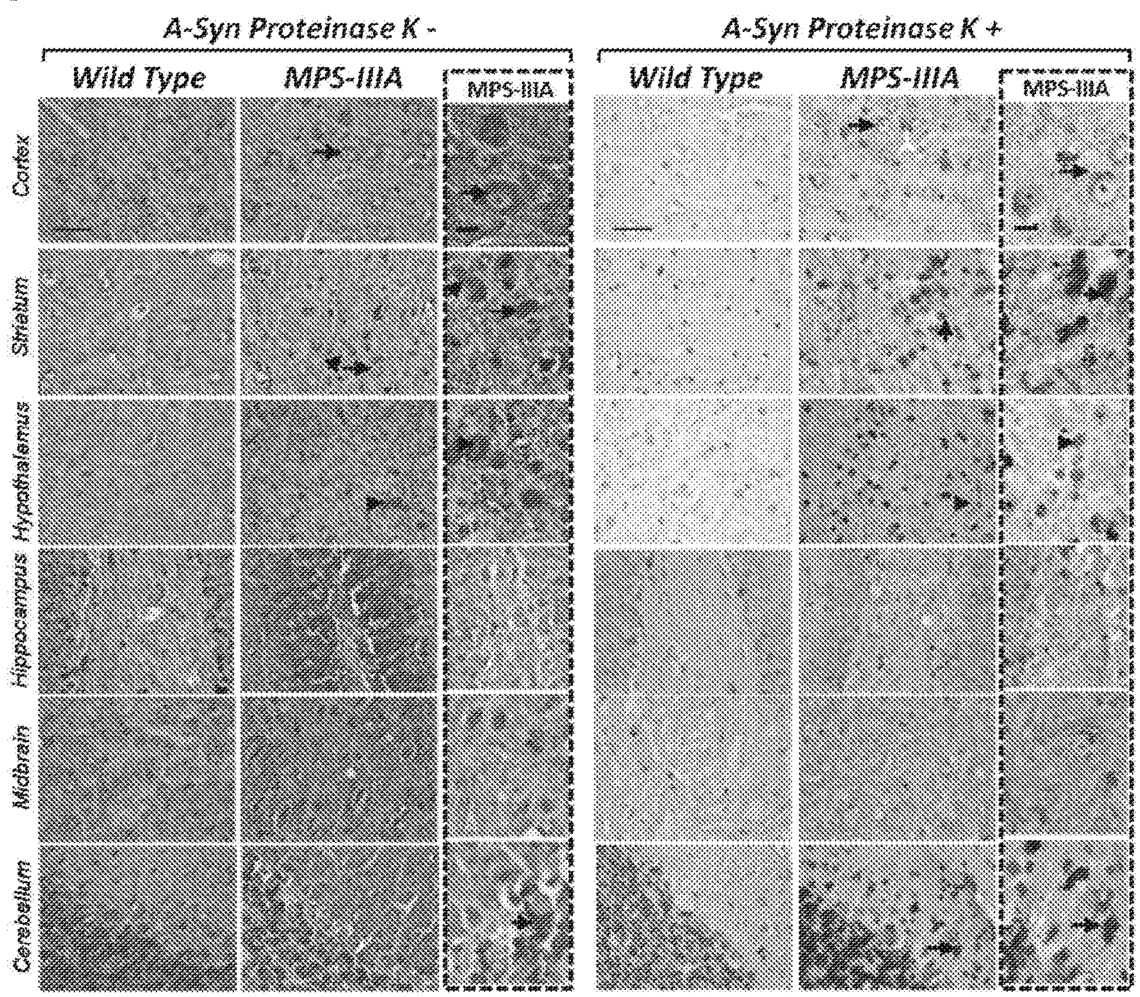
Fig. 1, cont'd.

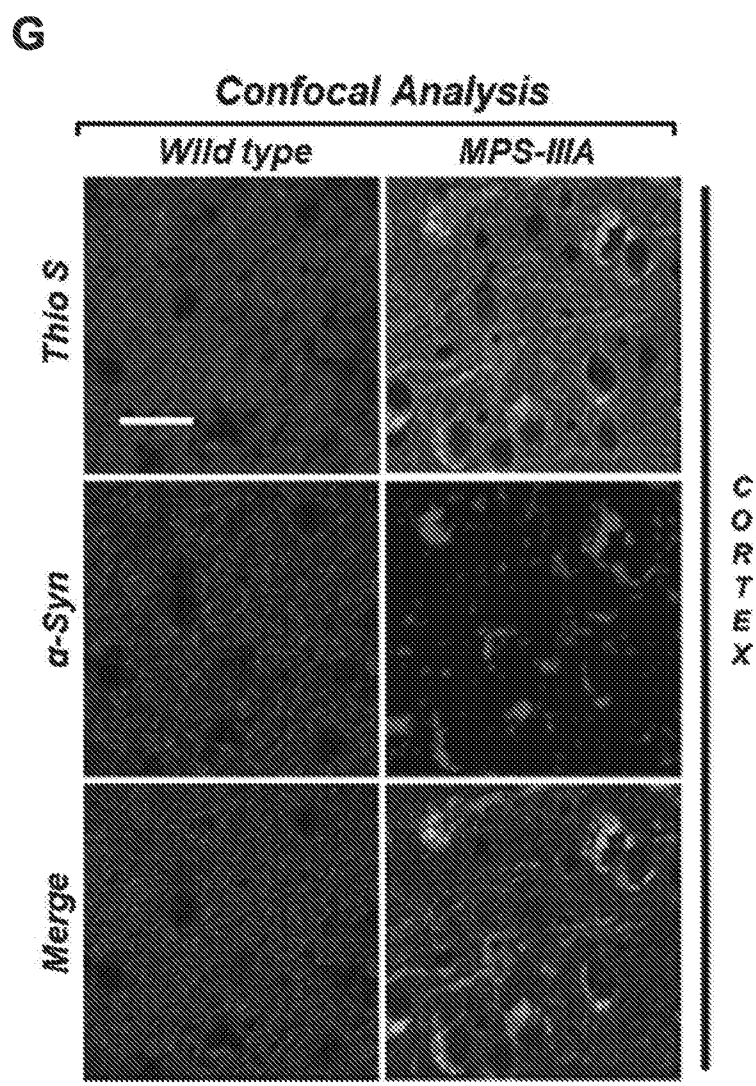
Fig. 1, cont'd.

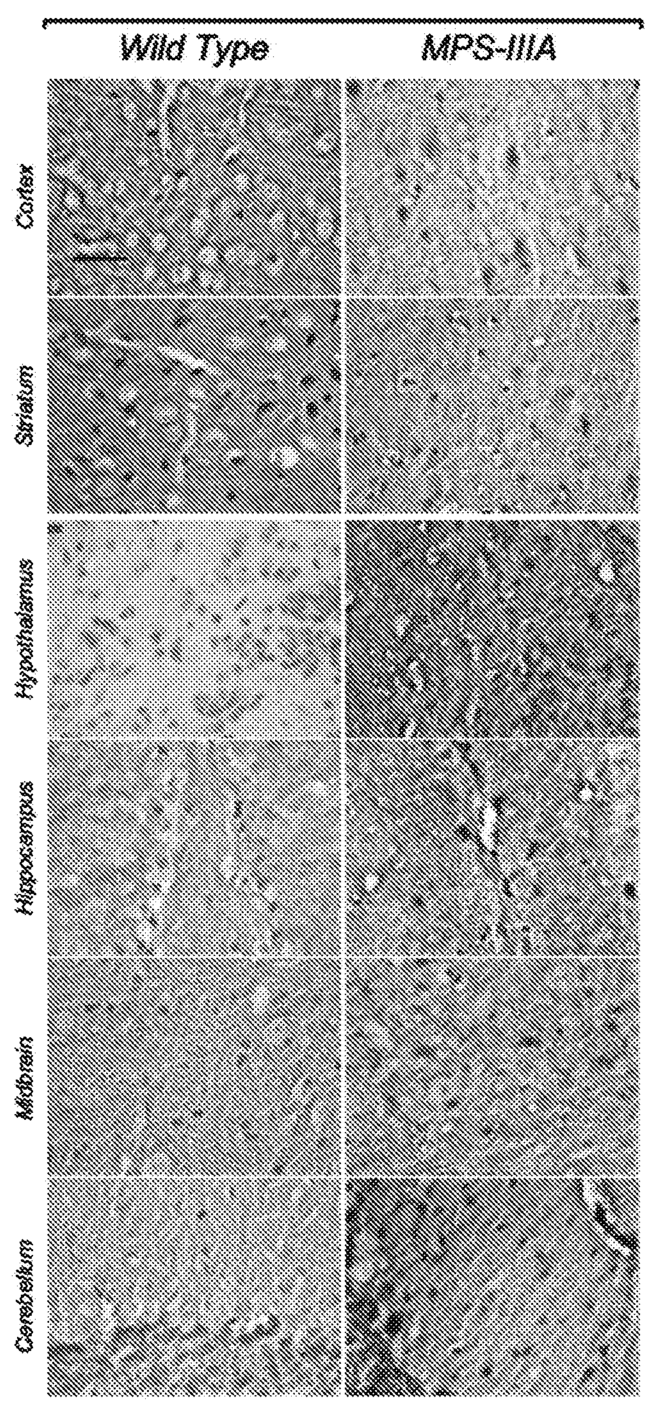
Fig. 2, cont'd.

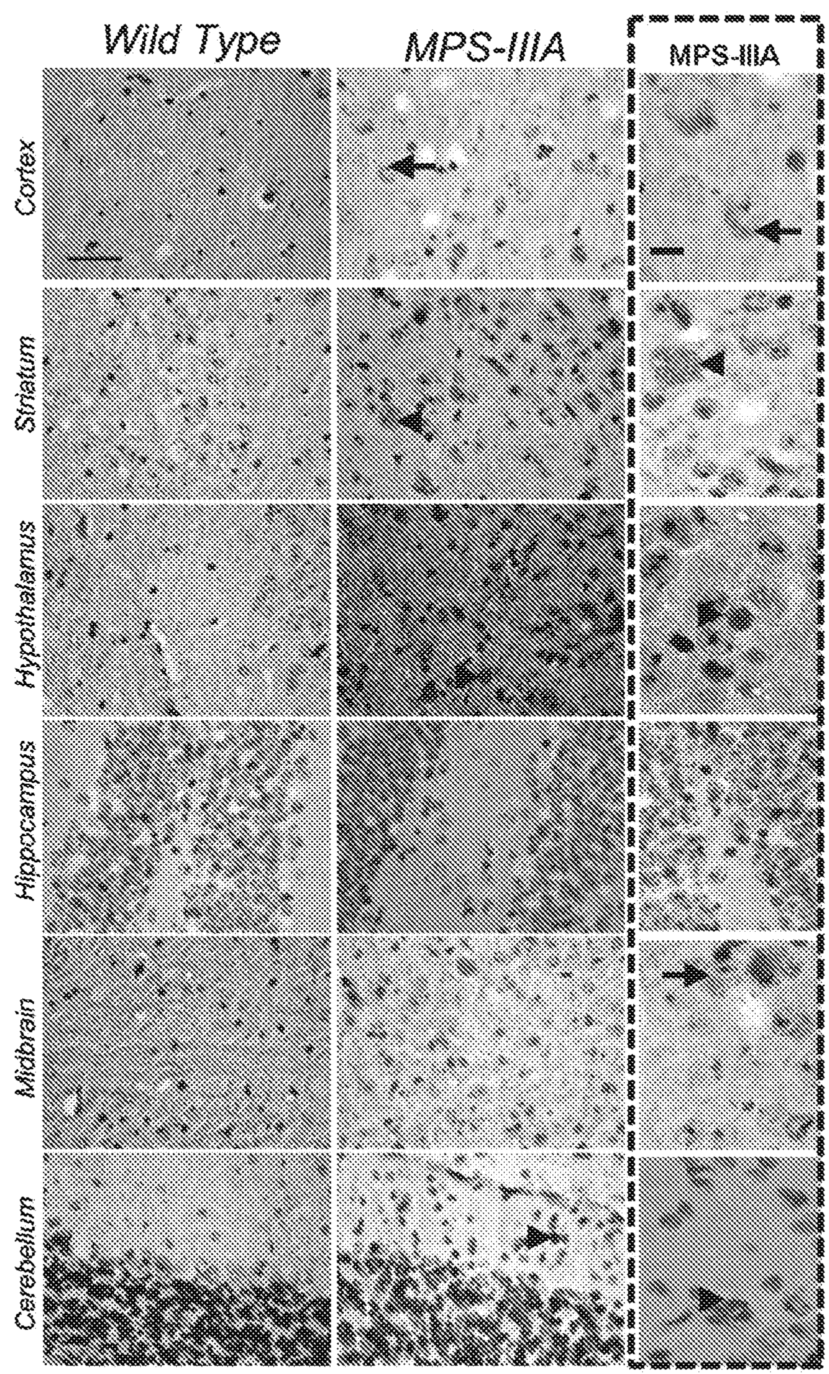
Fig. 2, cont'd

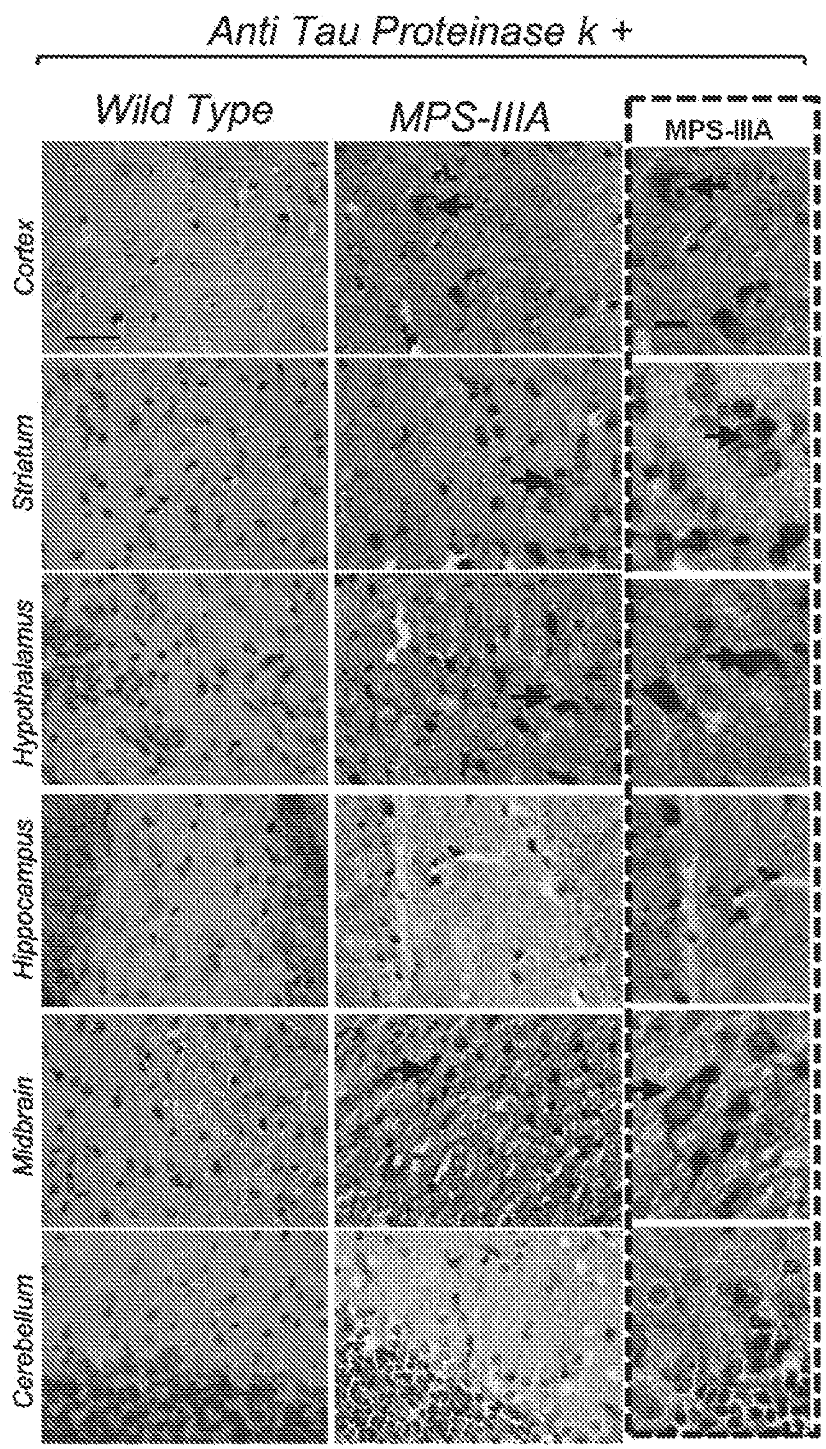
Fig. 2, cont'd.

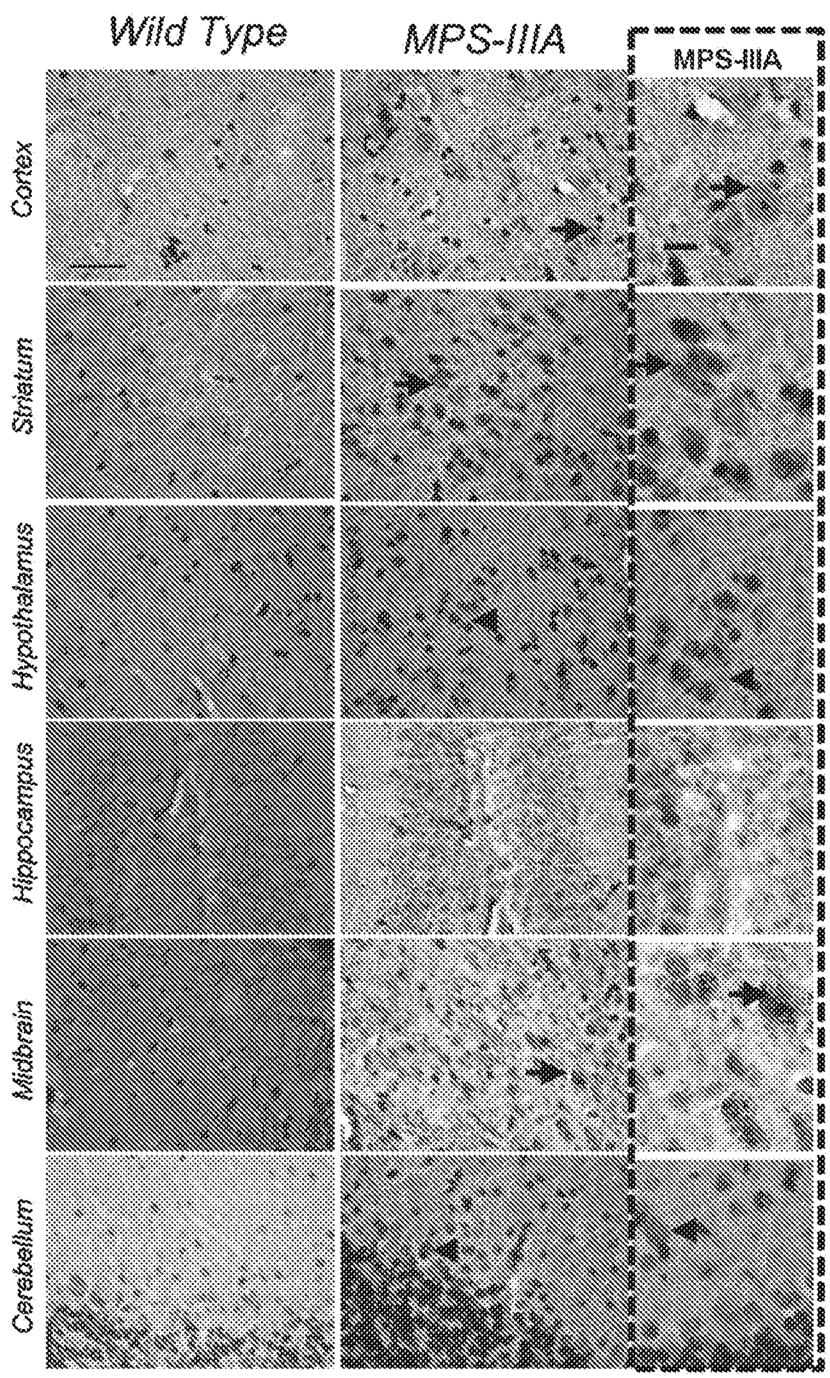
Fig. 2, cont'd.

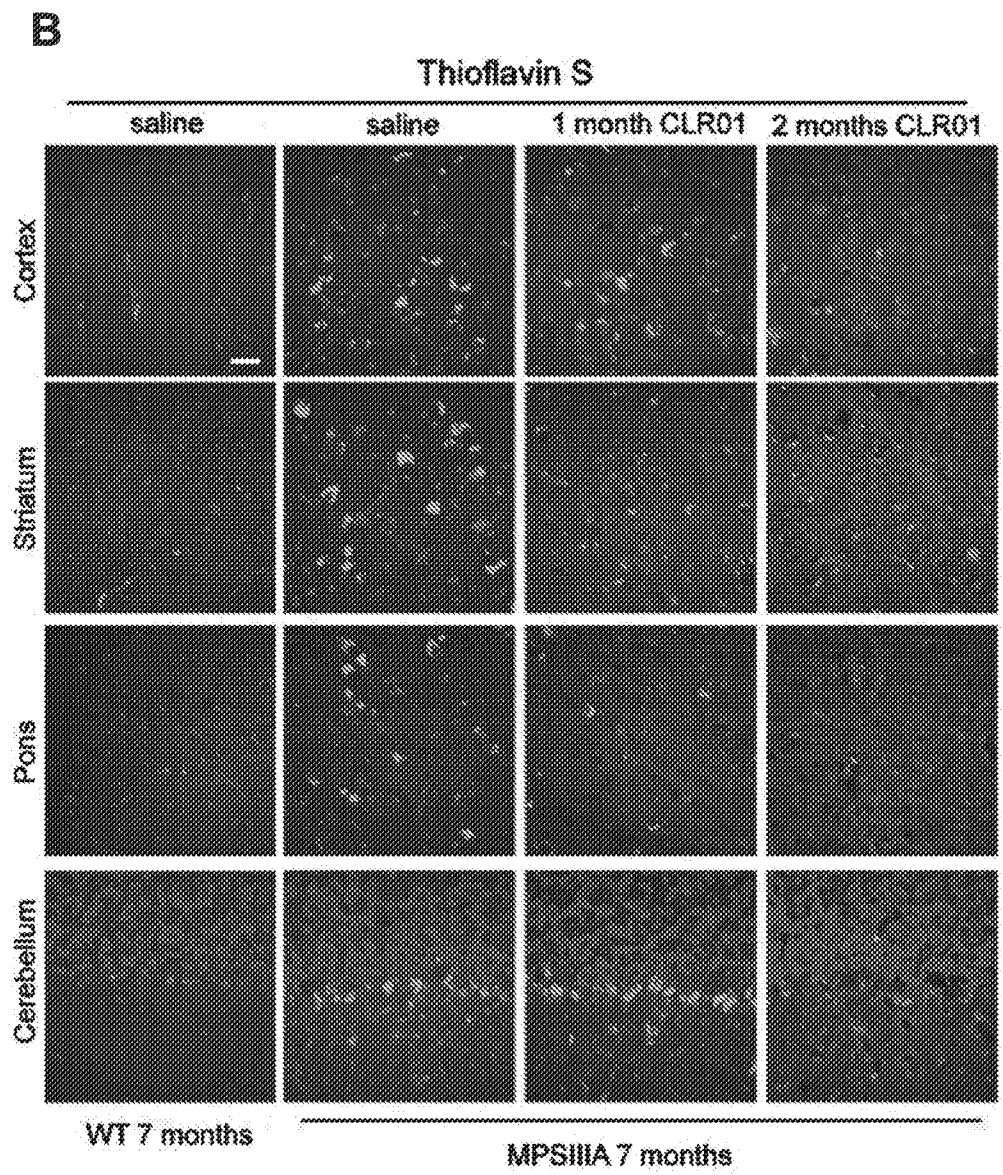
*Fig. 4, cont'd.*

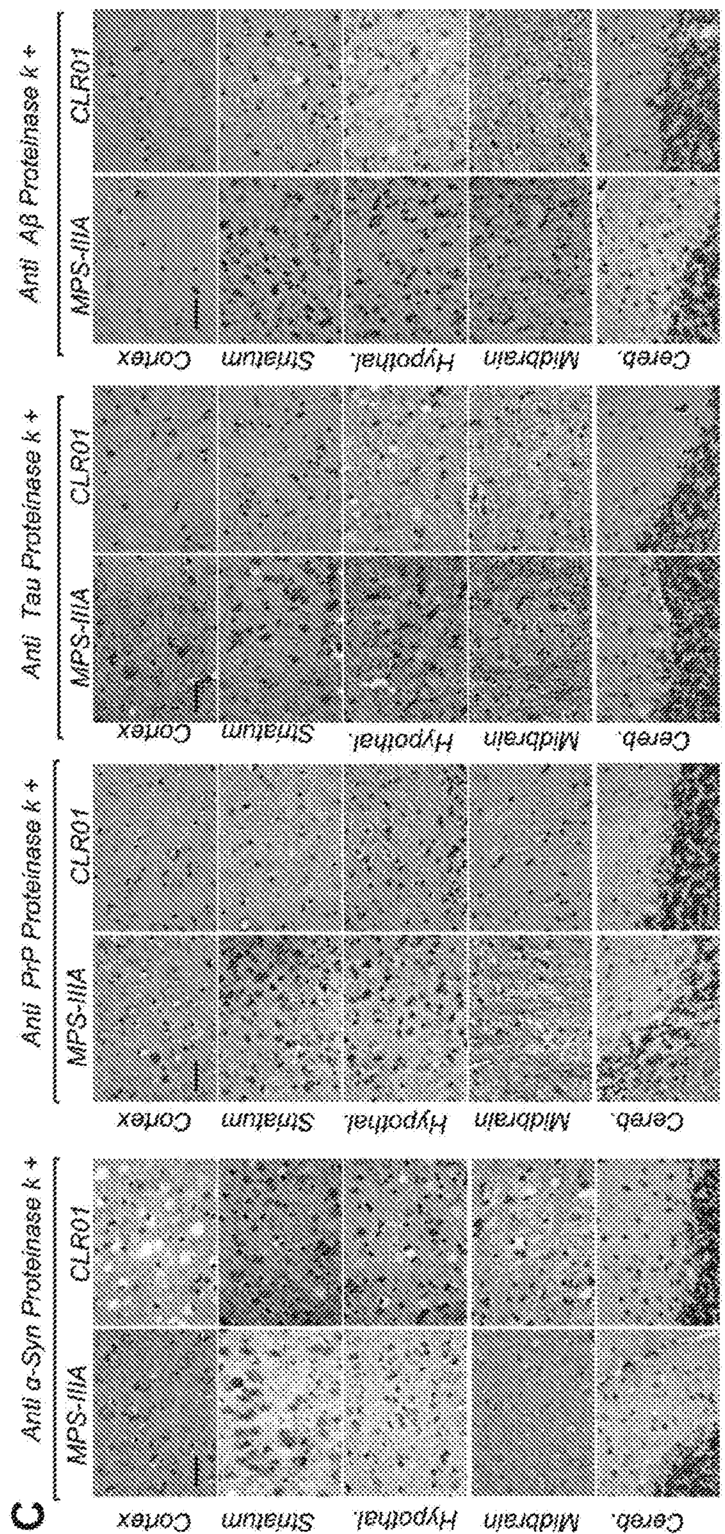
Fig. 4, cont'd.

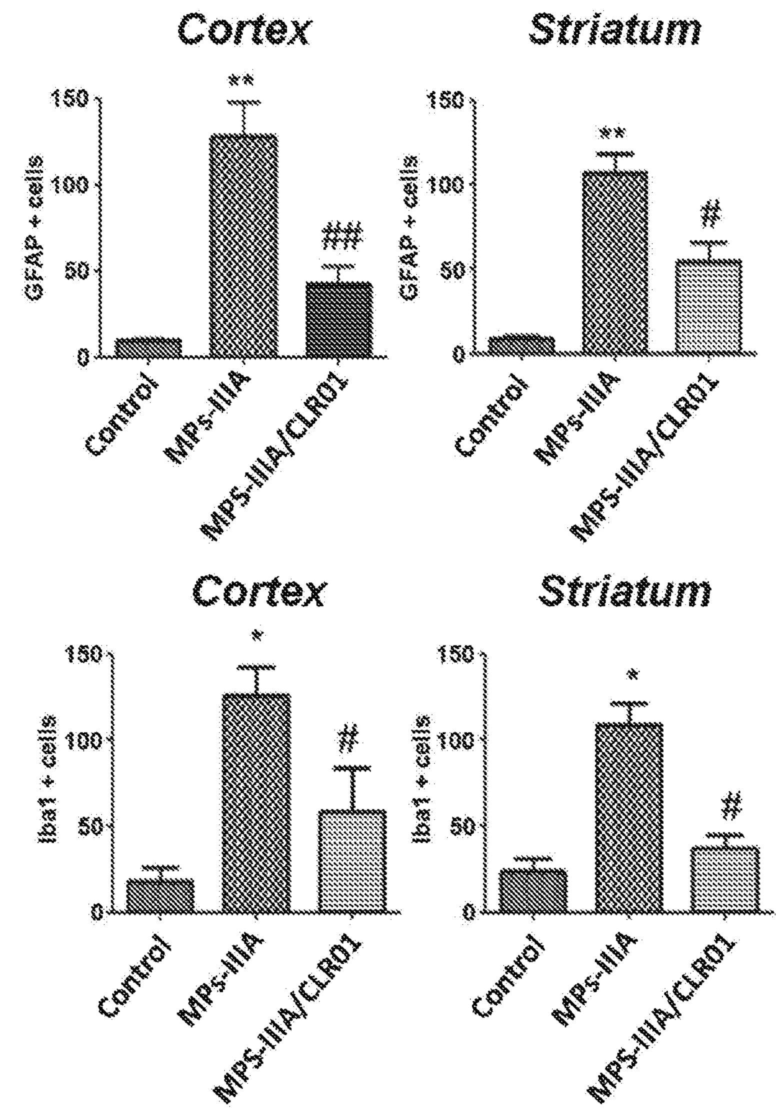
Fig. 5, cont'd.

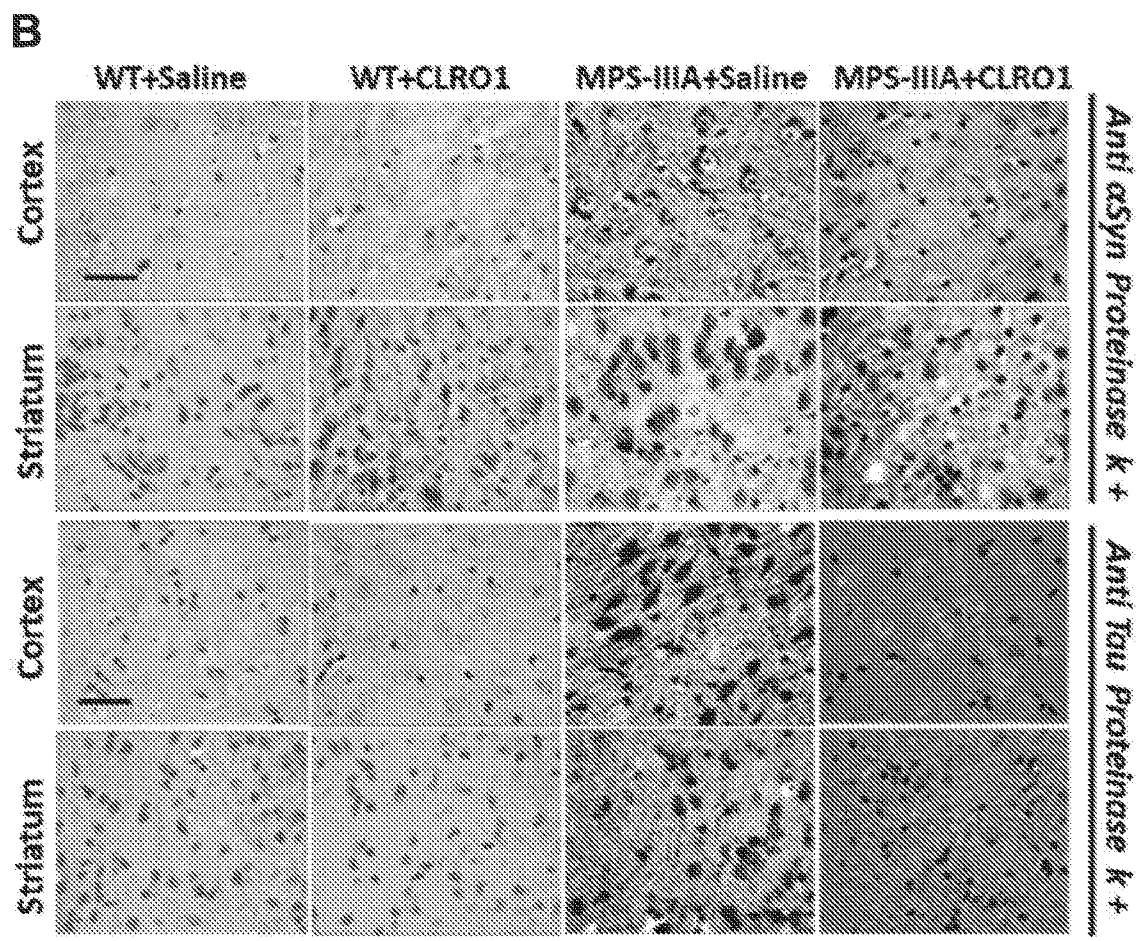
Fig. 6, cont'd.

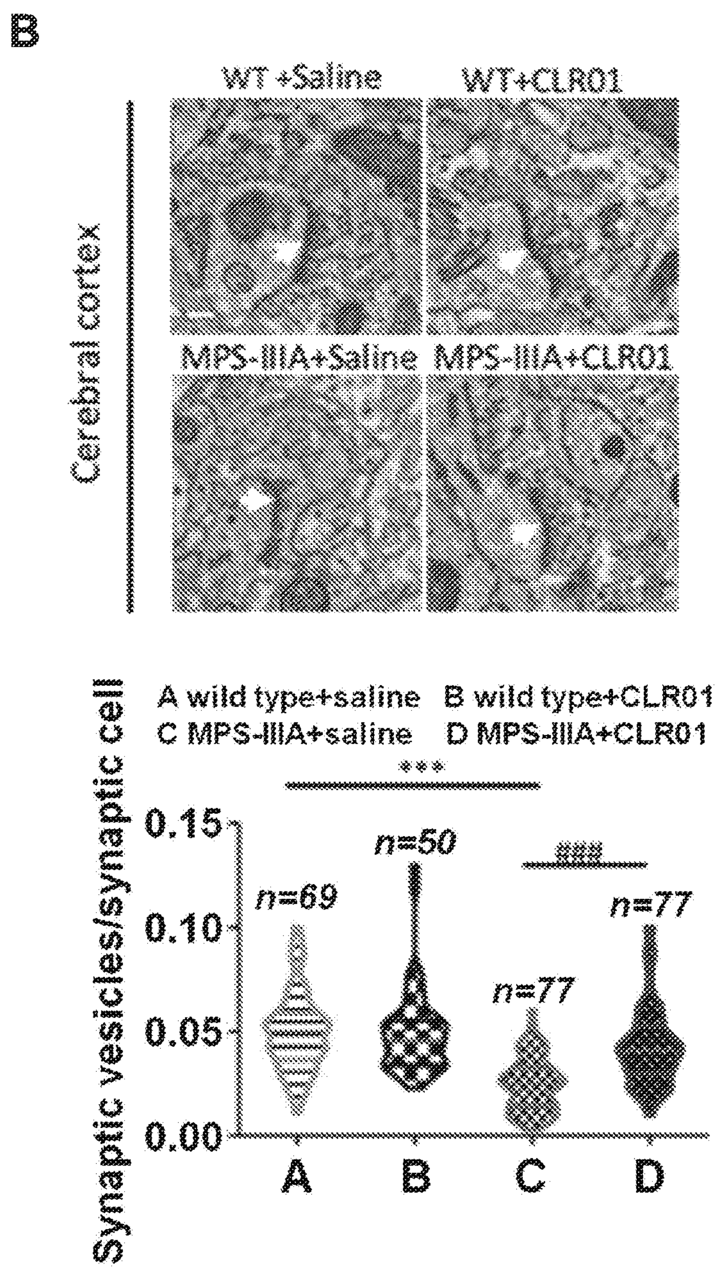
*Fig. 7, cont'd.*

*Fig. 7, cont'd.*

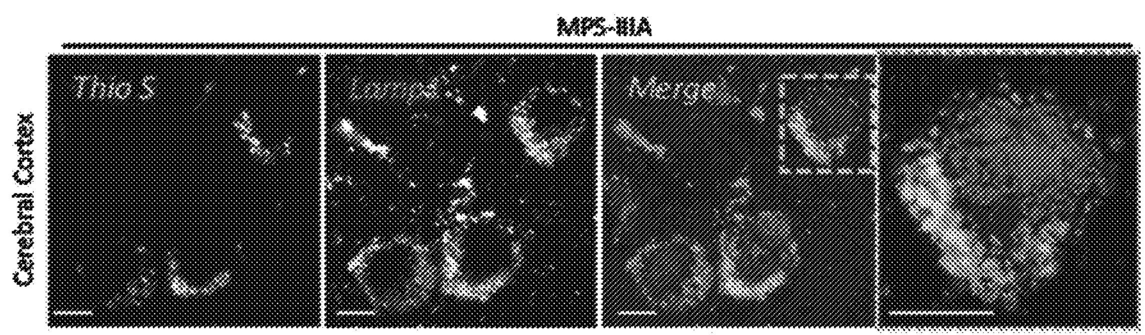
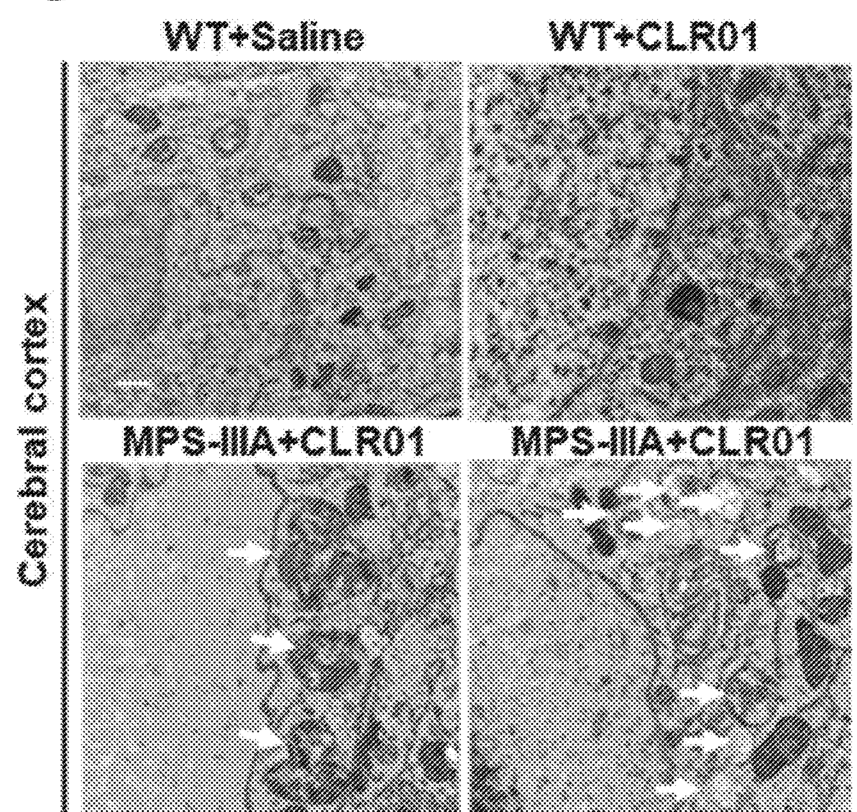
*Fig. 8, cont'd.*

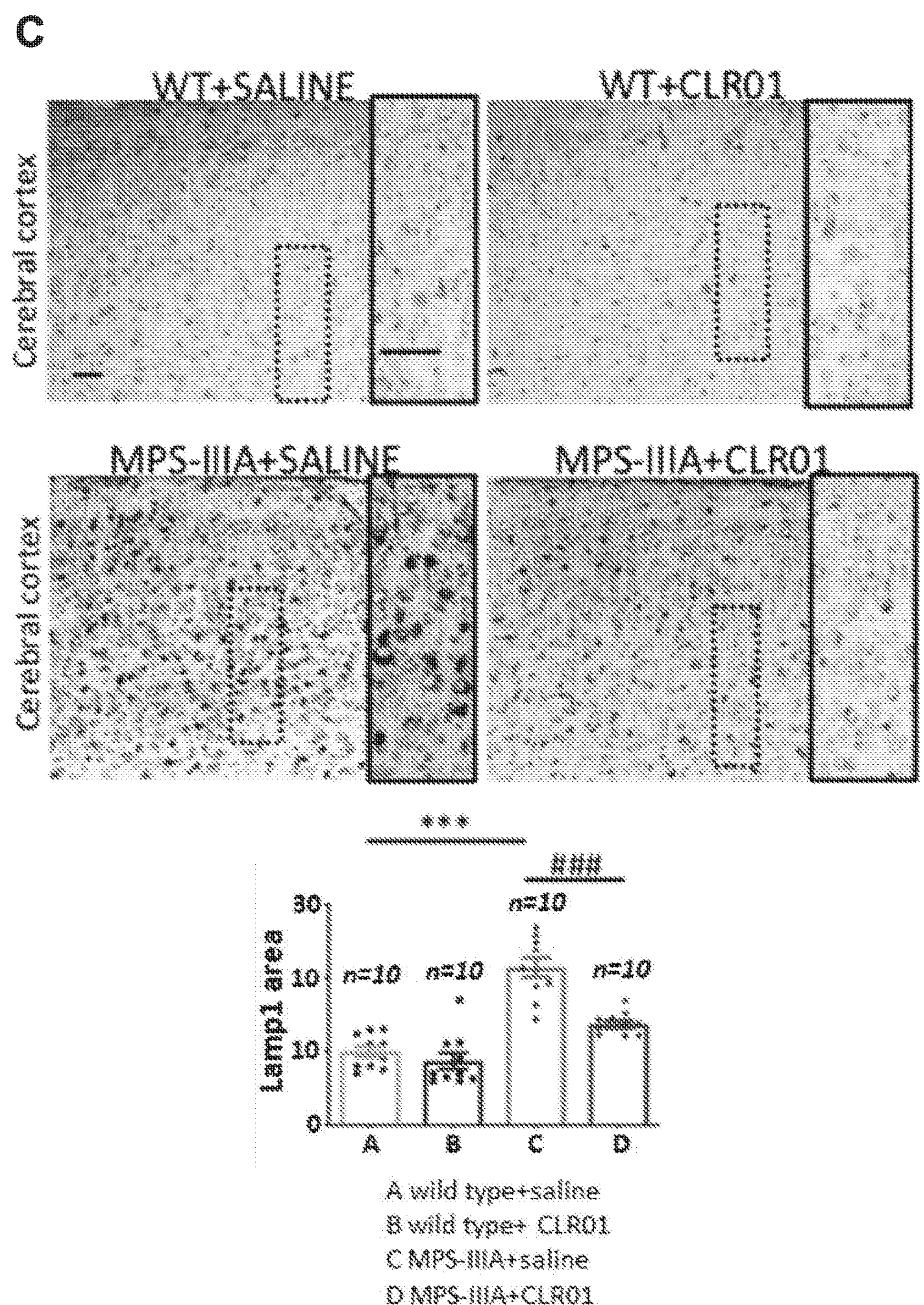
*Fig. 8, cont'd.*

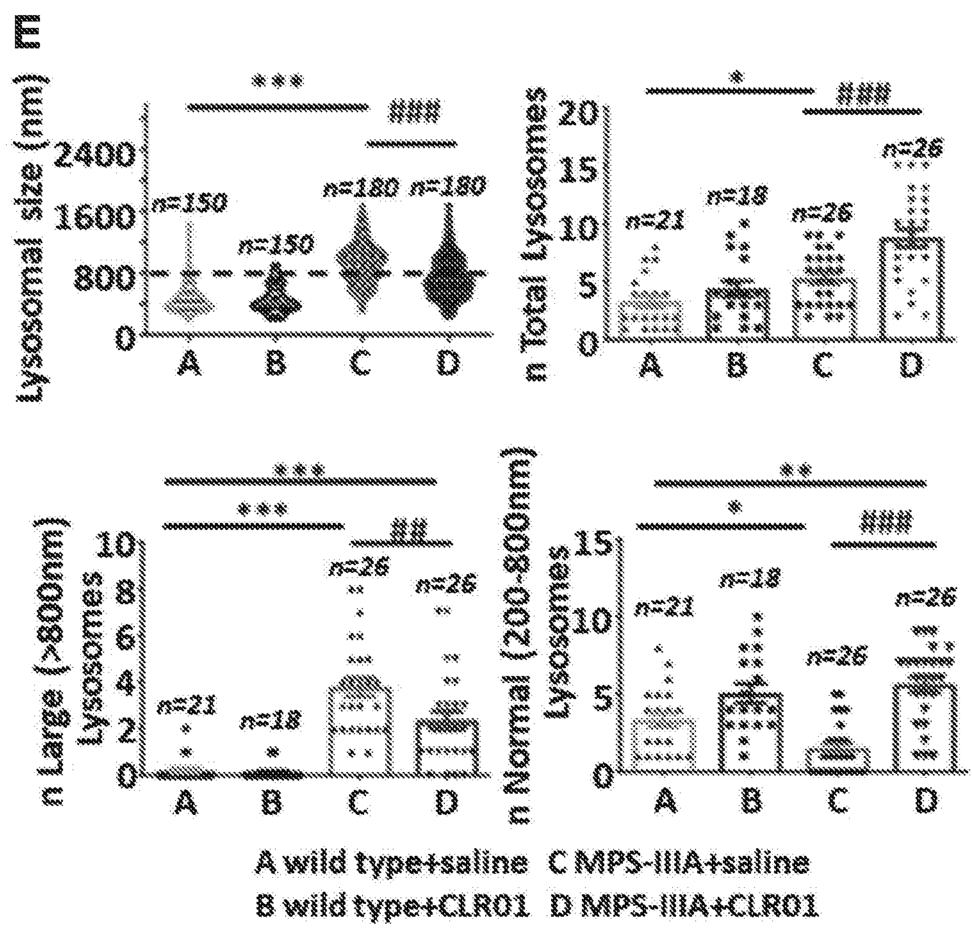
*Fig. 8, cont'd.*

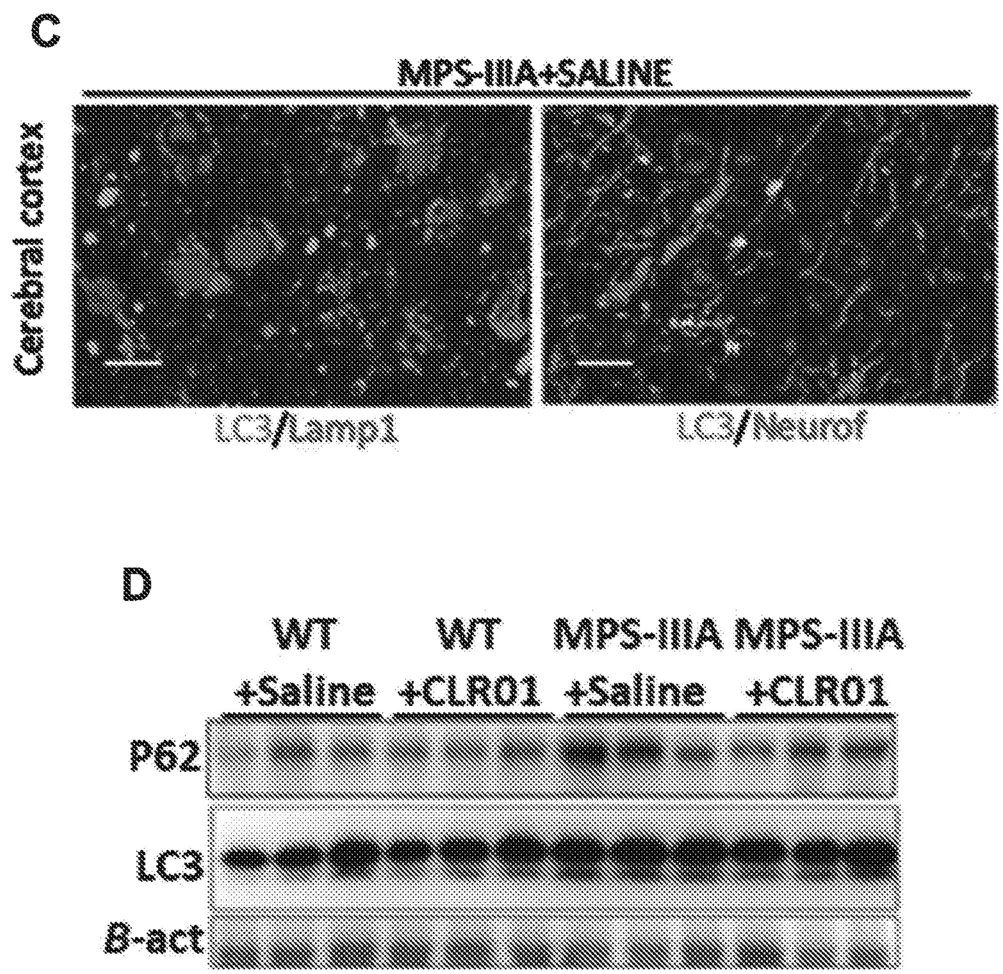
*Fig. 9, cont'd.*

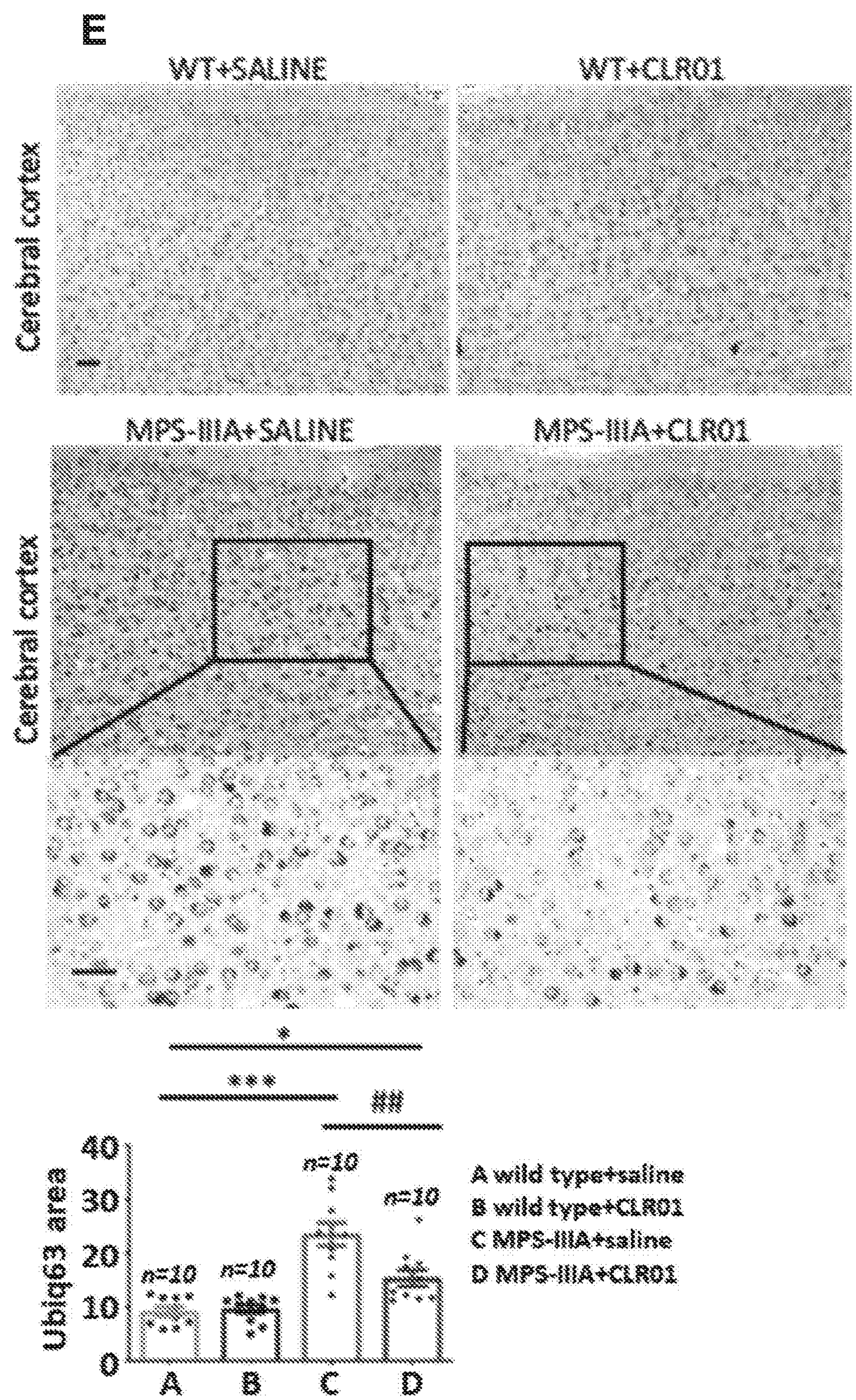
*Fig. 9, cont'd.*

TREATMENT OF LYSOSOMAL STORAGE DISORDERS

CROSS-REFERENCE TO RELATED APPLICATIONS

This application is a U.S. 371 National Phase of PCT/US2019/029222, filed on Apr. 25, 2019, which claims priority to and benefit of U.S. Ser. No. 62/663,964, filed on Apr. 27, 2018, both of which are incorporated herein by reference their entirety for all purposes.

STATEMENT OF GOVERNMENTAL SUPPORT

This invention was made with government support under Grant Number AG050721, awarded by the National Institutes of Health. The Government has certain rights in the invention.

BACKGROUND

Lysosomal storage disorders (LSDs) are inherited diseases characterized by lysosomal dysfunction and neurodegeneration (Schultz et al. (2011) *Trends Neurosci,* 34: 401-410; Settembre et al. (2013) *Nat. Rev. Mol. Cell. Biol.* 14: 283-296; Boustany et al. (2013) *Nat. Rev. Neurol.* 9: 583-598; Platt et al. (2012) *J. Cell Biol.* 199: 723-734). The term LSDs defines a group of approximately 70 disorders, typically due to single gene defects: deficiency of specific enzymes that are normally required for the breakdown of glycosaminoglycans (GAGs), make the cell unable to excrete the carbohydrate residues, which thus accumulate in the lysosomes of the cell. This accumulation disrupts the cell's normal functioning and gives rise to the clinical manifestations of LSDs.

Classically, lysosomal storage diseases encompassed only enzyme deficiencies of the lysosomal hydrolases; more recently, the concept has been expanded to include deficiencies or defects in proteins necessary for the normal post-translational modification of lysosomal enzymes (which themselves are often glycoproteins), activator proteins, or proteins important for proper intracellular trafficking between the lysosome and other intracellular compartments.

Although individually rare, lysosomal storage disorders as a group have a frequency of at least 1/7700 live births, making this disease group a major challenge for health care systems.

Neurological impairment and neurodegenerative processes are associated to lysosomal dysfunction and represent a predominant feature in most LSDs.

Neuropathology can occur in multiple brain regions (e.g., thalamus, cortex, hippocampus, and cerebellum) and involves unique temporal and spatial changes, which often entail early region-specific neurodegeneration and inflammation. As an example, Purkinje neurons degenerate in many of these diseases leading to cerebellar ataxia.

Particularly relevant LSDs are mucopolysaccharidoses (MPS), a group of metabolic disorders caused by the absence or malfunctioning of lysosomal enzymes needed to break down molecules called glycosaminoglycans, formerly called. mucopolysaccharides. MPSs can be subclassified as follows: Hurler syndrome (MPS IH), Hurler-Scheie syndrome (MPS I-H/S), Scheie syndrome (MPS IS), Hunter syndrome (MPS II), Sanfilippo syndrome (MPS III), Morquio syndrome (MP IV), Maroteaux-Lamy syndrome (MPS VI), Sly syndrome (MPS VII) and MPS IX. In the severe form of mucopolysaccharidosis type I (Hurler syndrome or MPS IH), delay in motor and intellectual development is one of the leading symptoms.

There are no cures for lysosomal storage diseases and treatment is mostly symptomatic. Current therapies for LSDs, comprising enzyme replacement therapy (ERT) and hematopoietic stem cell transplantation (HSCT), are some of the most expensive in medicine. HSCT has been attempted with varying results: as an example it has not exhibited significant improved clinical signs in MPS IIIA patients and mice, probably as a result of insufficient donor-derived enzyme production and/or uptake by host brain cells. Furthermore, it has a 15% risk of early death and requires a compatible donor.

Allogenic bone marrow grafts are contraindicated, as they do not slow the mental deterioration, even in patients engrafted pre-symptomatically.

Oral substrate reduction therapy (SRT), which inhibits glycosphingolipid synthesis thus slowing accumulation of breakdown products, has been developed for Gaucher disease. It is primarily used when ERT is refused, however it is also being studied as a part of combination therapy with ERT.

Gene therapy is currently under investigation in animal models for MPS IIIA and IIIB subtypes, however the neurological degradation accompanied by multiple complications requires a multidisciplinary management to allow adapted symptomatic treatment. As an example, PCT Publication No: WO2013096899 describes compositions and methods for CNS delivery of lysosomal enzymes (e.g., recombinant human arylsulfatase A (rhASA)) for effective treatment of lysosomal storage diseases (e.g. Metachromatic Leukodystrophy Disease).

However, to date there are no approved products for the treatment of brain genetic diseases, such as lysosomal storage disorders with neurologic impairment. Therefore, there is a compelling need for improved treatments for LSDs with neurological impairment.

SUMMARY

Many neurodegenerative diseases, including Alzheimer's and Parkinson's diseases, are characterized by the formation of insoluble aggregates from amyloidogenic proteins (Ciechanover & Kwon (2015) *Exp. Mol. Med.* 47(3): e147). These insoluble forms of the aggregated protein or peptide form by the intermolecular association of β-strands into β-sheets. The aggregation process can be caused by overproduction or poor clearance of amyloidogenic proteins and these aggregates are cytotoxic because they interfere with multiple cellular mechanisms, often contributing to cell death (Rahimi et al. (2008) *Curr. Alzheimer. Res.* 5: 319-341; Serpell (2000) *Biochim. Biophys. Acta.* 1502(1): 16-30).

The inventors previously discovered that α-synuclein accumulates at perikarya in LSDs brain contributing to neurodegenerative processes via a loss of function-mediated deregulation of presynaptic activity. They have now surprisingly found that several amyloid proteins, including α-synuclein, accumulate at perikarya (mostly into the lysosomal compartment) in models of LSDs and have characterized inclusions as amyloid-like deposits containing several disease-relevant proteins such as amyloid β-protein (Aβ), Prion Protein and Tau. The inventors have further unexpectedly shown that molecular tweezers, such as those described in PCT Publication No: WO2010102248, are capable of attenuating neuronal loss and reducing inflammation in LSDs, thus providing a novel treatment for LSDs with neurological impairment and proving that amyloid deposits have a pathogenic role in LSDs contributing to neuropathology through a gain of toxic function mechanism Accordingly, various embodiments contemplated herein may include, but need not be limited to, one or more of the following:

Embodiment 1: A method of treating a lysosomal storage disease in a mammal, said method comprising:

administering to said mammal an effective amount of a molecular tweezers that is capable of inhibiting protein aggregation.

Embodiment 2: The method of embodiment 1, wherein said molecular tweezers is capable of inhibiting aggregation of an amyloid protein.

Embodiment 3: The method of embodiment 2, wherein said amyloid protein comprises one or more proteins selected from the group consisting of α-synuclein, AO, Prion Protein and Tau.

Embodiment 4: The method according to any one of embodiments 1-3, wherein said effective amount is an amount effective to slow the progression, or stop, or reverse protein accumulation/aggregation associated with said lysosomal storage disease.

Embodiment 5: The method according to any one of embodiments 1-4, wherein said effective amount is an amount effective to ameliorate one or more symptoms of the pathology associated with said lysosomal storage disease and/or to reduce neurodegeneration and/or neuro-inflammation associated with said lysosomal storage disease.

Embodiment 6: The method of embodiment 5, wherein said method reduces neurodegeneration.

Embodiment 7: The method according to any one of embodiments 5-6, wherein said method reduces neuroinflammation.

Embodiment 8: The method according to any one of embodiments 5-7, wherein said method delays the onset, slows the progression or reduces memory-deficit.

Embodiment 9: The method according to any one of embodiments 5-8 wherein said method reduces abnormal lysosome size.

Embodiment 10: The method according to any one of embodiments 5-9 wherein said method re-activates autophagic flux.

Embodiment 11: The method according to any one of embodiments 1-10, wherein said effective amount is an amount effective to delay the onset, or to slow, or to stop, or to reverse progression of a pathology associated with said lysosomal storage disease.

Embodiment 12: The method according to any one of embodiments 1-11, wherein said administration is before appearance of symptoms in said mammal.

Embodiment 13: The method of embodiment 12, wherein said mammal is identified as having the lysosomal storage disease by the presence of a genetic marker for said lysosomal storage disease.

Embodiment 14: The method according to any one of embodiments 1-11, wherein said administration is within 3 months of birth, or within 6 months of birth, or within 1 year of birth, or within 3 years of birth.

Embodiment 15: The method according to any one of embodiments 1-14, wherein said lysosomal storage disease comprises a lysosomal storage disease characterized by neurological impairment and/or neurodegenerative processes.

Embodiment 16: The method of embodiment 15, wherein said lysosomal storage disease comprises a pathology selected from the group consisting of a mucopolysaccharidosis (MPS), aspartylglucosaminuria, GM1-gangliosidosis, Krabbe (globoid cell leukodystrophy or galactosylceramide lipidosis), Metachromatic leukodystrophy, Sandhoff disease, mucolipidosis type II (I-cell disease), mucolipidosis type IIIA (pseudo-Hurler polydystrophy), Niemann-Pick disease type C2 and C1, Danon disease, free sialic acid storage disorder, mucolipidosis type IV, and multiple sulfatase deficiency (MSD).

Embodiment 17: The method of embodiment 16, wherein said lysosomal storage disease comprises a mucopolysaccharidosis selected from the group consisting of Sanfilippo syndrome (MPS III), Hurler syndrome (MPS IH), Hurler-Scheie syndrome (MPS I-H/S), Scheie syndrome (MPS IS), Hunter syndrome (MPS II), Morquio syndrome (MP IV), Maroteaux-Lamy syndrome (MPS VI), Sly syndrome (MPS VII), and MPS IX.

Embodiment 18: The method of embodiment 17, wherein said mucopolysaccharidosis comprises Sanfilippo syndrome (MPS III).

Embodiment 19: The method of embodiment 17, wherein said amelioration of one or more symptoms of Sanfilippo syndrome (MPS III) comprises an amelioration of one or more symptoms selected from the group consisting of cognitive deficiencies, claw hand, visceromegaly, sleep disorders, loss of motor function, loss of communication abilities, and seizures.

Embodiment 20: The method of embodiment 17, wherein said method comprises slowing, stopping, or reversing the progression of one or more symptoms of Sanfilippo syndrome (MPS III) selected from the group consisting of cognitive deficiencies, claw hand, visceromegaly, sleep disorders, loss of motor function, loss of communication abilities, and seizures.

Embodiment 21: The method of embodiment 16, wherein said lysosomal storage disease comprises aspartylglucosaminuria.

Embodiment 22: The method of embodiment 21, wherein amelioration of one or more symptoms or aspartylglucosaminuria comprises an amelioration of one or more symptoms selected from the group consisting of delay or loss of speech, cognitive impairment, seizures, locomotor impairment, osteoporosis, and joint hypermobility.

Embodiment 23: The method of embodiment 21, wherein said method comprises slowing, stopping, or reversing the progression of one or more symptoms of aspartylglucosaminuria selected from the group consisting of increasing loss of speech, increasing cognitive impairment, increasing frequency and/or severity of seizures, increasing locomotor impairment, increasing osteoporosis, and increasing joint hypermobility.

Embodiment 24: The method of embodiment 16, wherein said lysosomal storage disease comprises GM1-gangliosidosis.

Embodiment 25: The method of embodiment 24, wherein amelioration of one or more symptoms of GM1-gangliosidosis comprises an amelioration of one or more symptoms selected from the group consisting of cognitive impairment, locomotor impairment, hepatosplenomegaly, skeletal abnormalities, seizures, clouding of the cornea, and loss of vision.

Embodiment 26: The method of embodiment 24, wherein said method comprises slowing, stopping, or reversing the progression of one or more symptoms of GM1-gangliosidosis selected from the group consisting of increasing cognitive impairment, progressive locomotor impairment, progressive hepatosplenomegaly, increasing skeletal abnormalities, increasing frequency and/or severity of seizures, increasing clouding of the cornea, and increasing loss of vision.

Embodiment 27: The method of embodiment 16, wherein said lysosomal storage disease comprises Krabbe disease (globoid cell leukodystrophy or galactosylceramide lipidosis).

Embodiment 28: The method of embodiment 27, wherein amelioration of one or more symptoms of Krabbe disease comprises an amelioration of one or more symptoms selected from the group consisting of irritability, fevers, limb stiffness, seizures, feeding difficulties, vomiting, and cognitive impairment, locomotor impairment, muscle weakness, spasticity, deafness, optic atrophy, optic nerve enlargement, blindness, paralysis, and difficulty when swallowing.

Embodiment 29: The method of embodiment 27, wherein said method comprises slowing, stopping, or reversing the progression of one or more symptoms of Krabbe disease selected from the group consisting of increasing irritability, fevers, limb stiffness, increasing frequency and/or severity of seizures, feeding difficulties, vomiting, cognitive impairment, locomotor impairment, muscle weakness, spasticity, deafness, optic atrophy, optic nerve enlargement, blindness, paralysis, and difficulty when swallowing.

Embodiment 30: The method of embodiment 16, wherein said lysosomal storage disease comprises metachromatic leukodystrophy.

Embodiment 31: The method of embodiment 30, wherein amelioration of one or more symptoms of leukodystrophy comprises an amelioration of one or more symptoms selected from the group consisting of leukodystrophy throughout CNS and/or peripheral nervous system, cognitive impairment, loss of sensation in the extremities (peripheral neuropathy), incontinence, seizures, paralysis, an inability to speak, blindness, and hearing loss.

Embodiment 32: The method of embodiment 30, wherein said method comprises slowing, stopping, or reversing the progression of one or more symptoms of leukodystrophy selected from the group consisting of increasing leukodystrophy throughout CNS and/or peripheral nervous system, cognitive impairment, loss of sensation in the extremities (peripheral neuropathy), incontinence, seizures, paralysis, an inability to speak, blindness, and hearing loss.

Embodiment 33: The method of embodiment 16, wherein said lysosomal storage disease comprises Sandhoff disease.

Embodiment 34: The method of embodiment 33, wherein amelioration of one or more symptoms of Sandhoff disease comprises cognitive impairment, loss of locomotor function, seizures, hearing loss vision loss, organomegaly, bone abnormalities, and paralysis.

Embodiment 35: The method of embodiment 33, wherein said method comprises slowing, stopping, or reversing the progression of one or more symptoms of Sandhoff disease selected from the group consisting of cognitive impairment, loss of locomotor function, seizures, hearing loss vision loss, organomegaly, bone abnormalities, and paralysis.

Embodiment 36: The method of embodiment 16, wherein said lysosomal storage disease comprises mucolipidosis type II (I-cell disease).

Embodiment 37: The method of embodiment 36, wherein amelioration of one or more symptoms of mucolipidosis type II comprises an amelioration of one or more symptoms selected from the group consisting of weak muscle tone (hypotonia), growth impairment, bone abnormalities, hyphosis, club feet, impaired mobility, heart valve abnormalities, prolonged or recurrent respiratory and/or ear infections, and hearing loss.

Embodiment 38: The method of embodiment 36, wherein said method comprises slowing, stopping, or reversing the progression of one or more symptoms of mucolipidosis type II selected from the group consisting of weak muscle tone (hypotonia), growth impairment, bone abnormalities, hyphosis, club feet, impaired mobility, heart valve abnormalities, prolonged or recurrent respiratory and/or ear infections, and hearing loss.

Embodiment 39: The method of embodiment 16, wherein said lysosomal storage disease comprises mucolipidosis type IIIA (pseudo-Hurler polydystrophy).

Embodiment 40: The method of embodiment 39, wherein amelioration of one or more symptoms comprises an amelioration of one or more symptoms of mucolipidosis type IIIA selected from the group consisting of joint stiffness, scoliosis, skeletal deformities of the hands (e.g., claw-hands), growth delays, deterioration of the hip joints, clouding of the corneas of the eyes, mild mental retardation, easy fatigability, carpal tunnel syndrome, and heart disease.

Embodiment 41: The method of embodiment 39, wherein said method comprises slowing, stopping, or reversing the progression of one or more symptoms of mucolipidosis type IIIA selected from the group consisting of joint stiffness, scoliosis, skeletal deformities of the hands (e.g., claw-hands), growth delays, deterioration of the hip joints, clouding of the corneas of the eyes, mild mental retardation, easy fatigability, carpal tunnel syndrome, and heart disease.

Embodiment 42: The method of embodiment 16, wherein said lysosomal storage disease comprises Niemann-Pick disease type C2 and C1.

Embodiment 43: The method of embodiment 42, wherein amelioration of one or more symptoms comprises an amelioration of one or more symptoms of Niemann-Pick disease selected from the group consisting of splenomegaly, hepatomegaly, hepatosplenomegaly, jaundice, cognitive impairment, cerebellar ataxia (unsteady walking with uncoordinated limb movements), dysarthria (slurred speech), dysphagia (difficulty in swallowing), tremor, epilepsy (both partial and generalized), vertical supranuclear palsy (upgaze palsy, downgaze palsy, saccadic palsy or paralysis), sleep inversion, gelastic cataplexy (sudden loss of muscle tone or drop attacks), dystonia (abnormal movements or postures caused by contraction of agonist and antagonist muscles across joints), spasticity (velocity dependent increase in muscle tone), hypotonia, ptosis (drooping of the upper eyelid), psychosis, progressive dementia, progressive hearing loss, bipolar disorder, major and psychotic depression, loss of volitional movement, and severe dementia.

Embodiment 44: The method of embodiment 42, wherein said method comprises slowing, stopping, or reversing the progression of one or more symptoms of Niemann-Pick disease selected from the group consisting of splenomegaly, hepatomegaly, hepatosplenomegaly, jaundice, cognitive impairment, cerebellar ataxia (unsteady walking with uncoordinated limb movements), dysarthria (slurred speech), dysphagia (difficulty in swallowing), tremor, epilepsy (both partial and generalized), vertical supranuclear palsy (upgaze palsy, downgaze palsy, saccadic palsy or paralysis), sleep inversion, gelastic cataplexy (sudden loss of muscle tone or drop attacks), dystonia (abnormal movements or postures caused by contraction of agonist and antagonist muscles across joints), spasticity (velocity dependent increase in muscle tone), hypotonia, ptosis (drooping of the upper eyelid), psychosis, progressive dementia, progressive hearing loss, bipolar disorder, major and psychotic depression, loss of volitional movement, and severe dementia.

Embodiment 45: The method of embodiment 16, wherein said lysosomal storage disease comprises Danon disease.

Embodiment 46: The method of embodiment 45, wherein amelioration of one or more symptoms of Danon disease comprises an amelioration of one or more symptoms selected from the group consisting of cardiomyopathy, skeletal muscle myopathy, and cognitive impairment.

Embodiment 47: The method of embodiment 45, wherein said method comprises slowing, stopping, or reversing the progression of one or more symptoms of Danon disease selected from the group consisting of cardiomyopathy, skeletal muscle myopathy, and cognitive impairment.

Embodiment 48: The method of embodiment 16, wherein said lysosomal storage disease comprises free sialic acid storage disorder.

Embodiment 49: The method of embodiment 48, wherein amelioration of one or more symptoms of free sialic acid storage disorder comprises an amelioration of one or more symptoms selected from the group consisting of cognitive impairment, developmental delay, weak muscle tone (hypotonia), failure to gain weight and grow at the expected rate (failure to thrive), bone malformations, an enlarged liver and spleen (hepatosplenomegaly), and an enlarged heart (cardiomegaly).

Embodiment 50: The method of embodiment 48, wherein said method comprises slowing, stopping, or reversing the progression of one or more symptoms of free sialic acid storage disorder selected from the group consisting of cognitive impairment, developmental delay, weak muscle tone (hypotonia), failure to gain weight and grow at the expected rate (failure to thrive), bone malformations, an enlarged liver and spleen (hepatosplenomegaly), and an enlarged heart (cardiomegaly).

Embodiment 51: The method of embodiment 16, wherein said lysosomal storage disease comprises mucolipidosis type IV.

Embodiment 52: The method of embodiment 51, wherein amelioration of one or more symptoms of mucolipidosis type IV comprises an amelioration of one or more symptoms selected from the group consisting of delayed development, vision impairment, psychomotor delay, cognitive impairment, limited or absent speech, difficulty chewing and swallowing, weak muscle tone (hypotonia), abnormal muscle stiffness (spasticity), locomotor impairment, clouding of the cornea, and impaired production of stomach acid (achlorhydria).

Embodiment 53: The method of embodiment 51, wherein said method comprises slowing, stopping, or reversing the progression of one or more symptoms of mucolipidosis type IV selected from the group consisting of delayed development, vision impairment, psychomotor delay, cognitive impairment, limited or absent speech, difficulty chewing and swallowing, weak muscle tone (hypotonia), abnormal muscle stiffness (spasticity), locomotor impairment, clouding of the cornea, and impaired production of stomach acid (achlorhydria).

Embodiment 54: The method of embodiment 16, wherein said lysosomal storage disease comprises multiple sulfatase deficiency (MSD).

Embodiment 55: The method of embodiment 54, wherein amelioration of one or more symptoms of multiple sulfatase deficiency comprises an amelioration of one or more symptoms selected from the group consisting of leukodystrophy, scoliosis, hepatosplenomegaly, psychomotor regression), and ichthyosis.

Embodiment 56: The method of embodiment 54, wherein said method comprises slowing, stopping, or reversing the progression of one or more symptoms of multiple sulfatase deficiency selected from the group consisting of leukodystrophy, scoliosis, hepatosplenomegaly, psychomotor regression), and ichthyosis.

Embodiment 57: The method according to any one of embodiments 15-56, wherein said amelioration of one or more symptoms comprises a reduction of neuroinflammation (and/or in certain embodiments, reduced memory deficit, and/or reactivated (restored) autophagic flux, and/or reduced abnormal lysosome size).

Embodiment 58: The method of embodiment 57, wherein said reduction of neuro-inflammation comprises a reduction in one or more markers of neuroinflammation, wherein said marker(s) of neuroinflammation are selected from the group consisting of Iba1 (marker microglial activation), GFAP (marker for astrocytic response), TNF-alpha, interleukins, and TGF-beta.

Embodiment 59: The method according to any one of embodiments 15-58, wherein said amelioration of one or more symptoms comprises a reduction in neuronal loss (neurodegeneration).

Embodiment 60: The method according to any one of embodiments 15-56, wherein method is effective to slow, or to stop, or to reverse progression of neuro-inflammation in said mammal.

Embodiment 61: The method of embodiment 60, wherein said method is effective to slow, or to stop, or to reverse progression of neuro-inflammation as characterized by a reduction in one or more markers of neuroinflammation, wherein said marker(s) of neuroinflammation are selected from the group consisting of Iba1 (marker microglial activation), GFAP (marker for astrocytic response), TNF-alpha, interleukins, and TGF-beta.

Embodiment 62: The method according to any one of embodiments 15-56, and 60-61, wherein said method is effective to slow, or to stop, or to reverse neuronal loss (neurodegeneration) in said mammal.

Embodiment 63: The method according to any one of embodiments 1-62, wherein said molecular tweezers is a molecular tweezers according to any one of formulas I to IV:

(I)

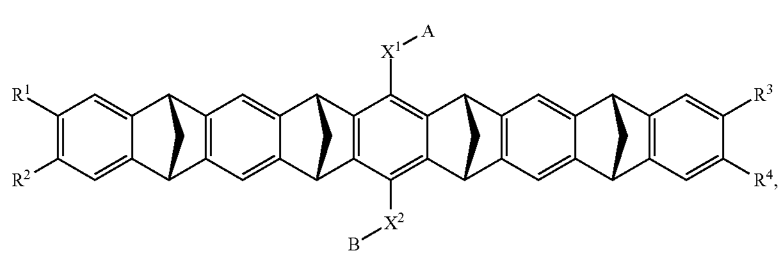

-continued (II)

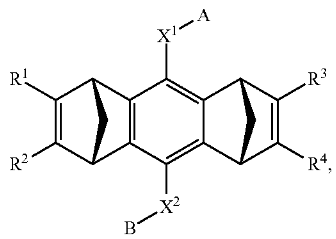

(III)

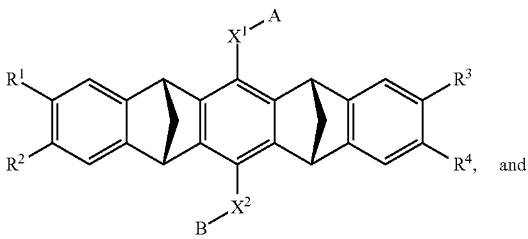

and (IV)

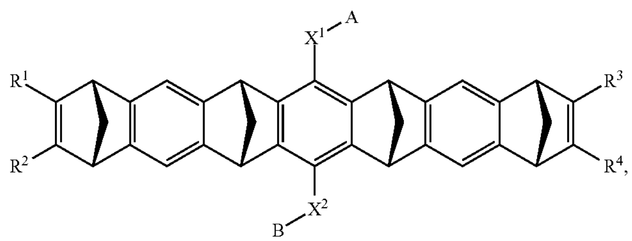

or a pharmaceutically acceptable salt, ester, amide, or prodrug thereof, wherein:

- $X^1$ and $X^2$ are both O;
- A alone, or A combined with $X^1$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate, and

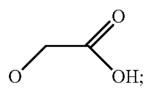

- B alone, or B combined with $X^2$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate and

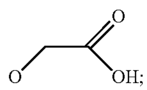

and

- each of $R^1$, $R^2$, $R^3$, and $R^4$ is, independently, selected from the group consisting of H, Cl, Br, I, OR, $NR_2$, $NO_2$, $CO_2H$, and $CO_2R^5$, wherein $R^5$ is alkyl, aryl or H, or
- $R^1$ and $R^2$ combine to form an aliphatic or aromatic ring, and/or
- $R^3$ and $R^4$ combine to form an aliphatic or aromatic ring.

Embodiment 64: The method of embodiment 63, wherein A and B are independently selected from the group consisting of

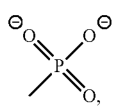

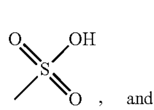

, and

-continued

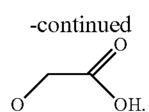

Embodiment 65: The method of embodiments 64, wherein A and B are the same.

Embodiment 66: The method of embodiment 63, wherein A and B are independently selected from the group consisting of

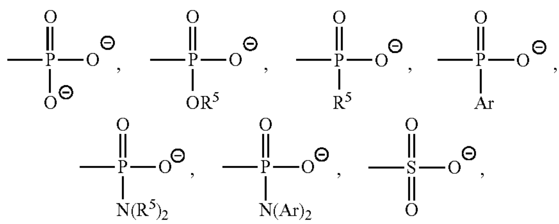

and $—(CH_2)_n—CO_2^-$, where $R^5$ is alkyl or H; n ranges from 1 to 10, and Ar is aryl.

Embodiment 67: The method of embodiments 66, wherein A and B are the same.

Embodiment 68: The method according to any one of embodiments 63-67, wherein said molecular tweezers is a molecular tweezers according to formula I or a pharmaceutically acceptable salt thereof.

Embodiment 69: The method according to any one of embodiments 63-67, wherein said molecular tweezers is a molecular tweezers according to formula II or a pharmaceutically acceptable salt thereof.

Embodiment 70: The method according to any one of embodiments 63-67, wherein said molecular tweezers is a molecular tweezers according to formula III or a pharmaceutically acceptable salt thereof.

Embodiment 71: The method according to any one of embodiments 63-67, wherein said molecular tweezers is a molecular tweezers according to formula IV or a pharmaceutically acceptable salt thereof.

Embodiment 72: The method of embodiment 63, wherein said molecular comprises a compound according to the formula:
(TW1/CLR01)
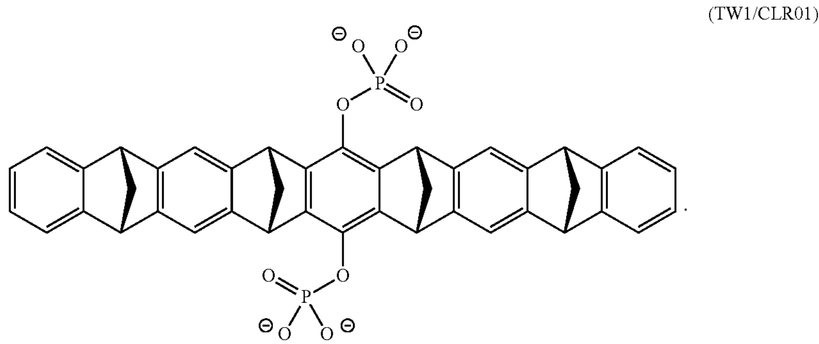 [SMILES: O=P([O-])([O-])Oc1c2c(c(OP(=O)([O-])[O-])c3c1[C@H]1C[C@@H]3c3cc4c(cc31)[C@H]1C[C@@H]4c3ccccc31)[C@H]1C[C@@H]2c2cc3c(cc21)[C@H]1C[C@@H]3c2ccccc21]
Embodiment 73: The method of embodiment 63, wherein said molecular tweezers comprises a compound according to the formula:
(TW2)
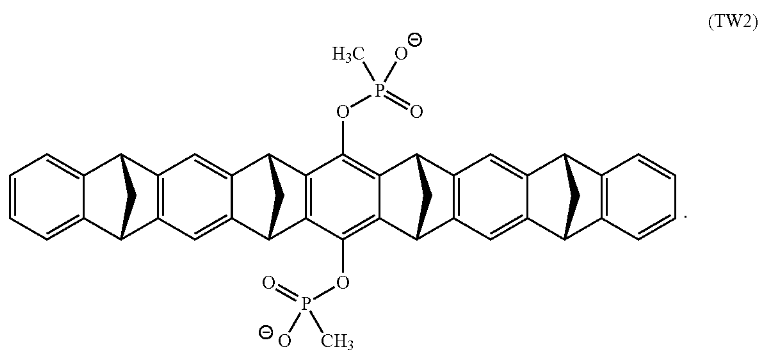 [SMILES: CP(=O)([O-])Oc1c2c(c(OP(C)(=O)[O-])c3c1[C@H]1C[C@@H]3c3cc4c(cc31)[C@H]1C[C@@H]4c3ccccc31)[C@H]1C[C@@H]2c2cc3c(cc21)[C@H]1C[C@@H]3c2ccccc21]
Embodiment 74: The method of embodiment 63, wherein said molecular tweezers comprises a compound according to the formula:
(TW4)
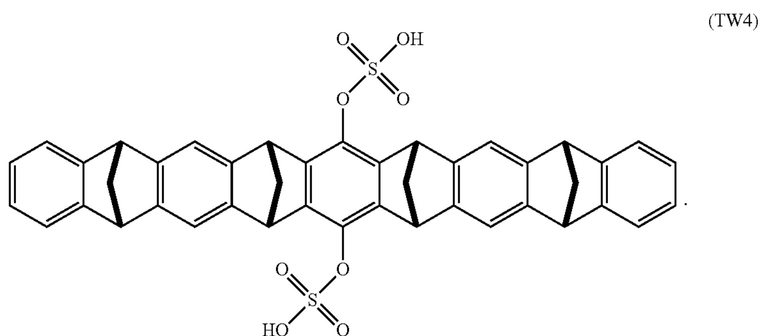

Embodiment 75: The method of embodiment 63, wherein said molecular tweezers comprises a compound according to the formula:|

(TW5)

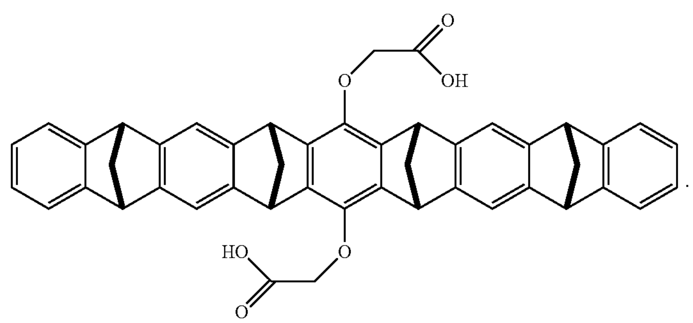

Embodiment 76: The method according to any one of embodiments 1-75, wherein said administration is via a route selected from the group consisting of oral delivery, isophoretic delivery, transdermal delivery, parenteral delivery, aerosol administration, administration via inhalation, intravenous administration, ocular administration, depot delivery, vaginal administration, and rectal administration.

Embodiment 77: The method according to any one of embodiments 1-75, wherein said administration is parenteral.

Embodiment 78: The method of embodiment 77, wherein said administration is selected from a route selected from the group consisting of intraspinal administration, intrathecal or epidural administration, subdural administration, subcutaneous administration, intravenous administration, administration through a subcutaneously implanted device, and administration is through a cannula.

Embodiment 79: The method according to any one of embodiments 1-78, wherein said method is used in combination with enzyme replacement therapy and/or gene therapy.

Embodiment 80: The method of embodiment 79, wherein said method is used in combination with a gene therapy selected form the group consisting of a lentivirus-mediated gene therapy, and AAV-mediated gene therapy, and gene editing (e.g., CRISPR) therapy.

Embodiment 81: The method according to any one of embodiments 1-80, wherein said mammal is a human.

Embodiment 82: The method according to any one of embodiments 1-80, wherein said mammal is non-human mammal.

Embodiment 83: A pharmaceutical formulation comprising a molecular tweezers that is capable of inhibiting protein aggregation for use in the treatment of a lysosomal storage disease in a mammal.

Embodiment 84: A molecular tweezers that is capable of inhibiting protein aggregation for use in the treatment of a lysosomal storage disease in a mammal.

Embodiment 85: The pharmaceutical formulation of embodiment 83 or the molecular tweezers of embodiment 84, wherein said molecular tweezers inhibits aggregation of an amyloid protein.

Embodiment 86: The pharmaceutical formulation or molecular tweezers of embodiment 85, wherein said amyloid protein comprises one or more proteins selected from the group consisting of α-synuclein, AP, Prion Protein and Tau.

Embodiment 87: The pharmaceutical formulation or molecular tweezers according to any one of embodiments 83-86, wherein said treatment is effective to slow the progression, or stop, or reverse protein accumulation/aggregation associated with said lysosomal storage disease.

Embodiment 88: The pharmaceutical formulation or molecular tweezers according to any one of embodiments 83-87, wherein said treatment is effective to ameliorate one or more symptoms of the pathology associated with said lysosomal storage disease.

Embodiment 89: The pharmaceutical formulation or molecular tweezers according to any one of embodiments 83-87, wherein said treatment is effective to slow, or to stop, or to reverse progression of a pathology associated with said lysosomal storage disease.

Embodiment 90: The pharmaceutical formulation or molecular tweezers according to any one of embodiments 83-89, wherein said treatment comprises administration before appearance of symptoms in said mammal.

Embodiment 91: The pharmaceutical formulation or molecular tweezers of embodiment 90, wherein said mammal is identified as having the lysosomal storage disease by the presence of a genetic marker for said lysosomal storage disease.

Embodiment 92: The pharmaceutical formulation or molecular tweezers according to any one of embodiments 83-89, wherein said treatment is within 3 months of birth, or within 6 months of birth, or within 1 year of birth, or within 3 years of birth.

Embodiment 93: The pharmaceutical formulation or molecular tweezers according to any one of embodiments 83-92, wherein said lysosomal storage disease comprises a lysosomal storage disease characterized by neurological impairment and/or neurodegenerative processes.

Embodiment 94: The pharmaceutical formulation or molecular tweezers of embodiment 93, wherein said lysosomal storage disease comprises a pathology selected from the group consisting of a mucopolysaccharidosis (MPS), aspartylglucosaminuria, GM1-gangliosidosis, Krabbe (globoid cell leukodystrophy or galactosylceramide lipidosis), Metachromatic leukodystrophy, Sandhoff disease, mucolipidosis type II (I-cell disease), mucolipidosis type IIIA (pseudo-Hurler polydystrophy), Niemann-Pick disease type C2 and C1, Danon disease, free sialic acid storage disorder, mucolipidosis type IV, and multiple sulfatase deficiency (MSD).

Embodiment 95: The pharmaceutical formulation or molecular tweezers of embodiment 94, wherein said lysosomal storage disease comprises a mucopolysaccharidosis selected from the group consisting of Sanfilippo syndrome (MPS III), Hurler syndrome (MPS IH), Hurler-Scheie syndrome (MPS I-H/S), Scheie syndrome (MPS IS), Hunter syndrome (MPS II), Morquio syndrome (MP IV), Maroteaux-Lamy syndrome (MPS VI), Sly syndrome (MPS VII), and MPS IX.

Embodiment 96: The pharmaceutical formulation or molecular tweezers of embodiment 95, wherein said mucopolysaccharidosis comprises Sanfilippo syndrome (MPS III).

Embodiment 97: The pharmaceutical formulation or molecular tweezers according to any one of embodiments 95-96, wherein said amelioration of one or more symptoms comprises an amelioration of one or more symptoms selected from the group consisting of cognitive deficiencies, claw hand, visceromegaly, sleep disorders, loss of motor function, loss of communication abilities, and seizures.

Embodiment 98: The pharmaceutical formulation or molecular tweezers according to any one of embodiments 95-96, wherein said treatment is effective to slow, stop, or reverse the progression of one or more symptoms selected from the group consisting of cognitive deficiencies, claw hand, visceromegaly, sleep disorders, loss of motor function, loss of communication abilities, and seizures.

Embodiment 99: The pharmaceutical formulation or molecular tweezers of embodiment 94, wherein said lysosomal storage disease comprises aspartylglucosaminuria.

Embodiment 100: The pharmaceutical formulation or molecular tweezers of embodiment 99, wherein amelioration of one or more symptoms or aspartylglucosaminuria comprises an amelioration of one or more symptoms selected from the group consisting of delay or loss of speech, cognitive impairment, seizures, locomotor impairment, osteoporosis, and joint hypermobility.

Embodiment 101: The pharmaceutical formulation or molecular tweezers of embodiment 99, wherein said treatment is effective to slow, stop, or reverse the progression of one or more symptoms of aspartylglucosaminuria selected from the group consisting of increasing loss of speech, increasing cognitive impairment, increasing frequency and/or severity of seizures, increasing locomotor impairment, increasing osteoporosis, and increasing joint hypermobility.

Embodiment 102: The pharmaceutical formulation or molecular tweezers of embodiment 94, wherein said lysosomal storage disease comprises GM1-gangliosidosis.

Embodiment 103: The pharmaceutical formulation or molecular tweezers of embodiment 102, wherein amelioration of one or more symptoms of GM1-gangliosidosis comprises an amelioration of one or more symptoms selected from the group consisting of cognitive impairment, locomotor impairment, hepatosplenomegaly, skeletal abnormalities, seizures, clouding of the cornea, and loss of vision.

Embodiment 104: The pharmaceutical formulation or molecular tweezers of embodiment 102, wherein said treatment is effective to slow, stop, or reverse the progression of one or more symptoms of GM1-gangliosidosis selected from the group consisting of increasing cognitive impairment, progressive locomotor impairment, progressive hepatosplenomegaly, increasing skeletal abnormalities, increasing frequency and/or severity of seizures, increasing clouding of the cornea, and increasing loss of vision.

Embodiment 105: The pharmaceutical formulation or molecular tweezers of embodiment 94, wherein said lysosomal storage disease comprises Krabbe disease (globoid cell leukodystrophy or galactosylceramide lipidosis).

Embodiment 106: The pharmaceutical formulation or molecular tweezers of embodiment 105, wherein amelioration of one or more symptoms of Krabbe disease comprises an amelioration of one or more symptoms selected from the group consisting of irritability, fevers, limb stiffness, seizures, feeding difficulties, vomiting, and cognitive impairment, locomotor impairment, muscle weakness, spasticity, deafness, optic atrophy, optic nerve enlargement, blindness, paralysis, and difficulty when swallowing.

Embodiment 107: The pharmaceutical formulation or molecular tweezers of embodiment 105, wherein said treatment is effective to slow, stop, or reverse the progression of one or more symptoms of Krabbe disease selected from the group consisting of increasing irritability, fevers, limb stiffness, increasing frequency and/or severity of seizures, feeding difficulties, vomiting, cognitive impairment, locomotor impairment, muscle weakness, spasticity, deafness, optic atrophy, optic nerve enlargement, blindness, paralysis, and difficulty when swallowing.

Embodiment 108: The pharmaceutical formulation or molecular tweezers of embodiment 94, wherein said lysosomal storage disease comprises metachromatic leukodystrophy.

Embodiment 109: The pharmaceutical formulation or molecular tweezers of embodiment 108, wherein amelioration of one or more symptoms of leukodystrophy comprises an amelioration of one or more symptoms selected from the group consisting of leukodystrophy throughout CNS and/or peripheral nervous system, cognitive impairment, loss of sensation in the extremities (peripheral neuropathy), incontinence, seizures, paralysis, an inability to speak, blindness, and hearing loss.

Embodiment 110: The pharmaceutical formulation or molecular tweezers of embodiment 108, wherein said treatment is effective to slow, stop, or reverse the progression of one or more symptoms of leukodystrophy selected from the group consisting of increasing leukodystrophy throughout CNS and/or peripheral nervous system, cognitive impairment, loss of sensation in the extremities (peripheral neuropathy), incontinence, seizures, paralysis, an inability to speak, blindness, and hearing loss.

Embodiment 111: The pharmaceutical formulation or molecular tweezers of embodiment 94, wherein said lysosomal storage disease comprises Sandhoff disease.

Embodiment 112: The pharmaceutical formulation or molecular tweezers of embodiment 111, wherein amelioration of one or more symptoms of Sandhoff disease comprises cognitive impairment, loss of locomotor function, seizures, hearing loss vision loss, organomegaly, bone abnormalities, and paralysis.

Embodiment 113: The pharmaceutical formulation or molecular tweezers of embodiment 111, wherein said treatment is effective to slow, stop, or reverse the progression of one or more symptoms of Sandhoff disease selected from the group consisting of cognitive impairment, loss of locomotor function, seizures, hearing loss vision loss, organomegaly, bone abnormalities, and paralysis.

Embodiment 114: The pharmaceutical formulation or molecular tweezers of embodiment 94, wherein said lysosomal storage disease comprises mucolipidosis type II (I-cell disease).

Embodiment 115: The pharmaceutical formulation or molecular tweezers of embodiment 114, wherein amelioration of one or more symptoms of mucolipidosis type II comprises an amelioration of one or more symptoms selected from the group consisting of weak muscle tone (hypotonia), growth impairment, bone abnormalities, hyphosis, club feet, impaired mobility, heart valve abnormalities, prolonged or recurrent respiratory and/or ear infections, and hearing loss.

Embodiment 116: The pharmaceutical formulation or molecular tweezers of embodiment 114, wherein said treatment is effective to slow, stop, or reverse the progression of one or more symptoms of mucolipidosis type II selected from the group consisting of weak muscle tone (hypotonia), growth impairment, bone abnormalities, hyphosis, club feet, impaired mobility, heart valve abnormalities, prolonged or recurrent respiratory and/or ear infections, and hearing loss.

Embodiment 117: The pharmaceutical formulation or molecular tweezers of embodiment 94, wherein said lysosomal storage disease comprises mucolipidosis type IIIA (pseudo-Hurler polydystrophy).

Embodiment 118: The pharmaceutical formulation or molecular tweezers of embodiment 117, wherein amelioration of one or more symptoms comprises an amelioration of one or more symptoms of mucolipidosis type IIIA selected from the group consisting of joint stiffness, scoliosis, skeletal deformities of the hands (e.g., claw-hands), growth delays, deterioration of the hip joints, clouding of the corneas of the eyes, mild mental retardation, easy fatigability, carpal tunnel syndrome, and heart disease.

Embodiment 119: The pharmaceutical formulation or molecular tweezers of embodiment 117, wherein said treatment is effective to slow, stop, or reverse the progression of one or more symptoms of mucolipidosis type IIIA selected from the group consisting of joint stiffness, scoliosis, skeletal deformities of the hands (e.g., claw-hands), growth delays, deterioration of the hip joints, clouding of the corneas of the eyes, mild mental retardation, easy fatigability, carpal tunnel syndrome, and heart disease.

Embodiment 120: The pharmaceutical formulation or molecular tweezers of embodiment 94, wherein said lysosomal storage disease comprises Niemann-Pick disease type C2 and C1.

Embodiment 121: The pharmaceutical formulation or molecular tweezers of embodiment 120, wherein amelioration of one or more symptoms comprises an amelioration of one or more symptoms of Niemann-Pick disease selected from the group consisting of splenomegaly, hepatomegaly, hepatosplenomegaly, jaundice, cognitive impairment, cerebellar ataxia (unsteady walking with uncoordinated limb movements), dysarthria (slurred speech), dysphagia (difficulty in swallowing), tremor, epilepsy (both partial and generalized), vertical supranuclear palsy (upgaze palsy, downgaze palsy, saccadic palsy or paralysis), sleep inversion, gelastic cataplexy (sudden loss of muscle tone or drop attacks), dystonia (abnormal movements or postures caused by contraction of agonist and antagonist muscles across joints), spasticity (velocity dependent increase in muscle tone), hypotonia, ptosis (drooping of the upper eyelid), psychosis, progressive dementia, progressive hearing loss, bipolar disorder, major and psychotic depression, loss of volitional movement, and severe dementia.

Embodiment 122: The pharmaceutical formulation or molecular tweezers of embodiment 120, wherein said treatment is effective to slow, stop, or reverse the progression of one or more symptoms of Niemann-Pick disease selected from the group consisting of splenomegaly, hepatomegaly, hepatosplenomegaly, jaundice, cognitive impairment, cerebellar ataxia (unsteady walking with uncoordinated limb movements), dysarthria (slurred speech), dysphagia (difficulty in swallowing), tremor, epilepsy (both partial and generalized), vertical supranuclear palsy (upgaze palsy, downgaze palsy, saccadic palsy or paralysis), sleep inversion, gelastic cataplexy (sudden loss of muscle tone or drop attacks), dystonia (abnormal movements or postures caused by contraction of agonist and antagonist muscles across joints), spasticity (velocity dependent increase in muscle tone), hypotonia, ptosis (drooping of the upper eyelid), psychosis, progressive dementia, progressive hearing loss, bipolar disorder, major and psychotic depression, loss of volitional movement, and severe dementia.

Embodiment 123: The pharmaceutical formulation or molecular tweezers of embodiment 94, wherein said lysosomal storage disease comprises Danon disease.

Embodiment 124: The pharmaceutical formulation or molecular tweezers of embodiment 123, wherein amelioration of one or more symptoms of Danon disease comprises an amelioration of one or more symptoms selected from the group consisting of cardiomyopathy, skeletal muscle myopathy, and cognitive impairment.

Embodiment 125: The pharmaceutical formulation or molecular tweezers of embodiment 123, wherein said treatment is effective to slow, stop, or reverse the progression of one or more symptoms of Danon disease selected from the group consisting of cardiomyopathy, skeletal muscle myopathy, and cognitive impairment.

Embodiment 126: The pharmaceutical formulation or molecular tweezers of embodiment 94, wherein said lysosomal storage disease comprises free sialic acid storage disorder.

Embodiment 127: The pharmaceutical formulation or molecular tweezers of embodiment 126, wherein amelioration of one or more symptoms of free sialic acid storage disorder comprises an amelioration of one or more symptoms selected from the group consisting of cognitive impairment, developmental delay, weak muscle tone (hypotonia), failure to gain weight and grow at the expected rate (failure to thrive), bone malformations, an enlarged liver and spleen (hepatosplenomegaly), and an enlarged heart (cardiomegaly).

Embodiment 128: The pharmaceutical formulation or molecular tweezers of embodiment 126, wherein said treatment is effective to slow, stop, or reverse the progression of one or more symptoms of free sialic acid storage disorder selected from the group consisting of cognitive impairment, developmental delay, weak muscle tone (hypotonia), failure to gain weight and grow at the expected rate (failure to thrive), bone malformations, an enlarged liver and spleen (hepatosplenomegaly), and an enlarged heart (cardiomegaly).

Embodiment 129: The pharmaceutical formulation or molecular tweezers of embodiment 94, wherein said lysosomal storage disease comprises mucolipidosis type IV.

Embodiment 130: The pharmaceutical formulation or molecular tweezers of embodiment 129, wherein amelioration of one or more symptoms of mucolipidosis type IV comprises an amelioration of one or more symptoms selected from the group consisting of delayed development, vision impairment, psychomotor delay, cognitive impairment, limited or absent speech, difficulty chewing and swallowing, weak muscle tone (hypotonia), abnormal muscle stiffness (spasticity), locomotor impairment, clouding of the cornea, and impaired production of stomach acid (achlorhydria).

Embodiment 131: The pharmaceutical formulation or molecular tweezers of embodiment 129, wherein said treatment is effective to slow, stop, or reverse the progression of one or more symptoms of mucolipidosis type IV selected from the group consisting of delayed development, vision impairment, psychomotor delay, cognitive impairment, limited or absent speech, difficulty chewing and swallowing, weak muscle tone (hypotonia), abnormal muscle stiffness (spasticity), locomotor impairment, clouding of the cornea, and impaired production of stomach acid (achlorhydria).

Embodiment 132: The pharmaceutical formulation or molecular tweezers of embodiment 94, wherein said lysosomal storage disease comprises multiple sulfatase deficiency (MSD).

Embodiment 133: The pharmaceutical formulation or molecular tweezers of embodiment 132, wherein amelioration of one or more symptoms of multiple sulfatase deficiency comprises an amelioration of one or more symptoms selected from the group consisting of leukodystrophy, scoliosis, hepatosplenomegaly, psychomotor regression), and ichthyosis.

Embodiment 134: The pharmaceutical formulation or molecular tweezers of embodiment 132, wherein said treatment is effective to slow, stop, or reverse the progression of one or more symptoms of multiple sulfatase deficiency selected from the group consisting of leukodystrophy, scoliosis, hepatosplenomegaly, psychomotor regression), and ichthyosis.

Embodiment 135: The pharmaceutical formulation or molecular tweezers according to any one of embodiments 93-134, wherein said amelioration of one or more symptoms comprises a reduction of neuroinflammation.

Embodiment 136: The pharmaceutical formulation or molecular tweezers of embodiment 135, wherein said reduction of neuro-inflammation comprises a reduction in one or more markers of neuroinflammation, wherein said marker(s) of neuroinflammation are selected from the group consisting of Iba1 (marker microglial activation), GFAP (marker for astrocytic response), TNF-alpha, interleukins, and TGF-beta.

Embodiment 137: The pharmaceutical formulation or molecular tweezers according to any one of embodiments 93-136, wherein said amelioration of one or more symptoms comprises a reduction neuronal loss (neurodegeneration).

Embodiment 138: The pharmaceutical formulation or molecular tweezers according to any one of embodiments 93-134, wherein treatment is effective to slow, or to stop, or to reverse progression of neuro-inflammation in said mammal.

Embodiment 139: The pharmaceutical formulation or molecular tweezers of embodiment 138, wherein said treatment is effective to slow, or to stop, or to reverse progression of neuro-inflammation as characterized by a reduction in one or more markers of neuroinflammation, wherein said marker(s) of neuroinflammation are selected from the group consisting of Iba1 (marker microglial activation), GFAP (marker for astrocytic response), TNF-alpha, interleukins, and TGF-beta.

Embodiment 140: The pharmaceutical formulation or molecular tweezers according to any one of embodiments 93-134, and 138-139, wherein said treatment is effective to slow, or to stop, or to reverse neuronal loss (neurodegeneration) in said mammal.

Embodiment 141: The pharmaceutical formulation or molecular tweezers according to any one of embodiments 83-140, wherein said molecular tweezers is a molecular tweezers according to any one of formulas I to IV:

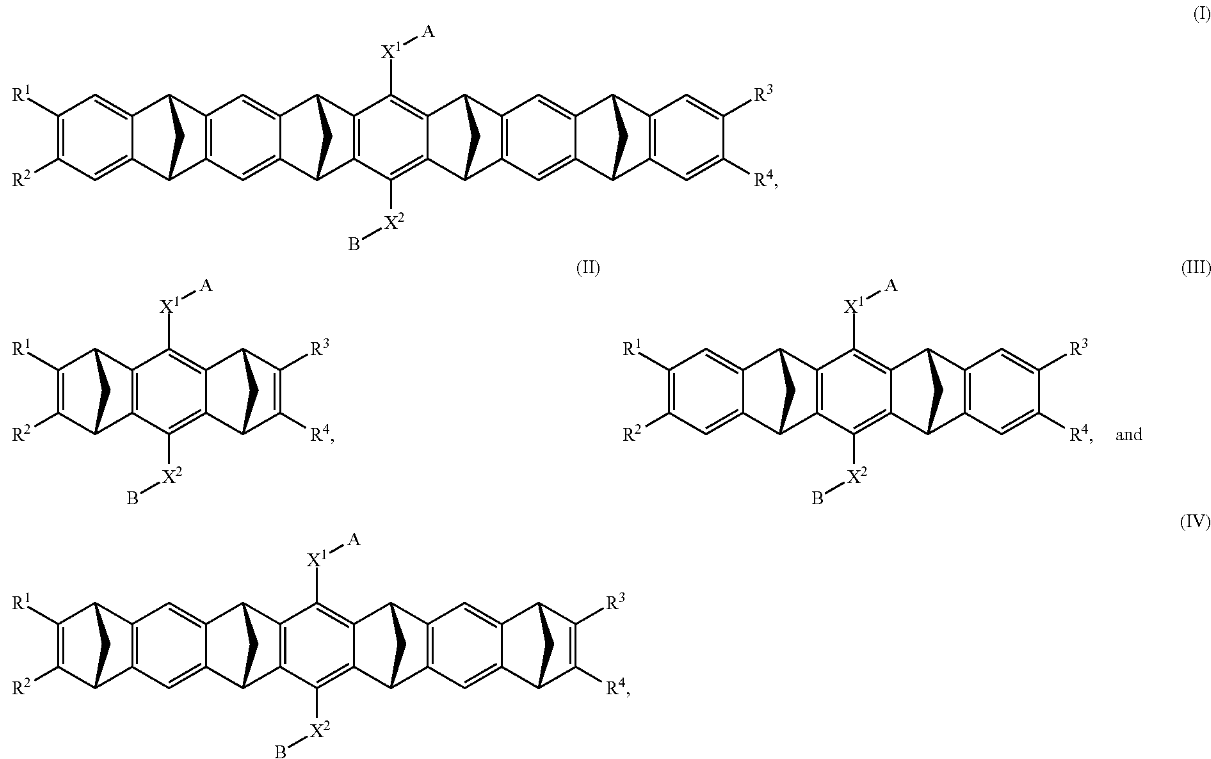

or a pharmaceutically acceptable salt, ester, amide, or prodrug thereof, wherein:

$X^1$ and $X^2$ are both O;

A alone, or A combined with $X^1$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate, and

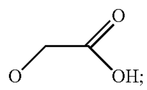

B alone, or B combined with $X^2$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate and

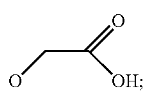

and each of $R^1$, $R^2$, $R^3$, and $R^4$ is, independently, selected from the group consisting of H, Cl, Br, I, OR, $NR_2$, $NO_2$, $CO_2H$, and $CO_2R^5$, wherein $R^5$ is alkyl, aryl or H, or $R^1$ and $R^2$ combine to form an aliphatic or aromatic ring, and/or $R^3$ and $R^4$ combine to form an aliphatic or aromatic ring.

Embodiment 142: The pharmaceutical formulation or molecular tweezers of embodiment 141, wherein A and B are independently selected from the group consisting of

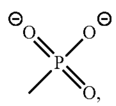

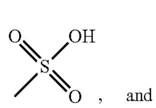

, and

OH.

Embodiment 143: The pharmaceutical formulation or molecular tweezers of embodiment 142, wherein A and B are the same.

Embodiment 144: The pharmaceutical formulation or molecular tweezers of embodiment 141, wherein A and B are independently selected from the group consisting of

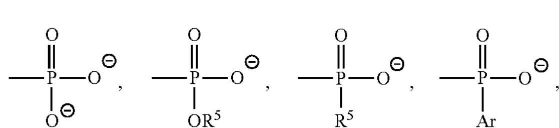

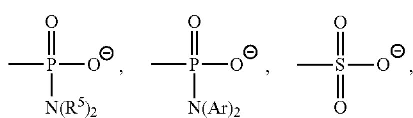

and $(CH_2)_n$—$CO_2^-$, where $R^5$ is alkyl or H; n ranges from 1 to 10, and Ar is aryl.

Embodiment 145: The pharmaceutical formulation or molecular tweezers of embodiment 144, wherein A and B are the same.

Embodiment 146: The pharmaceutical formulation or molecular tweezers according to any one of embodiments 141-145, wherein said molecular tweezers is a molecular tweezers according formula I or a pharmaceutically acceptable salt thereof.

Embodiment 147: The pharmaceutical formulation or molecular tweezers according to any one of embodiments 141-145, wherein said molecular tweezers is a molecular tweezers according formula II or a pharmaceutically acceptable salt thereof.

Embodiment 148: The pharmaceutical formulation or molecular tweezers according to any one of embodiments 141-145, wherein said molecular tweezers is a molecular tweezers according formula III or a pharmaceutically acceptable salt thereof.

Embodiment 149: The pharmaceutical formulation or molecular tweezers according to any one of embodiments 141-145, wherein said molecular tweezers is a molecular tweezers according formula IV or a pharmaceutically acceptable salt thereof.

Embodiment 150: The pharmaceutical formulation or molecular tweezers of embodiment 141, wherein said molecular tweezers comprises a compound according to the formula:

(TW1/CLR01)

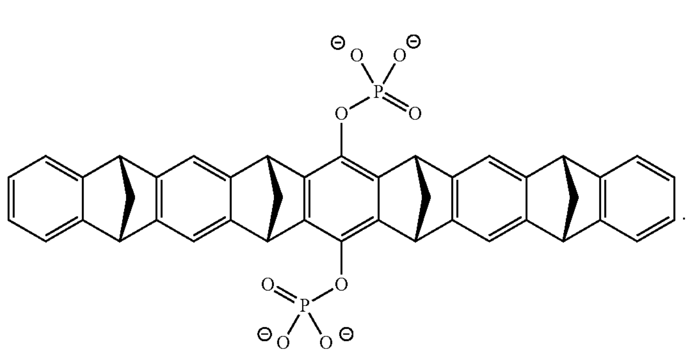

Embodiment 151: The pharmaceutical formulation or molecular tweezers of embodiment 141, wherein said molecular tweezers comprises a compound according to the formula:

(TW2)

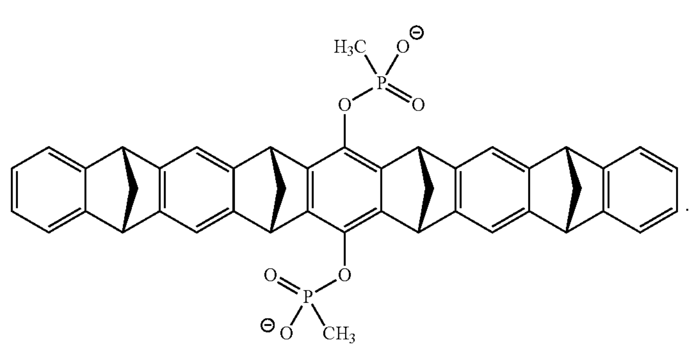

Embodiment 152: The pharmaceutical formulation or molecular tweezers of embodiment 141, wherein said molecular tweezers comprises a compound according to the formula:

(TW4)

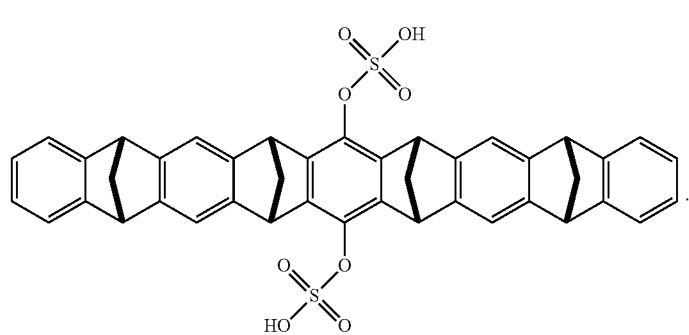

Embodiment 153: The pharmaceutical formulation or molecular tweezers of embodiment 141, wherein said molecular tweezers comprises a compound according to the formula:

(TW5)

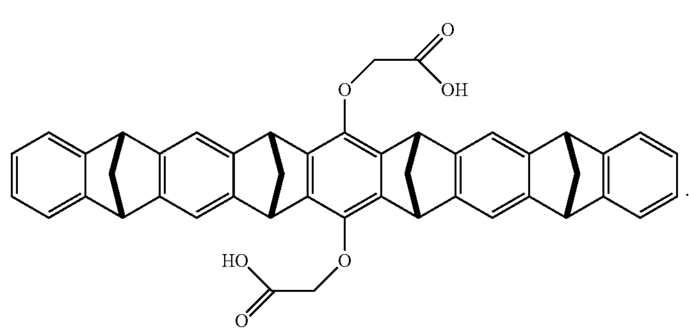

Embodiment 154: The pharmaceutical formulation or molecular tweezers according to any one of embodiments 84-153, wherein treatment comprises administration of said molecular tweezers to said mammal via a route selected from the group consisting of oral delivery, isophoretic delivery, transdermal delivery, parenteral delivery, aerosol administration, administration via inhalation, intravenous administration, ocular administration, depot delivery, vaginal administration, and rectal administration.

Embodiment 155: The pharmaceutical formulation or molecular tweezers according to any one of embodiments 83-153, wherein treatment comprises parenteral administration.

Embodiment 156: The pharmaceutical formulation or molecular tweezers of embodiment 155, wherein said administration is selected from a route selected from the group consisting of intraspinal administration, intrathecal or epidural administration, sub dural administration, subcutaneous administration, intravenous administration, administration through a subcutaneously implanted device, and administration is through a cannula.

Embodiment 157: The pharmaceutical formulation or molecular tweezers according to any one of embodiments 83-156, wherein said mammal is a human.

Embodiment 158: The pharmaceutical formulation or molecular tweezers according to any one of embodiments 83-156, wherein said mammal is non-human mammal.

Embodiment 159: The pharmaceutical formulation or molecular tweezers according to any one of embodiments 83-158, wherein said treatment is used in combination with enzyme replacement therapy and/or gene therapy.

Embodiment 160: The pharmaceutical formulation or molecular tweezers of embodiment 159, wherein treatment is used in combination with a gene therapy selected form the group consisting of a lentivirus-mediated gene therapy, and AAV-mediated gene therapy, and gene editing (e.g., CRISPR) therapy.

In certain embodiments the molecular tweezers used in the methods provided herein expressly exclude TW3. In certain embodiments, the subjects treated using the methods described herein are not diagnosed with and/or under treatment for a pathology characterized by aggregation of a protein selected from the group consisting of Aβ, tau, and α-synuclein. In certain embodiments, the subjects treated using the methods described herein are not diagnosed with and/or under treatment for a condition selected from the group consisting of Alzheimer's disease, amyloid mediated mild cognitive impairment (MCI), brain or spinal cord injury (including, but not limited to stroke), Huntingtin's Disease, and Parkinson's disease.

Definitions

Molecular tweezers, are host molecules with open cavities capable of binding guest molecules (see, e.g., Hardouin-Lerouge et al. (2011) *Chem. Soc. Rev.* 40: 30-43). The open cavity of the molecular tweezers may bind guests using non-covalent bonding which can include one or more of hydrogen bonding, metal coordination, hydrophobic forces, van der Waals forces, π-π interactions, and/or electrostatic effects. These complexes can be viewed as a subset of macrocyclic molecular receptors and their typical structure is characterized by two "arms" that bind the guest molecule between them and are only connected at one end leading to a certain flexibility of these molecules (induced fit model).

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from a lysosomal storage disorder or is at a risk of suffering a lysosomal storage disorder (e.g., as indicated by a genetic and/or metabolic marker).

The terms "treatment," "treating," or "treat" as used herein, refer to actions that produce a desirable effect on the symptoms or pathology of a lysosomal storage disease as described herein, and may include, but are not limited to, even minimal changes or improvements in one or more symptoms and/or one or more measurable markers of the disease or condition being treated. "Treatment," "treating," or "treat" does not necessarily indicate complete eradication or cure of the disease or condition, or associated symptoms thereof. In one embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

An "effective amount" refers to an amount effective, at dosages and for periods of time necessary, to achieve the desired therapeutic or prophylactic result. A "therapeutically effective amount" of molecular tweezers or formulations thereof described herein may vary according to factors such as the specific disease, disease state, age, sex, and weight of the individual, and the ability of the treatment to elicit a desired response in the individual. A therapeutically effective amount is also one in which any toxic or detrimental effects of a treatment are substantially absent or are outweighed by the therapeutically beneficial effects. The term "therapeutically effective amount" refers to an amount of one or more molecular tweezers described herein or composition comprising the same that is effective to "treat" a lysosomal storage disorder in a mammal (e.g., a patient). In one embodiment, a therapeutically effective amount is an amount sufficient to improve at least one symptom associated with a lysosomal storage disorder.

A "prophylactically effective amount" refers to an amount effective, at dosages and for periods of time necessary, to achieve the desired prophylactic result, e.g., to slow or stop the onset of the disease or to slow or stop the onset of one or more symptoms of the disease. Typically, a prophylactic dose is administered prior to presentation of symptoms of the disease.

The term "mitigating" or "ameliorating" when used with respect to symptoms, refers to reduction or elimination of one or more symptoms of that pathology.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

DETAILED DESCRIPTION

Figure 1:
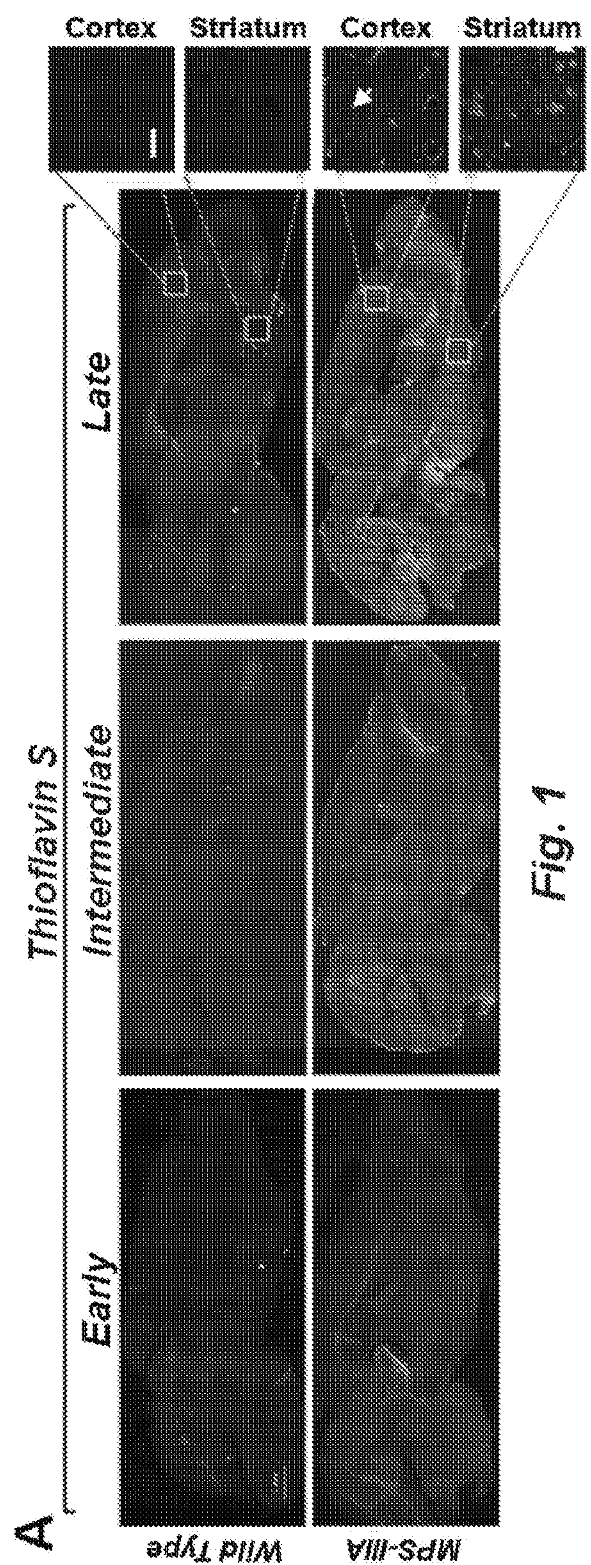
FIG. 1, panels A-G, illustrates the evaluation of the presence of amyloid proteins aggregation in different brain regions of MPSIIIA mice. Panel A) Scan of brain sagittal sections of MPS-IIIA and Wild Type mice stained with Thioflavin S at 3 different time points: early (3 months), intermediate (6 months) and Late (10 months). On the right are highlighted, only for the late time point, the cortex and ventral striatum areas with them typical staining pattern. Panel B) Graphical representation of fluorescence emission at 495 nm obtained by the quantitative assay performed on 3 brain homogenates for each experimental class with Thioflavin T. Panel C) co-Immunofluorescence analysis of Thioflavin S with different cell markers was performed on sagittal brain sections of MPSIIIA mice at late time point. Arrows indicate thioS positive structures in cells stained for the correspondent cell marker. Panel D) Confocal analysis of Thioflavin S (in green) and markers of cellular organelles (in red) stained by Immunofluorescence performed on sagittal brain sections of MPS-IIIA mice at late time point. Panel E) Confocal Super Resolution Image of Lamp-1 (in red) and Thioflavin S (in green) staining of MPSIIIA mice brain sections at late time point (in the yellow box the Thioflavin S structures inside the lysosomes). Panel F) Alpha synuclein immunohistochemistry experiments performed on wild type and MPS-IIIA mice brain at late time point either without proteinase K treatment (zoom of the MPSIIIA areas on the right) or with proteinase K treatment (zoom of the MPS-IIIA areas on the right). The positive elements in perikaryon are indicated by arrows while spheroids by arrowheads. Panel G) Confocal analysis of Thioflavin S and alpha synuclein in MPS-IIIA and Wild Type mice brain at late time point.

Lysosomal storage diseases, and in particular neurological lysosomal storage diseases (LSDs), are genetic disorders with a complex pathology characterized by lysosomal dysfunction. Increasing evidence shows that reduced lysosomal degradation capability in LSDs impairs protein homeostasis, thus driving neurodegenerative processes by mechanisms that are, however, poorly understood. Recently the inventors found that α-synuclein accumulates at perikarya of nerve cells in several LSD models, thus contributing to neurodegeneration by a loss-of-function mechanism. As described herein, the α-synuclein aggregates are part of amyloid deposits that may also exert a gain-of-toxic function through the worsening of lysosomal pathology.

Additionally, the inventors found that amyloid deposition is, indeed, a general feature of LSD brain pathology. Such amyloid inclusions contain α-synuclein together with other amyloidogenic proteins, such as prion protein, Tau, amyloid β-peptide and prion protein. A major fraction of these amyloids builds-up within the lysosomal compartment where they exacerbate lysosomal enlargement and dysfunction, thus boosting the development of neurodegenerative phenotype. As demonstrated herein, inhibiting amyloid deposition in a mouse model of a severe neurodegenerative LSD relieves lysosomal pathology, thus improving lysosomal degradation and ameliorating neuropathological signs.

Together, these data shed new light on the mechanisms underlying lysosomal brain diseases, thus identifying LSDs as a new class of amyloid disorders and opening new therapeutic options for their treatment.

Additionally, it was a surprising discovery that molecular tweezers, such as those described in PCT Publication No: WO2010102248, are capable of attenuating neuronal loss and reducing inflammation in LSDs, thus providing a novel treatment for LSDs and in particular for LSDs with neurological impairment.

Accordingly, in various embodiments, methods for the treatment or prophylaxis of lysosomal storage diseases are provided. In certain embodiments the methods involve administering a therapeutically effective amount and/or a prophylactically effective amount of one or more molecular tweezers to a subject (e.g., a human or a non-human mammal) in need thereof. In certain embodiments the subject "in need thereof" comprises a subject diagnosed with a lysosomal storage disease (e.g., a symptomatic subject) or a subject determined to be "at risk" for a lysosomal storage disease (e.g., an asymptomatic subject identified with one or more genetic markers or biochemical markers of a lysosomal storage disease). Typically, the molecular tweezers will be a molecular tweezers that inhibits protein aggregation. In certain embodiments the molecular tweezers can be a molecular tweezers that inhibits aggregation of an amyloid protein (e.g., one or more proteins selected from the group consisting of α-synuclein, Aβ, and tau).

In certain embodiments administration of the molecular tweezers is effective to slow the progression, or stop, or reverse accumulation/aggregation associated with said lysosomal storage disease. In certain embodiments the administration of the molecular tweezers is therapeutic and is effective to ameliorate one or more symptoms of the pathology associated with the lysosomal storage disease. In certain embodiments the administration of the molecular tweezers is therapeutic and is effective to slow, or to stop, or to reverse progression of a pathology associated with the lysosomal storage disease. In certain embodiments administration of the molecular tweezers is prophylactic and is effective to delay or stop the onset of the lysosomal storage disease or to delay or stop the onset of one or more symptoms of a lysosomal storage disease.

Molecular Tweezers for the Treatment and/or Prophylaxis of Lysosomal Storage Diseases.

In various embodiments molecular tweezer(s) useful in the methods described herein may be capable of inhibiting and/or modulating aggregation of one or more proteins, and/or promoting disaggregation of protein fibrils or other protein aggregates, or both. In certain embodiments the molecular tweezers are capable of inhibiting and/or modulating aggregation of one or more amyloidogenic proteins (e.g., one or more of α-synuclein, Aβ, tau, and the like), and/or promoting disaggregation of amyloid protein fibrils or other amyloid protein aggregates, or both.

In certain illustrative, but non-limiting embodiments, treatment of subjects with lysosomal storage diseases with molecular tweezers may improve survival of neurons, and/or regeneration of neurons, and/or other outcomes in cells that are likely to die as a result of the lysosomal storage disease. Distinct cell types or groups of cells may respond to treatment with molecular tweezers with varying efficacy or varying responses. Treatment outcomes may also be observed at the systemic or organism level, including some aspects of functional recovery.

Examples of molecular tweezers are known in the art, e.g., in International Publication Number WO 2010/102248 (also published as US 2012/0108548), which is herein incorporated by reference in its entirety and, in particular for the molecular tweezers described therein (see, especially Table 2 therein).

Illustrative molecular tweezers useful in the methods described herein may be a molecular tweezers according to any one of Formulas I, II, III, and IV:

(I)

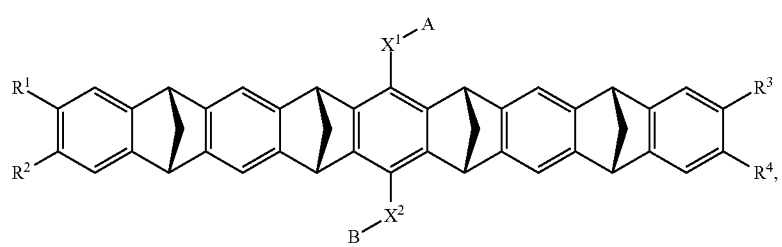

-continued (II)

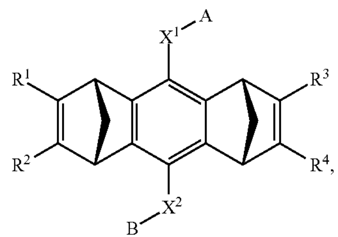

(III)

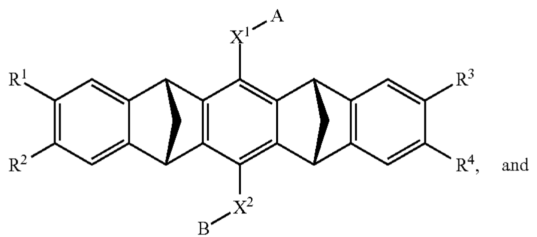

(IV)

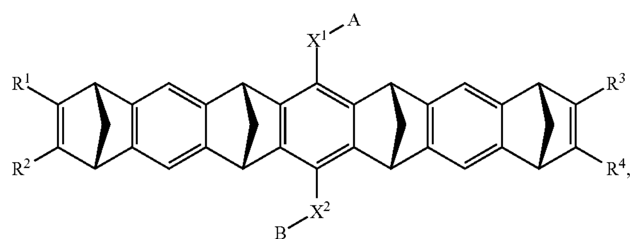

or a pharmaceutically acceptable salt, ester, amide, clathrate, or prodrug thereof, where: $X^1$ and $X^2$ are both O; A alone, or A combined with $X^1$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate, and

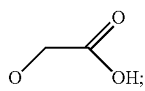

B alone, or B combined with $X^2$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate and

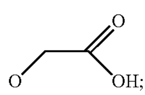

and each of $R^1$, $R^2$, $R^3$, and $R^4$ is, independently, selected from the group consisting of H, Cl, Br, I, OR, $NR_2$, $NO_2$, $CO_2H$, and $CO_2R^5$, wherein $R^5$ is alkyl, aryl or H, or $R^1$ and $R^2$ combine to form an aliphatic or aromatic ring, and/or $R^3$ and $R^4$ combine to form an aliphatic or aromatic ring.

In certain embodiments A and B are independently selected from the group consisting of

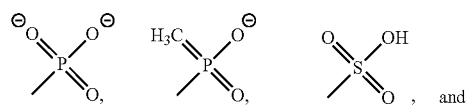

-continued

O OH.

In certain embodiments A and B are the same. In certain embodiments A and B are independently selected from the group consisting of

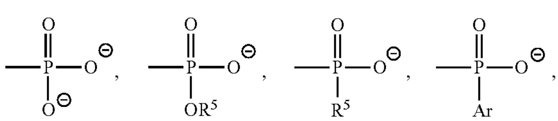

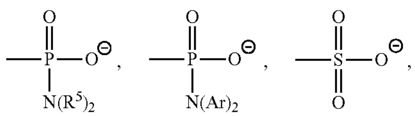

and —$(CH_2)_n$—$CO_2^-$, where $R^5$ is alkyl or H; n ranges from 1 to 10, and Ar is aryl.

In certain embodiments the molecular tweezers is a molecular tweezers according formula I or a pharmaceutically acceptable salt thereof. In certain embodiments the molecular tweezers is a molecular tweezers according formula II or a pharmaceutically acceptable salt thereof. In certain embodiments the molecular tweezers is a molecular tweezers according formula III or a pharmaceutically acceptable salt thereof. In certain embodiments the molecular tweezers according formula IV or a pharmaceutically acceptable salt thereof. In certain embodiments the molecular tweezers comprises a compound according to the formula:

(TW1/CLR01)
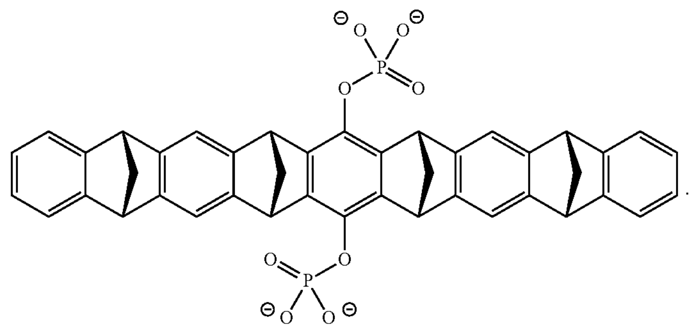
In certain embodiments the molecular tweezers comprises a compound according to the formula:
(TW2)
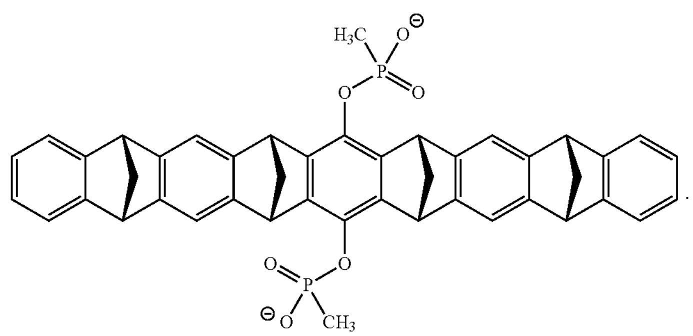
In certain embodiments the molecular tweezers comprises a compound according to the formula:
(TW4)
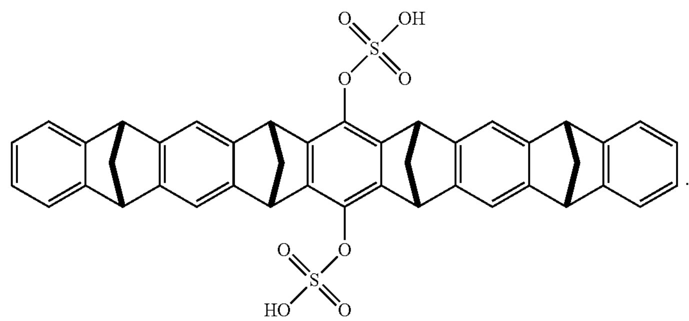

In certain embodiments the molecular tweezers comprises a compound according to the formula:

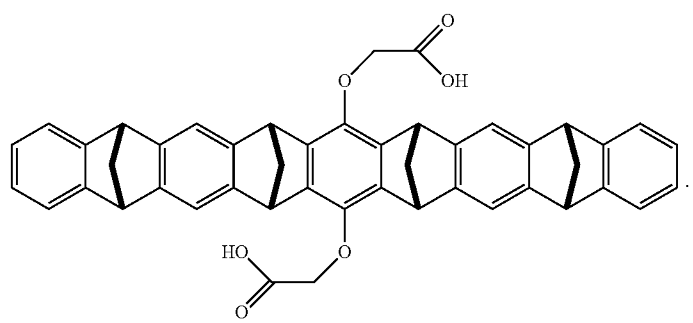

Other molecular tweezers are known in the art and using the teachings provided herein molecular tweezers well suited to use in the methods described herein will be readily available to one of skill in the art.

Synthesis of Molecular Tweezers

Molecular tweezers may be synthesized according to any of a number of methods known to those of skill in the art (see, e.g., Zimmerman et al. (1991) *J. Am. Chem. Soc.* 113: 183-196). The synthesis of molecular tweezers TW1 (i.e. CLR01), TW2, and TW3 is described below (see also PCT Application No: PCT/US2010/026419).

In one illustrative, but non-limiting embodiment, the skeleton of the tetramethylene-bridged molecular tweezers (the starting material of tweezers TW1 (i.e. CLR01) and TW2) can be constructed by repetitive Diels-Alder reactions of exo-5,6-bismethylene-2,3-benzonorbornene as diene with the bisnorbornadienobenzene as bisdieneophile. Subsequent oxidative dehydrogenation of the cyclohexene rings in the (1:2) Diels-Alder cycloadduct with DDQ leads to the molecular tweezers (Klarner et al. (1999) *Chem. Eur. J.* 5:1700-1707; Klarner et al. (2001) *Tetrahedron,* 57: 3573-3687; Klarner et al. (2004) *Eur. J. Org. Chem.* 7: 1405-1423; Klarner et al. (2008) Synthesis of molecular tweezers and clips by the use of a molecular Lego set and their supramolecular functions, Chapter 4:99-153, in Strategies and Tactics in Organic Synthesis, Vol. 7 (ed. Harmata, M.), Academic Press, Elsevier, Amsterdam).

The skeleton of the related dimethylene-bridged molecular clips can be synthesized by repetitive Diels-Alder reactions analogously to the synthesis of the tweezers using dibromo-o-quinodimethane derivatives as diene and the same bisdienophile. In this case the HBr elimination in the (1:2) Diels-Alder cycloadduct occurs under the condition of formation leading to the molecular clips in a one-pot reaction.

In one illustrative embodiment, the bisdienophile is the starting material for the synthesis of the tweezers of type TW3. Their preparation starts with a one-pot reaction producing the norbornadienoquinone. The Diels-Alder cycloaddition of 1,3-cyclopentadiene to p-benzoquinone leads to the known (1:1) adduct which isomerizes in the presence of triethylamine to the corresponding hydroquinone that is subsequently oxidized with an excess of p-benzoquinone. The resulting quinone readily reacts with 1,3-cyclopentadiene at −78° C. almost quantitatively leading to a (60:40) mixture of the syn- and anti-Diels-Alder adduct which can be easily separated by recrystallization from toluene. Under basic conditions in the presence of acetic anhydride the syn-adduct is converted to the corresponding diacetoxy-substituted bisdienophile, the starting material of TW3.

(TW5)

The tweezers TW1-3 substituted by methanephosphonate or phosphate groups in the central benzene ring were prepared by reductive or basic ester hydrolysis of the corresponding diacetoxy derivatives followed by esterification of the hydroquinones with $MePOCl_2$ and $POCl_3$, respectively. Hydrolysis and neutralization of the methanephsphonic acid or phosphoric acid derivatives with lithium hydroxide lead to the desired methanephosphonate or phosphate salts (Fokkens et al. (2005) *Chem. Eur. J.* 11: 477-494; Schrader et al. (2005) *J. Org. Chem.* 70:10227-10237; Talbiersky et al. (2008) *J. Am. Chem. Soc.* 130:9824-9828).

Synthesis of TW-2 is described in Fokkens et al. (2005) *J. Am. Chem. Soc.* 27(41): 14415-14421, while the synthesis of various other molecular tweezers (including truncation variants) is described in Klarner et al. (2006) *J. Am. Chem. Soc.* 128(14): 4831-4841. The methods described therein can readily be modified to synthesize other molecular tweezers. These methods may be readily adapted or modified to prepare other molecular tweezers of the present invention.

Formulation and Administration of Molecular Tweezers

In some instances, delivery of a naked, i.e. native form, molecular tweezers may be sufficient to inhibit aggregation of a target protein in a cell. In various embodiments, a molecular tweezers may be administered in the form of a salt, ester, amide, clathrate, derivative, and the like, provided the salt, ester, amide, clathrate, or derivative is pharmacologically effective (e.g., capable of inhibiting a protein aggregation (e.g., in certain embodiments, inhibiting aggregation of one or more of α-synuclein, Aβ, and/or Tau). In certain embodiments a prodrug or other adduct or derivative of a molecular tweezers described herein which upon administration to a subject in need is capable of providing, directly or indirectly, the molecular tweezers can be utilized.

In certain embodiments pharmaceutical compositions are provided, that comprise any one or more of the molecular tweezers described herein (or a prodrug, pharmaceutically acceptable salt, pharmaceutically acceptable ester, pharmaceutically acceptable amide, prodrug, or other pharmaceutically acceptable derivative thereof), and optionally comprise a pharmaceutically acceptable carrier. In certain embodiments, these compositions optionally further comprise one or more additional therapeutic agents. In certain embodiments a molecular tweezers described herein may be administered to a patient in need thereof in combination with the administration of one or more other therapeutic agents. For example, additional therapeutic agents for conjoint administration or inclusion in a pharmaceutical composition with a molecular tweezers described herein may be an approved agent to treat the same or related indication, or it may be any one of a number of agents undergoing approval in the Food and Drug Administration for a disorder related to an lysosomal storage disease.

Salts, esters, amides, clathrates, prodrugs and other derivatives of a molecular tweezers can be prepared using standard procedures known in the art of synthetic organic chemistry. For example, in certain embodiments, a pharmaceutically acceptable salt form of the molecular tweezers is contemplated. As used herein, the term "pharmaceutically acceptable salt" refers to those salts that are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, Berge, et al. (1977) *J. Pharmaceutical Sciences,* 66: 1-19, describe pharmaceutically acceptable salts in detail. The salts can be prepared in situ during the final isolation and purification of the active agents (e.g., molecular tweezers), or separately by reacting a free base or free acid function with a suitable reagent, as described generally below. For example, a free base function can be reacted with a suitable acid or a free acid function can be reacted with a suitable free base. Furthermore, where the compounds (such as the molecular tweezers) are or carry an acidic moiety, suitable pharmaceutically acceptable salts thereof may, include metal salts such as alkali metal salts, e.g. sodium, potassium, or copper salts; ammonium hydroxide, calcium hydroxide, trimethylamine, and the like; and alkaline earth metal salts, e.g. calcium or magnesium salts.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

In certain embodiments, the compounds described herein can be formulated as "pharmaceutically acceptable esters". In certain embodiments suitable esters include, but are not limited to, esters that hydrolyze in vivo and include those that break down readily in the human body to leave the parent compound or a salt thereof. Suitable ester groups include, but are not limited to, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Preparation of esters may involve functionalization of, e.g., hydroxyl and/or carboxyl groups that are present within the molecular structure of a molecular tweezers. In certain embodiments, the esters are acyl-substituted derivatives of free alcohol groups, i.e., moieties derived from carboxylic acids of the formula RCOOH where R is alky, and preferably is lower alkyl. Esters may be reconverted to the free acids, if desired, by using conventional hydrogenolysis or hydrolysis procedures.

Amides may also be prepared using techniques known in the art. For example, an amide may be prepared from an ester using suitable amine reactants, or prepared from an anhydride or an acid chloride by reaction with ammonia or a lower alkyl amine.

In various embodiments any one or more of the molecular tweezers described herein may be combined with a pharmaceutically acceptable carrier (excipient) to form a pharmacological composition (pharmaceutical formulation). Certain pharmaceutically acceptable carriers can contain one or more physiologically acceptable compound(s) that act, e.g., to stabilize the composition, increase or decrease the absorption of the molecular tweezers, or improve penetration of the blood brain barrier (where appropriate). Physiologically acceptable compounds may include, e.g., carbohydrates (e.g., glucose, sucrose, or dextrans), antioxidants (e.g. ascorbic acid or glutathione), chelating agents, low molecular weight proteins, protection and uptake enhancers (e.g., lipids), compositions that reduce the clearance or hydrolysis of the active agents, or excipients or other stabilizers and/or buffers. Other physiologically acceptable compounds, particularly of use in the preparation of tablets, capsules, gel caps, and the like include, but are not limited to binders, diluents/fillers, disintegrants, lubricants, suspending agents, and the like. In certain embodiments, a pharmaceutical formulation may enhance delivery or efficacy of a molecular tweezers.

In various embodiments, a molecular tweezers described herein may be prepared for parenteral, topical, oral, nasal (or otherwise inhaled), rectal, or local administration. Administration may occur, for example, transdermally, or by aerosol.

A pharmaceutical composition comprising one or more molecular tweezers described herein may be administered in a variety of unit dosage forms depending upon the method of administration. Suitable unit dosage forms, include, but are not limited to, powders, tablets, pills, capsules, lozenges, suppositories, patches, nasal sprays, injectables, implantable sustained-release formulations, and lipid complexes.

In certain embodiments, an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), or an optional lubricant (e.g., talc, magnesium stearate, polyethylene glycol 6000, etc.), may be added to a molecular tweezers and the resulting composition may be compressed to manufacture an oral dosage form (e.g., a tablet). In particular embodiments, a compressed product may be coated, e.g., to mask the taste of the compressed product, to promote enteric dissolution of the compressed product, or to promote sustained release of the molecular tweezers. Suitable coating materials include, but are not limited to, ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds that may be included a pharmaceutical composition comprising one or more molecular tweezers may include wetting agents, emulsifying agents, dispersing agents or preservatives that are particularly useful for preventing the growth or action of microorganisms. Various preservatives are well known and include, for example, phenol and ascorbic acid. The choice of pharmaceutically acceptable carrier(s), including a physiologically acceptable compound, depends, e.g., on the route of administration of the molecular tweezers and on the particular physio-chemical characteristics of the molecular tweezers.

In certain embodiments, one or more excipients for use in a pharmaceutical composition including one or more molecular tweezers may be sterile and/or substantially free of undesirable matter. Such compositions may be sterilized by conventional techniques known in the art. For various oral dosage form excipients, such as tablets and capsules, sterility is not required. Standards are known in the art, e.g., the USP/NF standard.

A pharmaceutical composition comprising one or more molecular tweezers as described herein may be administered in a single or in multiple administrations depending on the dosage, the required frequency of administration, and the known or anticipated tolerance of the subject for the pharmaceutical composition with respect to dosages and frequency of administration. In various embodiments, the composition may provide a sufficient quantity of a molecular tweezers to effectively treat (ameliorate one or more symptoms of) lysosomal storage disease in the subject (e.g., decrease cellular impairment or cell death (e.g., neurodegeneration and/or neuroinflammation), improve neuronal activities).

In some embodiments, the molecular tweezers is administered to a subject (e.g., a human or a non-human mammal) diagnosed with a lysosomal storage disease. In certain embodiments such a subject is exhibiting one or more symptoms of a lysosomal storage disease. In certain embodiments the molecular tweezers is administered to a subject that is asymptomatic, but identified as being "at risk" for a lysosomal storage disease (e.g., a subject with one or more genetic or metabolic markers of a lysosomal storage disease). In certain embodiments the molecular tweezers is administered to an infant. In certain embodiments the molecular tweezers is administered to a subject before the appearance of symptoms of a lysosomal storage disease (e.g., in the case of humans within 3 months of birth, or within 6 months of birth, or within 1 year of birth, or within 2 years of birth, or within 3 years of birth, or within 4 years of birth, or within 5 years of birth, or within 6 years of birth, or before adolescence, etc., depending on the lysosomal storage disease being treated).

The amount and/or concentration of molecular tweezers to be administered to a subject may vary widely, and will typically be selected primarily based on activity of the molecular tweezers and the characteristics of the subject, e.g., species and body weight, as well as the particular mode of administration and the needs of the subject. In certain embodiments, the dosage of molecular tweezers may be 0.001 to about 50 or more mg/kg/day. For example, the dosage of a molecular tweezers may be about 0.001, 0.01, 0.1, 1, 5, 10, 20, 30, 40, or 50 or more mg/kg/day. In certain embodiments typical dosages range from about 1 mg/kg/day to about 3 mg/kg/day, from about 3 mg/kg/day to about 10 mg/kg/day, from about 10 mg/kg/day to about 20.0 mg/kg/day, or from about 20 mg/kg/day to about 50 mg/kg/day. In certain embodiments, dosages range from about 10 mg/kg/day to about 50 mg/kg/day. In certain embodiments, dosages range from about 20 mg to about 50 mg given orally twice daily. Dosages may be varied to optimize a therapeutic and/or prophylactic regimen in a particular subject or group of subjects.

In certain embodiments, a molecular tweezers is administered to the oral cavity, e.g., by the use of a lozenge, aerosol spray, mouthwash, coated swab, or other mechanism known in the art.

In certain embodiments a molecular tweezers may be administered systemically (e.g., orally, or as an injectable) in accordance with standard methods known in the art. In certain embodiments, the molecular tweezers may be delivered through the skin using a transdermal drug delivery systems, i.e., transdermal "patches," wherein the molecular tweezers are typically contained within a laminated structure that serves as a drug delivery device to be affixed to the skin. In such a structure, the drug composition is typically contained in a layer, or reservoir, underlying an upper backing layer. The reservoir of a transdermal patch includes a quantity of molecular tweezers that is ultimately available for delivery to the surface of the skin. Thus, the reservoir may include, e.g., the molecular tweezers of the present invention in an adhesive on a backing layer of the patch, or in any of a variety of different matrix formulations known in the art. The patch may contain a single reservoir or multiple reservoirs.

In one illustrative, but non-limiting, transdermal patch embodiment, a reservoir may comprise a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, and polyurethanes. Alternatively, the molecular tweezers-containing reservoir and skin contact adhesive are present as separate and distinct layers, with the adhesive underlying the reservoir which, in this case, may be either a polymeric matrix as described above, a liquid or hydrogel reservoir, or another form of reservoir known in the art. The backing layer in these laminates, which serves as the upper surface of the device, preferably functions as a primary structural element of the patch and provides the device with a substantial portion of flexibility. The material selected for the backing layer is preferably substantially impermeable to the molecular tweezers and to any other materials that are present.

Additional formulations for topical delivery include, but are not limited to, ointments, gels, sprays, fluids, and creams. Ointments are semisolid preparations that are typically based on petrolatum or other petroleum derivatives. Creams including a molecular tweezers are typically viscous liquids or semisolid emulsions, e.g. oil-in-water or water-in-oil emulsions. Cream bases are typically water-washable and include an oil phase, an emulsifier, and an aqueous phase. The oil phase, also sometimes called the "internal" phase, of a cream base is generally comprised of petrolatum and a fatty alcohol, e.g. cetyl alcohol or stearyl alcohol; the aqueous phase usually, although not necessarily, exceeds the oil phase in volume, and generally contains a humectant. The emulsifier in a cream formulation is generally a nonionic, anionic, cationic, or amphoteric surfactant. The specific ointment or cream base to be used may be selected to provide for optimum drug delivery according to the art. As with other carriers or vehicles, an ointment base may be inert, stable, non-irritating, and non-sensitizing.

Various buccal and sublingual formulations are also contemplated.

In certain embodiments, administration of a molecular tweezers may be parenteral. Parenteral administration may include, for example, intraspinal, intrathecal, epidural, subdural, subcutaneous, or intravenous administration. Means of parenteral administration are known in the art. In particular embodiments, parenteral administration may include a subcutaneously implanted device.

In certain embodiments, it may be desirable to deliver the molecular tweezers to the brain and/or central nervous system (CNS). In certain embodiments involving system administration, this could require that the molecular tweezers cross the blood brain barrier. In various embodiments this may be facilitated by co-administering a molecular tweezers with carrier molecules such as cationic dendrimers or arginine-rich peptides, that may carry a molecular tweezers over the blood brain barrier.

In certain embodiments a molecular tweezers may be delivered directly to the brain by administration through the implantation of a biocompatible release system (e.g., a reservoir), by direct administration through an implanted cannula, by administration through an implanted or partially implanted drug pump, or mechanisms of similar function known the art. In certain embodiments, a molecular tweezers may be systemically administered (e.g., injected into a vein). In certain embodiments it is expected that the molecular tweezers will be transported across the blood brain barrier without the use of additional compounds included in a pharmaceutical composition to enhance transport across the blood brain barrier.

In certain embodiments, one or more molecular tweezers may be provided as a concentrate, e.g., in a storage container or soluble capsule ready for dilution or addition to a volume of water, alcohol, hydrogen peroxide, or other diluent. A concentrate may designed to provide a particular amount of molecular tweezers and/or a particular total volume. The concentrate may be formulated for dilution in a particular volume of diluents prior to administration.

Other suitable formulations and modes of administration are known or may be derived from the art.

A molecular tweezers of the present invention may be administered to a mammal in need thereof, such as a mammal diagnosed as having or at risk for a lysosomal storage disease. In certain embodiments a molecular tweezers may be administered to inhibit aggregation of one or more proteins (e.g., one or more amyloidogenic proteins such as α-synuclein, Aβ, and/or Tau). A molecular tweezers of the present invention may be administered to mitigate one or more symptoms of a lysosomal storage disease.

A therapeutically effective dose of a pharmaceutical composition of the present invention may depend upon the age of the subject, the gender of the subject, the species of the subject, the particular pathology, the severity of the symptoms, and the general state of the subject's health.

The pharmaceutical compositions described herein may be suitable for administration to an animal, e.g., for veterinary use. Certain embodiments of the methods described herein may include administration of a pharmaceutical composition of the present invention to a non-human organisms, e.g., non-human mammals such as a non-human primates, canine, equine, feline, porcine, ungulate, lagomorphs, or other vertebrates. In various embodiments the pharmaceutical compositions are suitable for administration to a human.

Lysosomal storage diseases for treatment of with a molecular tweezers.

In various embodiments molecular tweezers are administered to a subject (e.g., to a mammal in need thereof) one or molecular tweezers for the treatment or prophylaxis of a lysosomal storage disease (LSD). In certain embodiments the lysosomal storage disease comprises an LSD with neuropathological implications and consequent neurological impairment.

Lysosomal storage diseases (LSDs) are a group of about 70 inherited metabolic disorders that result from defects in lysosomal function. Lysosomes are intracellular compartments that contain enzymes that digest large molecules and pass the fragments on to other parts of the cell for recycling. This process requires several critical enzymes and if one or more of these enzymes is defective, e.g., because of a mutation, the large molecules accumulate within the cell, eventually killing it.

Lysosomal storage disorders are caused by lysosomal dysfunction usually as a consequence of deficiency of a single enzyme required for the metabolism of lipids, glycoproteins, or so-called mucopolysaccharides. Individually, LSDs occur with incidences of less than 1:100,000; however, as a group, the incidence is about 1:5,000-1:10,000 (see, e.g., Meikle et al. (1999) *JAMA,* 281(3): 249-254). Most of these disorders are autosomal recessively inherited such as Niemann-Pick disease, type C, but a few are X-linked recessively inherited, such as Fabry disease and Hunter syndrome (MPS II).

Lysosomal disorders are usually triggered when a particular lysosome enzyme exists in too small an amount or is missing altogether. When this happens excess products destined for breakdown and recycling are stored in the cell.

Like other genetic disorders, individuals inherit lysosomal storage diseases from their parents. Although each disorder results from different gene mutations that translate into a deficiency in enzyme activity, they all share a common biochemical characteristic—all lysosomal disorders originate from an abnormal accumulation of substances inside the lysosome.

LSDs affect mostly children and they often die at a young and unpredictable age, many within a few months or years of birth. Many other children die of this disease following years of suffering from various symptoms of their particular disorder.

The LSDs are generally classified by the nature of the primary stored material involved, and can be broadly broken into the following: 1) Lipid storage disorders, mainly sphingolipidoses (including Gaucher's and Niemann-Pick diseases); 2) Gangliosidosis (including Tay-Sachs disease; 3) Leukodystrophies; 4) Mucopolysaccharidoses (including Hunter syndrome and Hurler disease); 5) glycoprotein storage disorders; and 6) mucolipidoses.

In certain embodiments lysosomal storage diseases include but are not limited to, Sphingolipidoses, Ceramidase (e.g., Farber disease, Krabbe disease), Galactosialidosis, gangliosidoses including Alpha-galactosidases (e.g., Fabry disease (alpha-galactosidase A), Schindler disease (alpha-galactosidase B)), Beta-galactosidase (e.g., GM1 gangliosidosis, GM2 gangliosidosis, Sandhoff disease, Tay-Sachs disease), Glucocerebrosidoses (e.g., Gaucher disease (Type I, Type II, Type III), Sphingomyelinase (e.g., Lysosomal acid lipase deficiency, Niemann-Pick disease), Sulfatidosis (e.g., Metachromatic leukodystrophy. Multiple sulfatase deficiency), Mucopolysaccharidoses (e.g., Type I (MPS I (Hurler syndrome, MPS I S Scheie syndrome, MPS I H-S Hurler-Scheie syndrome), Type II (Hunter syndrome), Type III (Sanfilippo syndrome), Type IV (Morquio), Type VI (Maroteaux-Lamy syndrome), Type VII (Sly syndrome), Type IX (hyaluronidase deficiency)), mucolipidoses (e.g., Type I (sialidosis), Type II (I-cell disease), Type III (pseudo-Hurler polydystrophy/phosphotransferase deficiency), Type IV (mucolipidin 1 deficiency)), lipidoses (e.g., Niemann-Pick disease), Neuronal ceroid lipofuscinoses (e.g., Type 1 Santavuori-Haltia disease/infantile NCL (CLN1 PPT1)), Type 2 Jansky-Bielschowsky disease/late infantile NCL (CLN2/LINCL TPP1), Type 3 Batten-Spielmeyer-Vogt disease/juvenile NCL (CLN3), Type 4 Kufs disease/adult NCL (CLN4), Type 5 Finnish Variant/late infantile (CLN5), Type 6 Late infantile variant (CLN6), Type 7 CLN7, Type 8 Northern epilepsy (CLN8), Type 8 Turkish late infantile (CLN8), Type 9 German/Serbian late infantile, Type 10 Congenital cathepsin D deficiency (CTSD)), Wolman disease, Oligosaccharidoses (e.g., Alpha-mannosidosis, Beta-mannosidosis, Aspartylglucosaminuria, Fucosidosis), lysosomal transport diseases (e.g., Cystinosis, Pycnodysostosis, Salla disease/sialic acid storage disease, Infantile free sialic acid storage disease), Glycogen storage diseases, e.g., Type II Pompe disease, Type IIb Danon disease), Cholesteryl ester storage disease, and the like.

Illustrative lysosomal storage diseases that can be treated using the molecular tweezers described herein include, but are not limited to a mucopolysaccharidosis (MPS), aspartylglucosaminuria, GM1-gangliosidosis, Krabbe (globoid cell leukodystrophy or galactosylceramide lipidosis), Metachromatic leukodystrophy, Sandhoff disease, mucolipidosis type II (I-cell disease), mucolipidosis type IIIA (pseudo-Hurler polydystrophy), Niemann-Pick disease type C2 and C1, Danon disease, free sialic acid storage disorder, mucolipidosis type IV, and multiple sulfatase deficiency (MSD).

In certain embodiments the lysosomal storage disease comprises a mucopolysaccharidosis selected from the group consisting of Sanfilippo syndrome (MPS III), Hurler syndrome (MPS IH), Hurler-Scheie syndrome (MPS I-H/S), Scheie syndrome (MPS IS), Hunter syndrome (MPS II), Morquio syndrome (MP IV), Maroteaux-Lamy syndrome (MPS VI), Sly syndrome (MPS VII), and MPS IX.

Sanfilippo Syndrome (MPS III)

Mucopolysaccharidosis type III (MPS III), is characterized by severe and rapid intellectual deterioration. Deficiencies in one of the four enzymes required for heparan sulfate (HS) degradation are responsible for each of the MPS III subtypes: heparan sulfamidase for MPS IIIA, alpha-N-acetylglucosaminidase for MPS IIIB, alpha-glucosaminide N-acetyltransferase for MPS IIIC, and N-acetylglucosamine-6-sulfate sulfatase for MPS IIID. The clinical features of MPS III include, but are not limited to severe mental defects with relatively mild somatic features (moderately severe claw hand and visceromegaly, little or no corneal clouding or skeletal, e.g., vertebral, change). The first symptoms typically appear between the ages of 2 and 6 years, with behavioral disorders (hyperkinesia, aggressiveness) and intellectual deterioration, sleep disorders and very mild dysmorphism. The neurological involvement becomes more prominent around 10 years of age with loss of motor milestones and communication problems. Seizures often occur after the age of 10. A few cases of attenuated forms have also been reported. The prognosis is poor with death occurring in most cases of type IIIA at the end of the second decade. Longer survival times (30/40 years) have been reported for the B and D subtypes.

Diagnosis of MPS III is based on detection of increased levels of heparan sulfate (HS) in urine. Demonstration of one of the four enzyme deficiencies in cultivated leukocytes or fibroblasts allows determination of the type of MPS III. For types IIIA and IIID, the measurement of the activity of another sulfatase is compulsory for exclusion of multiple sulfatase deficiency (MSD or Austin disease).

In certain embodiments the prophylactic and/or therapeutic methods described herein involve ameliorating one or more of the above symptoms, e.g., one or more symptoms selected from the group consisting of cognitive deficiencies, claw hand, visceromegaly, sleep disorders, loss of motor function, loss of communication abilities, and seizures) and/or delaying the onset, slowing, stopping, or reversing the progression of one or more of these symptoms.

Hurler Syndrome (MPS I)

Hurler syndrome, also known as mucopolysaccharidosis type I (MPS I), Hurler's disease, also gargoylism, is a genetic disorder that results in the buildup of glycosaminoglycans (a.k.a. mucopolysaccharides) due to a deficiency of alpha-L iduronidase, an enzyme responsible for the degradation of mucopolysaccharides in lysosomes. Without this enzyme, a buildup of dermatan sulfate and heparan sulphate occurs in the body. Symptoms appear during childhood and early death can occur due to organ damage. MPS I is divided into three subtypes based on severity of symptoms. All three types result from an absence of, or insufficient levels of, the enzyme α-L-iduronidase. MPS I H or Hurler syndrome is the most severe of the MPS I subtypes. The other two types are MPS I S or Scheie syndrome and MPS I H-S or Hurler-Scheie syndrome.

Hurler syndrome is marked by progressive deterioration, hepatosplenomegaly, dwarfism, and unique facial features. A progressive mental retardation occurs, with death frequently occurring by the age of 10 years. Developmental delay is evident by the end of the first year, and patients usually stop developing between ages 2 and 4. This is followed by progressive mental decline and loss of physical skills. Language may be limited due to hearing loss and an enlarged tongue. In time, the clear layers of the cornea become clouded and retinas may begin to degenerate. Carpal tunnel syndrome (or similar compression of nerves elsewhere in the body) and restricted joint movement are common.

In certain embodiments the prophylactic and/or therapeutic methods described herein involve ameliorating one or more of the above symptoms Hunter Syndrome (MPS II)

Mucopolysaccharidosis type II (MPS II), also known as Hunter syndrome, is a condition that affects many different parts of the body and occurs almost exclusively in males. It is a progressively debilitating disorder.

At birth, individuals with MPS II typically do not display any features of the condition. Between ages 2 and 4, they develop full lips, large rounded cheeks, a broad nose, and an enlarged tongue (macroglossia). The vocal cords also enlarge, which results in a deep, hoarse voice. Narrowing of the airway causes frequent upper respiratory infections and short pauses in breathing during sleep (sleep apnea). As the disorder progresses, individuals need medical assistance to keep their airway open.

Individuals with this disorder often have a large head (macrocephaly), a buildup of fluid in the brain (hydrocephalus), an enlarged liver and spleen (hepatosplenomegaly). Most people with this disorder develop hearing loss and have recurrent ear infections. Some individuals with MPS II develop problems with the retina and have reduced vision. Carpal tunnel syndrome commonly occurs in children with this disorder and is characterized by numbness, tingling, and weakness in the hand and fingers. Narrowing of the spinal canal (spinal stenosis) in the neck can compress and damage the spinal cord. The heart is also significantly affected by MPS II, and many individuals develop heart valve problems.

In certain embodiments the prophylactic and/or therapeutic methods described herein involve ameliorating one or more of the above symptoms Mucopolysaccharidosis Type VII (MPS VII)

Mucopolysaccharidosis type VII (MPS VII), also known as Sly syndrome, is a progressive condition that affects most tissues and organs. The most severe cases of MPS VII are characterized by hydrops fetalis, a condition in which excess fluid builds up in the body before birth. Most babies with hydrops fetalis are stillborn or die soon after birth.

Other people with MPS VII typically begin to show signs and symptoms of the condition during early childhood. The features of MPS VII include a large head (macrocephaly), a buildup of fluid in the brain (hydrocephalus), distinctive-looking facial features that are described as "coarse," and a large tongue (macroglossia). Affected individuals also frequently develop an enlarged liver and spleen (hepatosplenomegaly), heart valve abnormalities, and a soft out-pouching around the belly-button (umbilical hernia) or lower abdomen (inguinal hernia). The airway may become narrow in some people with MPS VII, leading to frequent upper respiratory infections and short pauses in breathing during sleep (sleep apnea). The cornea becomes cloudy which can cause significant vision loss. People with MPS VII may also have recurrent ear infections and hearing loss. Affected individuals may have developmental delay and progressive intellectual disability, although intelligence is unaffected in some people with this condition.

In certain embodiments the prophylactic and/or therapeutic methods described herein involve ameliorating one or more of the above symptoms.

Aspartylglucosaminuria.

Aspartylglucosaminuria is a condition that causes a progressive decline in mental functioning. Infants with aspartylglucosaminuria appear healthy at birth, and development is typically normal throughout early childhood. Symptoms of this condition typically present around the age of 2 or 3, and are often characterized by delayed speech. Mild intellectual disability then becomes apparent, and learning occurs at a slowed pace. Intellectual disability progressively worsens in adolescence. Most people with this disorder lose much of the speech they have learned, and affected adults usually have only a few words in their vocabulary. Adults with aspartylglucosaminuria may develop seizures or problems with movement. People with this condition may also have bones that become progressively weak and prone to fracture (osteoporosis), an unusually large range of joint movement (hypermobility), and loose skin.

In certain embodiments the prophylactic and/or therapeutic methods described herein involve ameliorating one or more of the above symptoms (e.g., one or more symptoms selected from the group consisting of delay or loss of speech, cognitive impairment, seizures, locomotor impairment, osteoporosis, and joint hypermobility), and/or delaying the onset, slowing, stopping, or reversing the progression of one or more of these symptoms.

GM1-Glngliosidosis

M1 gangliosidosis is an inherited disorder that progressively destroys nerve cells in the brain and spinal cord. The signs and symptoms of the most severe form of GM1 gangliosidosis, called type I or the infantile form, usually become apparent by the age of 6 months. Infants with this form of the disorder typically appear normal until their development slows and muscles used for movement weaken. Affected infants eventually lose the skills they had previously acquired (developmentally regress) and may develop an exaggerated startle reaction to loud noises. As the disease progresses, children with GM1 gangliosidosis type I can develop an enlarged liver and spleen (hepatosplenomegaly), skeletal abnormalities, seizures, profound intellectual disability, and clouding of the cornea. Loss of vision occurs as the retina gradually deteriorates. An eye abnormality called a cherry-red spot, which can be identified with an eye examination, is characteristic of this disorder. In some cases, affected individuals have an enlarged and weakened heart muscle (cardiomyopathy).

Type II GM1 gangliosidosis consists of intermediate forms of the condition, also known as the late infantile and juvenile forms. Children with GM1 gangliosidosis type II typically show normal early development, but they begin to develop signs and symptoms of the condition around 18 months of age (late infantile form) or 5 years (juvenile form). Individuals with GM1 gangliosidosis type II experience developmental regression but usually do not have cherry-red spots, distinctive facial features, or enlarged organs. Type II usually progresses more slowly than type I, but still causes a shortened life expectancy. People with the late infantile form typically survive into mid-childhood, while those with the juvenile form may live into early adulthood.

Type III of GM1 gangliosidosis is known as the adult or chronic form, and it represents the mildest end of the disease spectrum. The age at which symptoms first appear varies in GM1 gangliosidosis type III, although most affected individuals develop signs and symptoms in their teens. The characteristic features of this type include involuntary tensing of various muscles (dystonia) and abnormalities of the spinal bones (vertebrae).

In certain embodiments the prophylactic and/or therapeutic methods described herein involve ameliorating one or more of the above symptoms (e.g., one or more symptoms selected from the group consisting of cognitive impairment, locomotor impairment, hepatosplenomegaly, skeletal abnormalities, seizures, clouding of the cornea, and loss of vision), and/or delaying the onset, slowing, stopping, or reversing the progression of one or more of these symptoms.

Krabbe Disease (Globoid Cell Leukodystrophy).

Krabbe disease (also called globoid cell leukodystrophy) is a severe neurological condition. It is part of a group of disorders known as leukodystrophies, that result from the loss of myelin (demyelination) in the nervous system. Krabbe disease is also characterized by abnormal cells in the brain called globoid cells, which are large cells that usually have more than one nucleus.

The most common form of Krabbe disease, called the infantile form, usually begins before the age of 1. Initial signs and symptoms typically include irritability, muscle weakness, feeding difficulties, episodes of fever without any sign of infection, stiff posture, and delayed mental and physical development. As the disease progresses, muscles continue to weaken, affecting the infant's ability to move, chew, swallow, and breathe. Affected infants also experience vision loss and seizures. Because of the severity of the condition, individuals with the infantile form of Krabbe disease rarely survive beyond the age of 2. Less commonly, Krabbe disease begins in childhood, adolescence, or adulthood (late-onset forms). Vision problems and walking difficulties are the most common initial symptoms in these forms of the disorder, however, signs and symptoms vary considerably among affected individuals.

In certain embodiments the prophylactic and/or therapeutic methods described herein involve ameliorating one or more of the above symptoms (e.g., one or more symptoms selected from the group consisting of irritability, fevers, limb stiffness, seizures, feeding difficulties, vomiting, and cognitive impairment, locomotor impairment, muscle weakness, spasticity, deafness, optic atrophy, optic nerve enlargement, blindness, paralysis, and difficulty when swallowing), and/or delaying the onset, slowing, stopping, or reversing the progression of one or more of these symptoms.

Metachromatic Leukodystrophy

Metachromatic leukodystrophy is an inherited disorder characterized by the accumulation of fats called sulfatides in cells. This accumulation especially affects cells in the nervous system that produce myelin. Sulfatide accumulation in myelin-producing cells causes progressive destruction of white matter (leukodystrophy) throughout the nervous system, including in the brain and spinal cord (the central nervous system) and the nerves connecting the brain and spinal cord to muscles and sensory cells that detect sensations such as touch, pain, heat, and sound (the peripheral nervous system).

In people with metachromatic leukodystrophy, white matter damage causes progressive deterioration of intellectual functions and motor skills, such as the ability to walk. Affected individuals also develop loss of sensation in the extremities (peripheral neuropathy), incontinence, seizures, paralysis, an inability to speak, blindness, and hearing loss. Eventually they lose awareness of their surroundings and become unresponsive. While neurological problems are the primary feature of metachromatic leukodystrophy, effects of sulfatide accumulation on other organs and tissues have been reported, most often involving the gallbladder.

In certain embodiments the prophylactic and/or therapeutic methods described herein involve ameliorating one or more of the above symptoms (e.g., one or more symptoms selected from the group consisting of leukodystrophy throughout CNS and/or peripheral nervous system, cognitive impairment, loss of sensation in the extremities (peripheral neuropathy), incontinence, seizures, paralysis, an inability to speak, blindness, and hearing loss), and/or delaying the onset, slowing, stopping, or reversing the progression of one or more of these symptoms.

Sandhoff Disease

Sandhoff disease is an inherited disorder that progressively destroys nerve cells (neurons) in the brain and spinal cord. The most common and severe form of Sandhoff disease becomes apparent in infancy. Infants with this disorder typically appear normal until the age of about 3 to 6 months, when their development slows and muscles used for movement weaken. Affected infants lose motor skills such as turning over, sitting, and crawling. As the disease progresses, children with Sandhoff disease experience seizures, vision and hearing loss, intellectual disability, and paralysis. An eye abnormality called a cherry-red spot, which can be identified with an eye examination, is characteristic of this disorder. Some affected children also display organomegaly and/or bone abnormalities.

In certain embodiments the prophylactic and/or therapeutic methods described herein involve ameliorating one or more of the above symptoms (e.g., one or more symptoms selected from the group consisting of cognitive impairment, loss of locomotor function, seizures, hearing loss vision loss, organomegaly, bone abnormalities, and paralysis), and/or delaying the onset, slowing, stopping, or reversing the progression of one or more of these symptoms.

Mucolipidosis Type II (I-Cell Disease)

Mucolipidosis II alpha/beta (also known as I-cell disease) is a progressively debilitating disorder that affects many parts of the body. Most affected individuals do not survive past early childhood.

At birth, children with mucolipidosis II alpha/beta are small and typically have weak muscle tone (hypotonia) and a weak cry. Affected individuals grow slowly after birth and usually stop growing during the second year of life. Development is delayed, particularly the development of speech and motor skills such as sitting and standing.

Children with mucolipidosis II alpha/beta typically have several bone abnormalities, many of which are present at birth. Affected individuals may have an abnormally rounded upper back (kyphosis), feet that are abnormally rotated (clubfeet), dislocated hips, unusually shaped long bones, and short hands and fingers. People with this condition can also have joint deformities (contractures) that significantly affect mobility. Most children with mucolipidosis II alpha/beta do not develop the ability to walk independently. Affected individuals can have dysostosis multiplex. Other features of mucolipidosis II alpha/beta include, but are not limited to heart valve abnormalities, narrowing of the airway which can contribute to prolonged or recurrent respiratory infections, and recurrent ear infections, which can lead to hearing loss.

In certain embodiments the prophylactic and/or therapeutic methods described herein involve ameliorating one or more of the above symptoms (e.g., one or more symptoms selected from the group consisting of cognitive impairment, loss of locomotor function, seizures, hearing loss vision loss, organomegaly, bone abnormalities, and paralysis), and/or delaying the onset, slowing, stopping, or reversing the progression of one or more of these symptoms.

Mucolipidosis Type IIIA (Pseudo-Hurler Polydystrophy)

Pseudo-Hurler polydystrophy (mucolipidosis type III) is a genetic metabolic disorder characterized by a defective enzyme known as UPD-N-acetylglucosamine-1-phosphotransferase. This defective enzyme ultimately results in the accumulation of certain complex carbohydrates (mucopolysaccharides) and fatty substances (mucolipids) in various tissues of the body. The symptoms of this disorder are similar, but less severe than those of I-cell disease (mucolipidosis type II) and may include, but are not limited to, progressive joint stiffness, curvature of the spine (scoliosis), and/or skeletal deformities of the hands (e.g., claw-hands). Growth delays accompanied by deterioration of the hip joints typically develop in children with pseudo-Hurler polydystrophy. Additional symptoms may include clouding of the corneas of the eyes, mild to moderate coarseness of facial features, mild mental retardation, easy fatigability, and/or heart disease.

In most cases, children with pseudo-Hurler polydystrophy do not exhibit symptoms until 2-4 years of age. Specific symptoms and rate of progression may vary from case to case although the disorder is often slowly progressive.

Initial symptoms may include stiffness of the hands and shoulders. In some cases, claw-like deformities of the hands may occur. These symptoms may progress to cause difficulty with specific tasks (e.g., getting dressed). Eventually, carpal tunnel syndrome may develop. Carpal tunnel syndrome is a neurological disorder characterized by compression of the median nerve, which passes through the carpal tunnel inside the wrist (peripheral nerve entrapment). Symptoms of this disorder affect the hand and wrist and may include pain, numbness, loss of feeling in the fingertips, and/or unusual sensation such as burning or "pins and needles."

Additional symptoms associated with pseudo-Hurler polydystrophy may include scoliosis, degeneration of the hip, joints that are permanently fixed in a bent or flexed position (contractures), and short stature. Progressive degeneration of the hip and joint contractures may cause difficulty walking or force affected individuals to walk with a characteristic waddling gait. Affected children may also develop corneal opacity, mild retinopathy, and irregular curvature of the cornea (hyperopic astigmatism). Although many children with pseudo-Hurler polydystrophy have normal intelligence, some may develop mild mental retardation or learning disabilities. In some cases, affected children develop aortic insufficiency.

In certain embodiments the prophylactic and/or therapeutic methods described herein involve ameliorating one or more of the above symptoms (e.g., one or more symptoms selected from the group consisting of selected from the group consisting of joint stiffness, scoliosis, skeletal deformities of the hands (e.g., claw-hands), growth delays, deterioration of the hip joints, clouding of the corneas of the eyes, mild mental retardation, easy fatigability, carpal tunnel syndrome, and heart disease), and/or delaying the onset, slowing, stopping, or reversing the progression of one or more of these symptoms.

Niemann-Pick Disease Type C2 and C1 (NPC1 Mutation)

Niemann-Pick type C has a wide clinical spectrum. Affected individuals may have enlargement of the spleen (splenomegaly) and liver (hepatomegaly), or enlarged spleen or liver combined (hepatosplenomegaly), but this finding may be absent in later onset cases. Prolonged jaundice or elevated bilirubin can present at birth. In some cases, enlargement of the spleen or liver does not occur for months or years, or not at all. Enlargement of the spleen or liver frequently becomes less apparent with time, in contrast to the progression of other lysosomal storage diseases such as Niemann-Pick disease.

Progressive neurological disease is the hallmark of Niemann-Pick type C disease, and is responsible for disability and premature death in most cases beyond early childhood. Classically, children with NPC may initially present with delays in reaching normal developmental milestones skills before manifesting cognitive decline (dementia). Neurological signs and symptoms include cerebellar ataxia (unsteady walking with uncoordinated limb movements), dysarthria (slurred speech), dysphagia (difficulty in swallowing), tremor, epilepsy (both partial and generalized), vertical supranuclear palsy (upgaze palsy, downgaze palsy, saccadic palsy or paralysis), sleep inversion, gelastic cataplexy (sudden loss of muscle tone or drop attacks), dystonia (abnormal movements or postures caused by contraction of agonist and antagonist muscles across joints), most commonly begins with in turning of one foot when walking (action dystonia) and may spread to become generalized, spasticity (velocity dependent increase in muscle tone), hypotonia, ptosis (drooping of the upper eyelid), microcephaly (abnormally small head), psychosis, progressive dementia, progressive hearing loss, bipolar disorder, major and psychotic depression that can include hallucinations, delusions, mutism, or stupor. Typically, in the terminal stages of Niemann-Pick type C disease, the subject is bedridden, with complete ophthalmoplegia, loss of volitional movement and severe dementia.

In certain embodiments the prophylactic and/or therapeutic methods described herein involve ameliorating one or more of the above symptoms (e.g., one or more symptoms selected from the group consisting of splenomegaly, hepatomegaly, hepatosplenomegaly, jaundice, cognitive impairment, cerebellar ataxia (unsteady walking with uncoordinated limb movements), dysarthria (slurred speech), dysphagia (difficulty in swallowing), tremor, epilepsy (both partial and generalized), vertical supranuclear palsy (upgaze palsy, downgaze palsy, saccadic palsy or paralysis), sleep inversion, gelastic cataplexy (sudden loss of muscle tone or drop attacks), dystonia (abnormal movements or postures caused by contraction of agonist and antagonist muscles across joints), spasticity (velocity dependent increase in muscle tone), hypotonia, ptosis (drooping of the upper eyelid), psychosis, progressive dementia, progressive hearing loss, bipolar disorder, major and psychotic depression, loss of volitional movement, and severe dementia), and/or delaying the onset, slowing, stopping, or reversing the progression of one or more of these symptoms.

Danon Disease

Danon disease is a condition typically characterized by cardiomyopathy, weakening of the muscles used for movement, called skeletal muscles (myopathy), and intellectual disability. Signs and symptoms begin in childhood or adolescence in most affected males and in early adulthood in most affected females.

Cardiomyopathy is the most common symptom of Danon disease and occurs in all males with the condition. Most affected men have hypertrophic cardiomyopathy. Other affected males have dilated cardiomyopathy, which is a condition that weakens and enlarges the heart, preventing it from pumping blood efficiently. Some affected men with hypertrophic cardiomyopathy later develop dilated cardiomyopathy. Either type of cardiomyopathy can lead to heart failure and premature death. Most women with Danon disease also develop cardiomyopathy.

Skeletal myopathy occurs in most men with Danon disease and about half of affected women. The weakness typically occurs in the muscles of the upper arms, shoulders, neck, and upper thighs. Many males with Danon disease have elevated levels creatine kinase in their blood, which is often a biomarker that indicates muscle disease.

In certain embodiments the prophylactic and/or therapeutic methods described herein involve ameliorating one or more of the above symptoms (e.g., one or more symptoms selected from the group consisting of cardiomyopathy, skeletal muscle myopathy, and cognitive impairment), and/or delaying the onset, slowing, stopping, or reversing the progression of one or more of these symptoms.

Free Sialic Acid Storage Disorder

Sialic acid storage disease is an inherited disorder that primarily affects the nervous system. People with sialic acid storage disease have signs and symptoms that may vary widely in severity. This disorder is generally classified into one of three forms: infantile free sialic acid storage disease, Salla disease, and intermediate severe Salla disease.

Infantile free sialic acid storage disease (ISSD) is the most severe form of this disorder. Babies with this condition have severe developmental delay, weak muscle tone (hypotonia), and failure to gain weight and grow at the expected rate (failure to thrive). They may have unusual facial features that are often described as "coarse," seizures, bone malformations, an enlarged liver and spleen (hepatosplenomegaly), and an enlarged heart (cardiomegaly). The abdomen may be swollen due to the enlarged organs and an abnormal buildup of fluid in the abdominal cavity (ascites). Affected infants may have a condition called hydrops fetalis in which excess fluid accumulates in the body before birth. Children with this severe form of the condition usually live only into early childhood.

Salla disease is a less severe form of sialic acid storage disease. Babies with Salla disease usually begin exhibiting hypotonia during the first year of life and go on to experience progressive neurological problems. Signs and symptoms of Salla disease include intellectual disability and developmental delay, seizures, problems with movement and balance (ataxia), abnormal tensing of the muscles (spasticity), and involuntary slow, sinuous movements of the limbs (athetosis). Individuals with Salla disease usually survive into adulthood. People with intermediate severe Salla disease have signs and symptoms that fall between those of ISSD and Salla disease in severity.

In certain embodiments the prophylactic and/or therapeutic methods described herein involve ameliorating one or more of the above symptoms (e.g., one or more symptoms selected from the group consisting of cardiomyopathy, skeletal muscle myopathy, and cognitive impairment), and/or delaying the onset, slowing, stopping, or reversing the progression of one or more of these symptoms.

Mucolipidosis IV

Mucolipidosis type IV is an inherited disorder characterized by delayed development and vision impairment that worsens over time. The severe form of the disorder is called typical mucolipidosis type IV, and the mild form is called atypical mucolipidosis type IV.

Approximately 95 percent of individuals with this condition have the severe form. People with typical mucolipidosis type IV typically have delayed development of mental and motor skills (psychomotor delay). Motor skills include sitting, standing, walking, grasping objects, and writing. Psychomotor delay is moderate to severe and usually becomes apparent during the first year of life. Affected individuals have intellectual disability, limited or absent speech, difficulty chewing and swallowing, weak muscle tone (hypotonia) that gradually turns into abnormal muscle stiffness (spasticity), and problems controlling hand movements. Most people with typical mucolipidosis type IV are unable to walk independently. In about 15 percent of affected individuals, the psychomotor problems worsen over time.

Vision may be normal at birth in people with typical mucolipidosis type IV, however, it typically becomes increasingly impaired during the first decade of life. Individuals with this condition typically develop clouding cornea and progressive breakdown of the retina. By their early teens, affected individuals often have severe vision loss or blindness.

People with typical mucolipidosis type IV also typically have impaired production of stomach acid (achlorhydria). Achlorhydria does not cause any symptoms in these individuals, but it does result in unusually high levels of gastrin in the blood. Individuals with mucolipidosis type IV may not have enough iron in their blood, which can lead to anemia. People with the severe form of this disorder usually survive to adulthood, however, they may have a shortened lifespan.

About 5 percent of affected individuals have atypical mucolipidosis type IV. These individuals usually have mild psychomotor delay and may develop the ability to walk. People with atypical mucolipidosis type IV tend to have milder eye abnormalities than those with the severe form of the disorder. Achlorhydria also may be present in mildly affected individuals.

In certain embodiments the prophylactic and/or therapeutic methods described herein involve ameliorating one or more of the above symptoms (e.g., one or more symptoms selected from the group consisting of delayed development, vision impairment, psychomotor delay, cognitive impairment, limited or absent speech, difficulty chewing and swallowing, weak muscle tone (hypotonia), abnormal muscle stiffness (spasticity), locomotor impairment, clouding of the cornea, and impaired production of stomach acid (achlorhydria)), and/or delaying the onset, slowing, stopping, or reversing the progression of one or more of these symptoms.

Multiple Sulfatase Deficiency (MSD).

Multiple sulfatase deficiency is a condition that mainly affects the brain, skin, and skeleton. Because the signs and symptoms of multiple sulfatase deficiency vary widely, the condition has been “split” into three types: neonatal, late-infantile, and juvenile.

The neonatal type is the most severe form, with signs and symptoms appearing soon after birth. Affected individuals typically have deterioration of tissue in the nervous system (leukodystrophy), that can contribute to movement problems, seizures, developmental delay, and slow growth. Skeletal abnormalities can include scoliosis, joint stiffness, and dysostosis multiplex. Affected individuals may also have hearing loss, heart malformations, and an enlarged liver and spleen(hepatosplenomegaly). Many of the signs and symptoms of neonatal multiple sulfatase deficiency worsen over time.

The late-infantile type is the most common form of multiple sulfatase deficiency. It is typically characterized by normal cognitive development in early childhood followed by a progressive loss of mental abilities and movement (psychomotor regression) due to leukodystrophy or other brain abnormalities. Individuals with this form of the condition do not have as many features as those with the neonatal type, but they often have ichthyosis, skeletal abnormalities, and coarse facial features.

The juvenile type is the rarest form of multiple sulfatase deficiency. Signs and symptoms of the juvenile type typically appear in mid- to late childhood. Affected individuals have normal early cognitive development but then experience psychomotor regression, however, the regression in the juvenile type usually occurs at a slower rate than in the late-infantile type. Ichthyosis is also common in the juvenile type of multiple sulfatase deficiency.

Life expectancy is shortened in individuals with all types of multiple sulfatase deficiency. Typically, affected individuals survive only a few years after the signs and symptoms of the condition appear, but life expectancy varies depending on the severity of the condition and how quickly the neurological problems worsen.

In certain embodiments the prophylactic and/or therapeutic methods described herein involve ameliorating one or more of the above symptoms (e.g., one or more symptoms selected from the group consisting of leukodystrophy, scoliosis, hepatosplenomegaly, psychomotor regression), and ichthyosis), and/or delaying the onset, slowing, stopping, or reversing the progression of one or more of these symptoms.

The foregoing lysosomal storage diseases are illustrative and non-limiting. Using the teachings provided herein, one of skill in the art can readily utilize molecular tweezers in the treatment and/or prophylaxis of numerous other LSDs.

Kits.

In various embodiments kit are provided containing materials for practice of the methods described herein. In certain embodiments the kits comprise a container containing one or more molecular tweezers described herein and/or a pharmaceutical formulation comprising one or more molecular tweezers described herein. In certain embodiments the kits can contain a device (e.g., a pre-loaded syringe) for administering the molecular tweezers In certain embodiments the kits optionally include labeling and/or instructional materials providing directions (e.g., protocols) for the use of the molecular tweezers in the treatment or prophylaxis of a lysosomal storage disease, e.g., as described herein. Instructional materials can also include recommended dosages, description(s) of counterindications, and the like.

While the instructional materials in the various kits typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Methods

CLR01 Injection

CLR01 was produced in the facility of Professor Gal Bitan (Associate Professor of Neurology, Department of Neurology, University of California, UCLA). Mice received CLR01 at 1 mg/kg/day until 7 months of age. CLR01 was administered subcutaneously, via osmotic mini-pumps (model 1004). CLR01 dosage has been chosen on the basis of safety and pharmacological characterization of CLR01 in mice (Attar et al. (2014) *BMC Parmacol. & Toxicol* 15: 23).

Brain Collection

After euthanization, mouse brain was collected from each experimental group and perfused with phosphate-buffered saline (PBS pH 7,4) to completely clear blood from tissue. The brains were divided in two equal parts: half of each was frozen in dry ice and used for biochemical analysis. The other halves were fixed in 4% (w/v) paraformaldehyde in PBS and embedded in Optimal cutting temperature compound (OCT compound) or paraffin.

Immunofluorescence and Immunohistochemistry

Medial sagittal sections of frozen brain tissue were cut on a cryostat at either 12 or 40 μm of thickness, permeabilized (PBS, 0.2% Tween□20, and 10% fetal bovine serum), and stained with appropriate primary and secondary antibodies overnight at +40° C. Sections were analyzed by Confocal microscope Zeiss LSM 710 using either 63× or 40× objectives. Stained sections were mounted with Vectashield (Vector Laboratories, CA, USA).

For paraffin embedding, mice brain were fixed in 4% paraformaldehyde (PFA) overnight at 4° C., then mice brain were dehydrated in a graded series of ethanol, cleared with xylene, and infiltrated with paraffin. Paraffin-embedded blocks were cut on a microtome in 6-μm sagittal sections. Immunohistochemistry experiments were 30 performed using the Universal Vectastain Elite ABC HRP Kit (PK6200, Vector Laboratories). For all immunostainings were used sagittal sections, rinsed in PBS1×-Triton 0.1% and treated with 1% $H_2O_2$ for 30 min to quench endogenous peroxidase activity. At this point the sections were exposed at PBS or at Proteinase K digestion (50 μg/ml) for 2 minutes at 37° C. to detect protease resistant structures. After this point the sections were blocked for 1 hour in PBS1×-TritonX-100 0.1%-2% Horse Serum and then incubated with specific antibodies overnight at +40° C., followed by incubation in biotinylated universal antibody (Vector Laboratories) for 90 minutes at room temperature and in ABC reagent (Vector Laboratories) for 45 minutes at room temperature. Sections were dehydrated and then mounted with Leica CV ULTRA (Leica micro systems). Visualization was performed using 3,3-diaminobenzidine tetrahydrochloride (DAB Vector Laboratories). Brightfield images were taken using a Leica DM5000 imaging microscope.

For thioflavin S histochemistry were used cryosections (12 μm), then sections were incubated in 0.1% thioflavin S for 10 min. Slides were immersed to 80% ethanol solution for 5 min, and mounted using FLUORSAVE™ reagent. Positive staining was observed using a Leica DM5500 scan.

Antibodies

Polyclonal rabbit antibody anti-α-synuclein 1:300 (Cat 128 102 SySy), monoclonal rabbit anti-beta Amyloid 1-42 (Aβ1-42) Conformation Specific 1:200 (abcam 201060), polyclonal goat anti-Prion protein PrP 1:200 (abcam 6664), polyclonal goat anti-, monoclonal mouse anti-Tau 1:400 (Cell Signaling #4019), polyclonal rabbit antibody anti-Glial Fibrillary Acidic Protein (GFAP)1:400 (DAKO Z0334), polyclonal rabbit antibody anti-IBA 1 1:200(Synaptic System). ALEXA-FLUOR® secondary antibodies were purchased from Molecular Probe (Invitrogen).

Example 1

Amyloid Protein Aggregation is a Hallmark of Neuropathology in MPS-IIIA Mice MPS-IIIA is caused by deficiency in the lysosomal hydrolase sulfamidase (SGSH) and represents one of the most common and severe forms of LSDs (Valstar et al. (2010) *Ann. Neurol.* 68: 876-887). In MPS-IIIA mice, resulting from a spontaneous missense mutation (D31N) in the catalytic site of the SGSH enzyme, the lysosomal degradation defect leads to progressive lysosomal dysfunction and neurodegeneration, which give rise to the first signs of neurological impairments at around 6 months of age and become more and more severe as the mice age (Bhaumik et al. (1999) *Glycobiology,* 9: 1389-1396; Fraldi et al. (2007) *Hum. Mol. Genet.* 16: 2693-2702; Lau et al. (2008) *Behav. Brain Res.* 191: 130-136). Therefore, MPS-IIIA mice represent an optimal model to study the pathogenic cascade of events underlying neuronal degeneration in LSDs. The inventors have previously found that α-synuclein accumulates at perikarya of neurons in different models of LSDs, including the MPS-IIIA mice contributing to neurodegenerative processes via a loss of function-mediated deregulation of presynaptic activity. In order to further characterize the nature of said α-synuclein aggregates, immunohistochemistry and confocal analyses of Thioflavin S stainings of the brain of MPSIIIA mice at different ages were performed. Thioflavin S is commonly used to detect amyloid deposits in cells and tissues: Thioflavin S is a homogenous mixture of compounds that results from the methylation of dehydrothiotoluidine with sulfonic acid. It is also used to stain amyloid plaques. Thioflavin S binds to amyloid fibrils, giving a distinct increase in fluorescence emission, but not to monomers. Amyloid protein aggregation in MPS-IIIA mice was undetectable at 3 months and became significantly evident in different brain regions starting from 6 months of age (FIG. 1, panels A and B), when first neurodegenerative signs started to appear in this mouse model (Bhaumik et al. (1999) *Glycobiology,* 9: 1389-1396; Sorrentino et al. (2013) *EMBO Mol. Med.* 5: 675-690).

Interestingly, Thioflavin S-positive amyloid deposits appear to be extensively localized to the perinuclear regions of cells, mostly neurons (FIG. 1, panel C). Confocal analysis with different organelle markers demonstrated that such perinuclear amyloid accumulation prevalently occurs in close proximity of the lysosomal compartment, prevalently inside the lysosomal lumen (FIG. 1, panels D, E). Alpha-synuclein immunohistochemistry analysis with proteinase K digestion (amyloid aggregates are highly insoluble and resistant to proteinase K digestion) showed that α-synuclein aggregates in MPSIIIA mouse brain are amyloid-like deposits (FIG. 1, panel C). Supporting this conclusion, confocal analysis showed that α-synuclein staining is mostly thioflavin S-positive (FIG. 1, panel D). Therefore, the present inventors have surprisingly found that MPS-IIIA neurons are characterized by perikarya amyloid depositions and α-synuclein is a component of these deposits.

Example 2

Amyloid Inclusion Composition is Heterogeneous and CNS Region Specific Aggregation Types In order to further characterize amyloid aggregates IHC analysis with proteinase K digestion was performed on several brain regions from MPS IIIA mice at 10 months of age (when neuropathology is fully established) using antibodies against different known aggregate-prone proteins involved in neurodegenerative diseases, namely Tau, prion-protein (PrP), amyloid β peptide (Aβ), TAR DNA-binding protein (TDP)-43, huntingtin and. Moreover, such immunoreactivity was also compared with that resulting from α-synuclein IHC.

Figure 2:
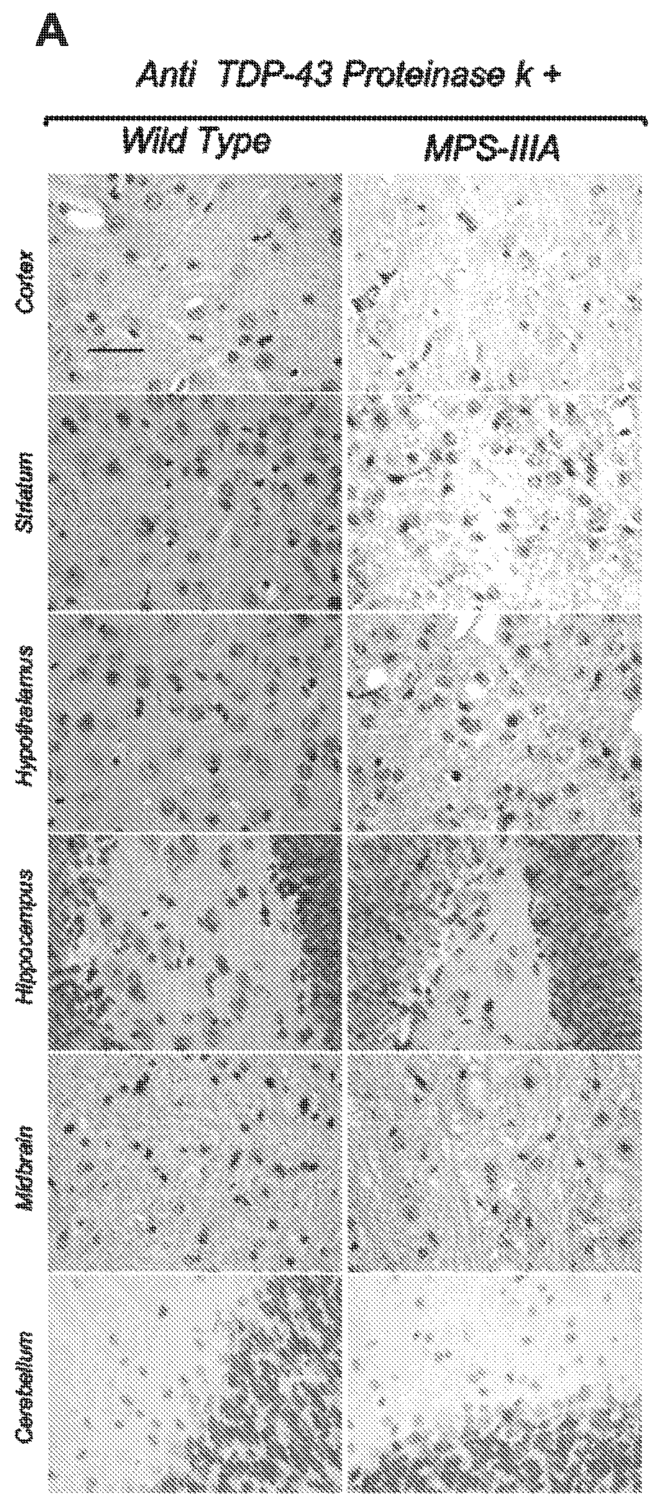
FIG. 2, panels A-E, illustrates the characterization of amyloid aggregates. Sagittal brain sections from control (wild type) and MPS-IIIA mice (10 months-old) have been digested with proteinase K and then exposed using specific antibodies against TAR DNA-binding protein (TDP-43) (Panel A), huntingtin (Panel B), prion-protein (PrP) (Panel C), Tau (Panel D) and Amyloid Beta peptide 1-42 (Aβ1-42) (Panel E). The positive elements in the perikaryon are indicated by arrows while spheroids by arrowheads Representative amyloid inclusions are also showed in enlarged images. Scale bar: 25 μm.

Among aggregate-prone proteins, no immunoreactivity in any brain region was observed for TDP-43 and huntingtin (FIG. 2, panels A, B), whilst all other proteins (Tau, PrP, and Aβ-peptide) showed immunoreactivity. However, such immunoreactivity appeared to be heterogeneous in terms of brain areas analyzed, subcellular localization and shape.

Indeed, while a fraction of such immune-reactivity could be detected as characteristic axonal spheroids or fiber neuritis deposits, a major part was found in the cell body as compact/granular, ring-shaped or tangle-like inclusions extensively localized to perinuclear regions (Table 1).

TABLE 1

Immunoreactivity of aggregate-prone proteins.

| Protein Region | α-Syn | PrP | A β Peptide | Tau | Tdp-43 | Htt |
|---|---|---|---|---|---|---|
| Cortex | Gc = ++<br>Cc = ++ | Gc = ++<br>S = + | Np | Tl = +<br>Cc = + | Np | Np |
| Striatum | Cc = ++<br>S = + | Gc = +<br>S = +++ | S = ++ | Cc = +<br>Rs = ++<br>S = + | Np | Np |
| Hypotalamus | Gc = +<br>Cc = +<br>S = ++ | Gc =<br>S = +++ | S = +++ | Cc = +<br>S = ++ | Np | Np |
| Hippocampus | Np | Np | Np | Np | Np | Np |
| Midbrain | Cc = +<br>Gc = +<br>S = + | Gc = +<br>S = + | S = + | Cc = +<br>Fi = + | Np | Np |

TABLE 1-continued

Immunoreactivity of aggregate-prone proteins.

| Protein Region | α-Syn | PrP | A β Peptide | Tau | Tdp-43 | Htt |
|---|---|---|---|---|---|---|
| Cerebellum | Cc = +<br>Fi = +<br>S = + | Cc = +<br>S = + | S = + | Cc = +<br>Fi = + | Np | Np |

Aggregation types:
Cc = Compact cytoplasmic (cell body, in part perinuclar);
Gc = Granular cytoplasmic (cell body, in part perinuclear);
Rs = Ring shaped (only perinuclear)
S = Spheroids (axonal);
Tl = Tangle like (cell body, in part perinuclear);
Fi = Filamentous Inclusion.
− absent;
+ few,
++ numerous,
+++ abundant
Np = Not Present

Example 3

Amyloid Protein Aggregation is a Hallmark of Lysosomal Storage Disorders

Figure 3:
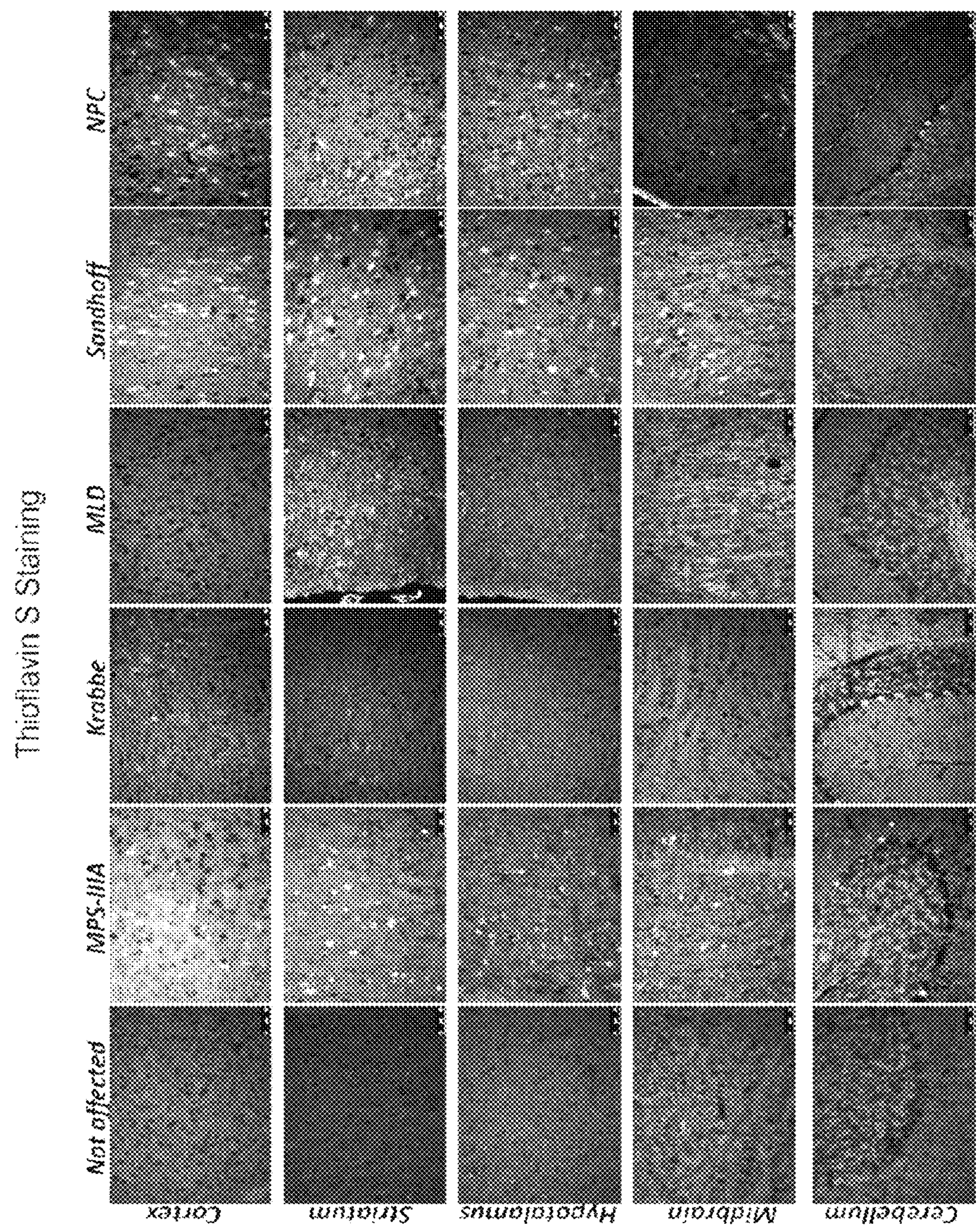
FIG. 3, illustrates amyloid protein aggregation in brain of various LSD mouse models evaluated by Thioflavin S staining.
Figure 4:
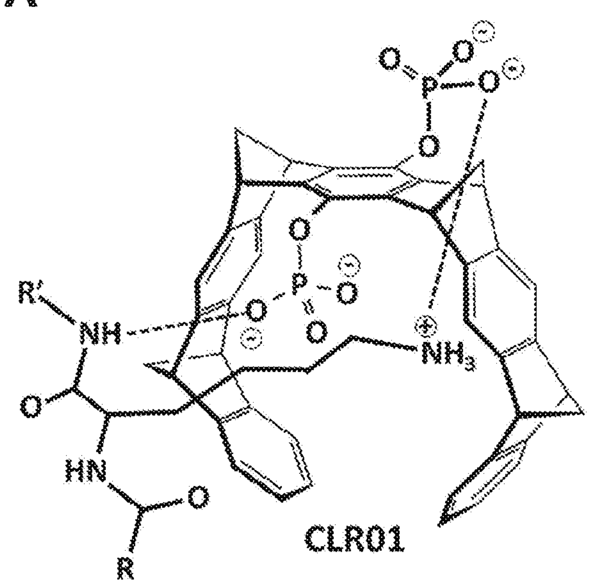
FIG. 4, panels A-C, shows CLR01 structure and amyloid proteins levels in MPSIIIA brain after different treatments with CLR01. Panel A) Schematic drawing of CLR01 molecular tweezers. Mice were treated with 1 mg/kg/day of CLR01 via an osmotic pump. Panel B) Thioflavin S staining on indicated brain sections derived from MPSIIIA mice (7 months of age) treated with CLR01 continuously for either 1 month (treatment started at 6 months of age) or 2 months (treatment started at 5 months of age). Staining of brain sections derived from control either WT or MPS-IIIA mice treated with saline were shown. Nuclei were stained with DAPI. Panel C) Proteinase K treatment on brain section derived from wild type, MPS-IIIA saline injected, and MPS-IIIA injected with CLR01 (only 2 months long treatment is shown). Specific antibodies directed against α-Synuclein, PrP, Aβ1-42 and Tau were used. Nuclei were counterstained with dapi. Scale bar: 20 μm (b); 25 μm (c).

The inventors performed Thioflavin S staining on different areas of the brain of models of several lysosomal storage diseases, and surprisingly found that amyloidogenic aggregates were present, as shown in FIG. 4. Brain cryosections (10 μm of thickness) of wild type, MPS-IIIA and other LSDs mice (Krabbe disease, Metachromatic leucodystrophy, Sandhoff disease, Niemann Pick type C), were stained by Thioflavin S, a specific staining technique used to visualize the amyloid aggregates (see, FIG. 3). After the staining the slices were mounted and the fluorescence was acquired in the FITC filter. Intracellularly located Thioflavin S positive elements were observed in the different brain areas of LSDs animal models as compared to age-matched wild type mice in which only occasionally very few stained elements were noted.

Example 4

CLR01 Administration Inhibits Amyloid Aggregation in MPSIIIA Mouse Brain

Amyloid protein assembly and toxicity may be specifically inhibited by a class of compounds named "molecular tweezers", which act by a process-specific mechanism binding to lysine residues and disrupting molecular interactions that are important for the abnormal self-assembly of multiple amyloidogenic proteins (Sinha et al. (2011) *J. Am. Chem. Soc.* 133: 16958-16969; Attar & Bitan (2014) *Curr. Pharm. Des.* 20: 2469-2483). Among molecular tweezers, CLR01 has been shown to be very effective in protecting against protein aggregation and neurodegeneration in mouse models of synucleinopathies and Alzheimer's disease (Prabhudesai et al. (2012) *Neurotherapeutics,* 9: 464-476; Richter et al. (2017) *Neurotherapeutics,* 14(4): 1107-1119). Remarkably, systemic administration of CLR01 has been shown to have a high safety margin in mice and to allow efficient brain targeting due to the capability of CLR01 to cross the blood-brain barrier (Attar et al. (2012) *Brain,* 135: 3735-3748). The inventors therefore tested whether CLR01 (FIG. 4, panel A), was effective in targeting and destroying amyloid aggregation in MPS IIIA mice. MPSIIIA mice were treated with CLR01 at two different ages, corresponding to two distinct pathological situations; the first group of mice started the treatment at 6 months of age, when amyloid proteins and α-synuclein accumulation is already present ("symptomatic" MPS-IIIA mice) and received the drug continuously over 1 month. The second group of mice started the treatment at 5 months of age, before amyloidogenic protein deposition ("asymptomatic" MPS-IIIA mice), and received the drug continuously over 2 months. Both treatments ended at 7 months of age, when the neuropathological phenotype becomes evident in MPS-IIIA mice (Lau et al. (2008) *Behav. Brain Res.* 191: 130-136; Sambri et al. (2016) *EMBO Mol. Med.* e201606965; Sorrentino et al. (2013) *EMBO Mol. Med.* 5: 675-690; Wilkinson et al. (2012) *PloS one,* 7: e35787). The two different treatment regimens allowed evaluation of the potential therapeutic effect of CLR01 resulting from either prevention or disassembly of amyloid aggregation. Symptomatic MPS-IIIA mice treated with CLR01 showed a partial removal of amyloid deposits, as shown by Thioflavin S staining in different brain regions (FIG. 4, panel B). Asymptomatic MPSIIIA mice treated with CLR01 showed complete disappearance of amyloid proteins (FIG. 4, panel4, panel B) associated with efficient inhibition of the build-up of several amyloid components (FIG. 4*c*). Together, these findings show that CLR01 can clear amyloid aggregation in MPS-IIIA mice Example 5

CLR01 Administration Ameliorated Neuro-Inflammation in MPS-IIIA Mice

Figure 5:
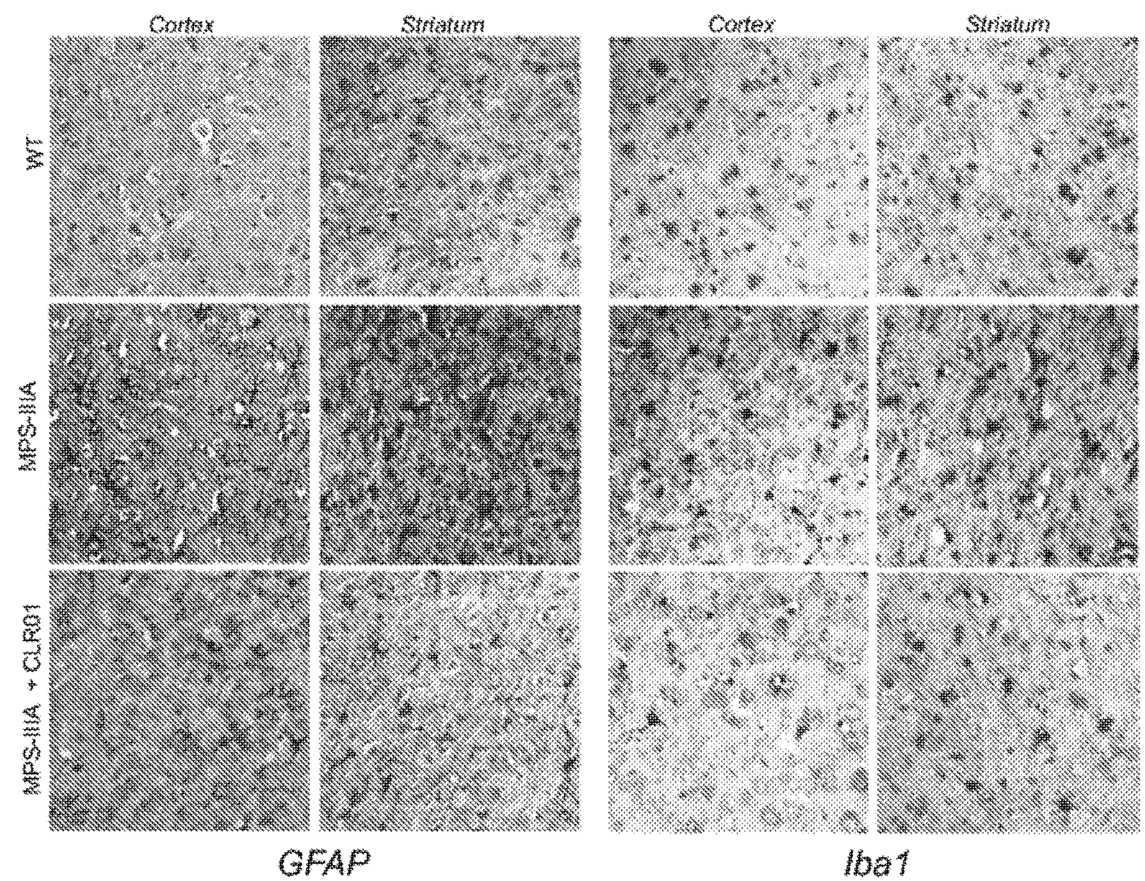
FIG. 5. Panel A) Neuroinflammation in MPSIIIA brain after treatment with CLR01. Confocal analysis of WT and MPSIIIA brain cryosections from the indicated experimental groups of mice were immune-stained with either anti-GFAP or anti-IBA1 (green). DAPI (blue) stains nuclei. Panel B) Quantitation of GFAP and Iba-1 positive cell number (per 0.1 mm2 of tissue) in the cortex and striatum of wild type, MPS-IIIA and MPS-IIIA treated with CLR01. Data are means±s.e.m. **P<0.05, Student's t-test: Either MPS-IIIA 6 months or MPS-IIIA 10 months vs WT; ##P<0.05, Student's t-test: MPSIIIA+2 months CLR01 vs MPSIIIA saline.

To further evaluate the therapeutic effectiveness of the treatment with molecular tweezers described herein, the inventors analyzed neuro-inflammation in MPS-IIIA mice after 2 months of treatment with the compound CLR01, at 7 months of age. Neuroinflammation, is one of the most prominent signs of neuropathology in many neurodegenerative LSDs, including MPS-IIIA, where strong neuroinflammatory markers appear as early as 5-6 months of age (Fraldi et al. (2007) *Hum. Mol. Genet.* 16: 2693-2702; Wilkinson et al. (2012) *PloS one,* 7: e35787). Immunofluorescence staining of neuroinflammatory markers GFAP and IBA1 in CLR01-treated MPS-IIIA mice showed a strong reduction of inflammation (FIG. 5, panels A & B). These results demonstrate that CLR01-mediated inhibition of amyloid aggregation is effective in preventing neurodegenerative signs in MPS-IIIA.

Lysosomal storage diseases (LSDs) are a group of genetic disorders often showing a neurodegenerative course. LSDs are caused by inherited defects of lysosomal function that result in a reduced capability of cells to clear different material, thus leading overtime to a neurodegenerative phenotype. The inventors have herein demonstrated that amyloid deposits progressively build up in the brain of MPS IIIA mice as well as other lysosomal storage disease mice, and that aggregates of amyloid proteins such as α-synuclein, Prion protein, Tau, Aβ, largely co-localize with these deposits. The results shown herein prove that molecular tweezers, that inhibit amyloid aggregation, are effective in preventing relevant neurodegenerative signs such as neuronal degeneration and inflammation in MPS IIIA. This in turn further confirms that amyloid aggregation plays a key role in the onset of neuropathology in MPS IIIA and in other LSDs. The instant examples demonstrate that administration of molecular tweezers according to the invention in a mouse model of MPS IIIA, a severe form of neurodegenerative LSD, can attenuate neuronal loss and reduce inflammation by decreasing amyloid protein aggregation and toxicity. Molecular tweezers thus ameliorate neuropathology in MPS IIIA and are proven to be useful broadly in the treatment of neuropathology in lysosomal storage disorders.

Example 6

Figure 6:
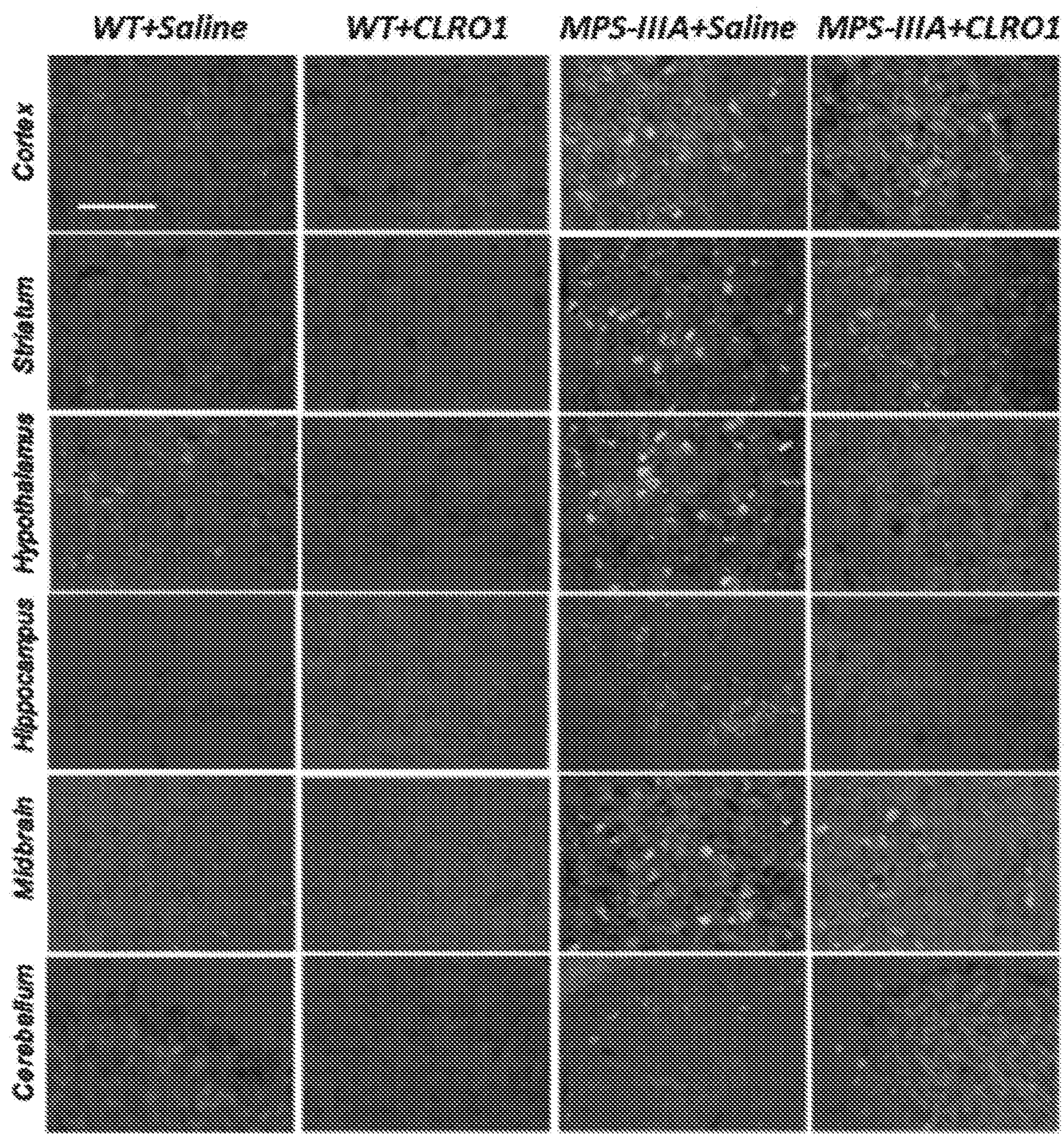
FIG. 6. Panel A) Thioflavin S staining on brain sagittal sections derived from WT saline-injected, WT CLR01-injected, MPS-IIIA-saline injected and MPS-IIIA CLR01-injected mice shows a reduction of amyloid deposition in the brain of CLR01 treated MPS-IIIA mice. Panel B) Immunohistochemistry with Proteinase K treatment on brain sagittal sections from the same groups as panel A measuring α-Synuclein and Tau. A strong reduction in proteinase K-resistant aggregates was found in MPS-MA brain treated with CLR01 compared to control MPS-MA brain (saline-injected).

Inhibiting Amyloid Aggregation Relieves Lysosomal-Autophagic Dysfunction and Protects Against Neurodegeneration in Lysosomal Storage Diseases The potential therapeutic efficacy of CLR01 in MPS-IIIA was further tested by treating MPS-IIIA mice at 4.5 months of age (before massive amyloid aggregation takes place) with daily sub-cutaneous injection of CLR01 over a period of 4.5 months. At the end of treatment (9 months of age) MPSIIIA mice showed an almost complete absence of thioflavin-positive inclusions (FIG. 6, panel A) and, consistently, a striking reduction in the build-up of specific components of amyloid deposits (FIG. 6, panel B).

Figure 7:
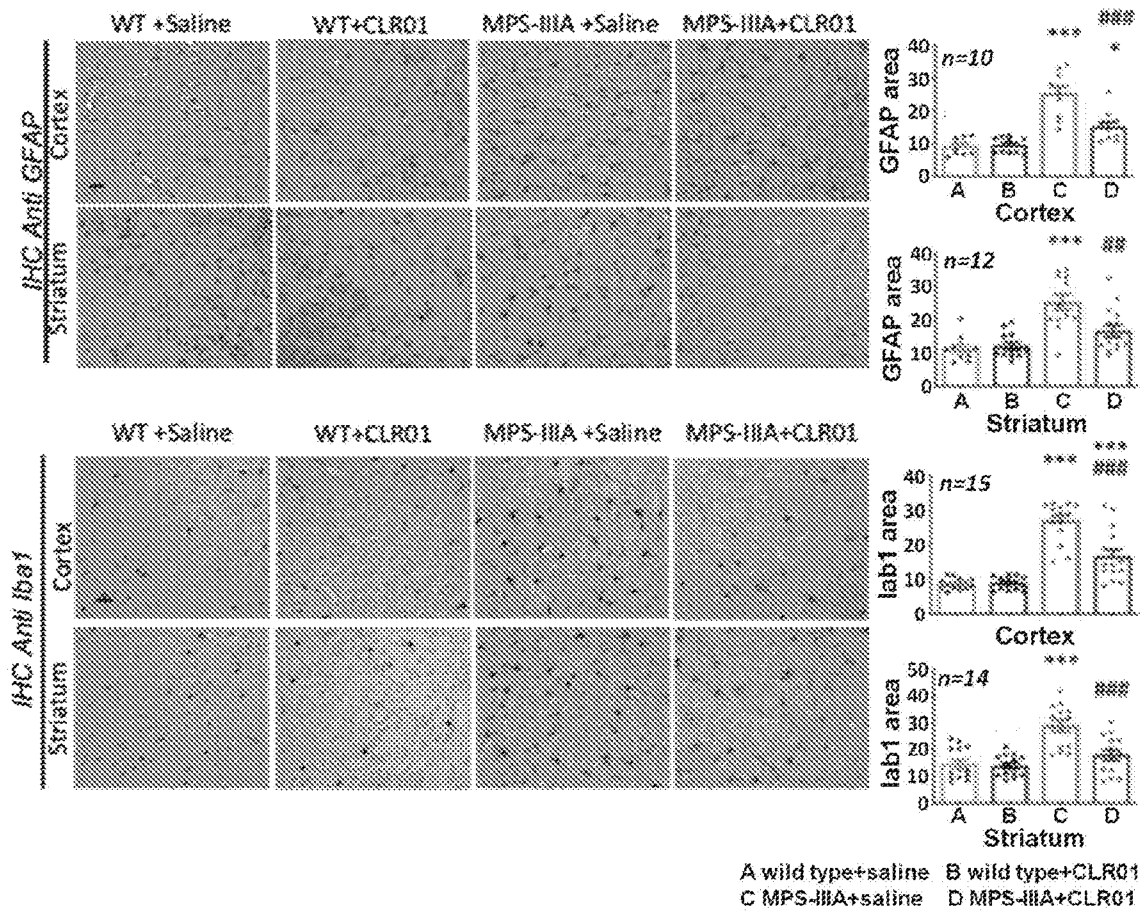
FIG. 7. Panel A) Immunohistochemistry with GFAP and Iba-1 antibodies on brain sagittal sections derived from the four experimental groups of mice. Images of cortex and striatum regions show a reduction in both inflammatory markers in MPS-MA mice upon CLR01 treatment. GFAP and Iba1 immuno-reactivity were quantified in 10-15 different fields taken from the cortical and striatal regions. Three mice for each experimental group were analysed. *p<0.05 vs WT+saline; #p<0.05 vs MPS-MA+saline, One-way ANOVA analysis with Bonferroni's multiple comparison test. Panel B) TEM analysis of synaptic vesicles number. The graphic representation shows the synaptic vesicles/synaptic cleft length ratio for at least 50 synapses derived from 3 mice for each experimental group. The arrows indicate the synaptic cleft. ***p<0.0001 vs WT+Saline; ###p<0.0001 vs MPS-IIIA+saline, One-way ANOVA analysis with Bonferroni's multiple comparison test. Panel C) Contextual fear condition task. Graphical representation of contextual fear conditioning results (freezing time during training and test) shows rescue of memory deficits (reduced freezing time) in MPS-MA mice by CLR01 treatment. 4-10 male mice for each group tested. *p<0.05 vs WT; #p<0.05 vs KO, Duncan post-hoc test.

Progressive neuro-inflammation is one of the most prominent signs of neuropathology in many LSDs, including MPS-IIIA (Attar et al. (2014) *BMC Pharmacol. Toxicol.* 15: 23; Wilkinson et al. (2012) *PloS one* 7: e35787). Consistently, control 9 months-old MPS-IIIA mice displayed a severe neuro-inflammation as showed by GFAP and Iba1 IHC (FIG. 7, panel A). CLR01 treatment strongly reduced neuro-inflammation in MPS-IIIA mice while did not elicit inflammatory response in WT mice (FIG. 7, panel A). Synaptic alterations have been reported in MPS-IIIA mice (Fraldi et al. (2007) *Hum. Mol. Genet.* 16: 2693-2702). Transmission Electron Mycroscopy (TEM) analysis of the synaptic compartment showed that CLR01 treatment was able to rescue synaptic abnormalities in MPS-IIIA mouse brain (FIG. 7, panel B). MPS-IIIA mice display age-dependent activity and anxiety-related behavioral alterations (Lau et al. (2008) *Behav. Brai.n Res.* 191: 130-136). Moreover, recent data showed that MPS-IIIA mice also display a strong impairment in fear contextual conditioning test, a task that is extensively used to test contextual memory functions (D'Amelio et al. (2011) *Nat. Neurosci.* 14: 69-76). Since the outcome of this task is very solid and reliable at 9 months of age, this test was applied to evaluate whether CLR01 administration modifies abnormal behavioral phenotype in MPS-IIIA mice. As expected control 9 months-old MPS-IIIA mice showed a striking memory deficit, which, remarkably, was fully rescued upon CLR01 treatment (FIG. 7, panel C).

Taken together, the present data shows that inhibiting amyloid aggregation in MPS-IIIA mice at an early stage of disease progression significantly reduces neuropathological signs, thus indicating that amyloid deposition contribute to the neurodegenerative processes in a relevant model of neurodegenerative LSD.

At this point the mechanisms underlying amyloid neurotoxicity in MPS-IIIA mice was investigated. In particular, the inventors investigated whether amyloid deposition observed in the context of LSDs might have gain-of-toxic functions effects.

Figure 8:
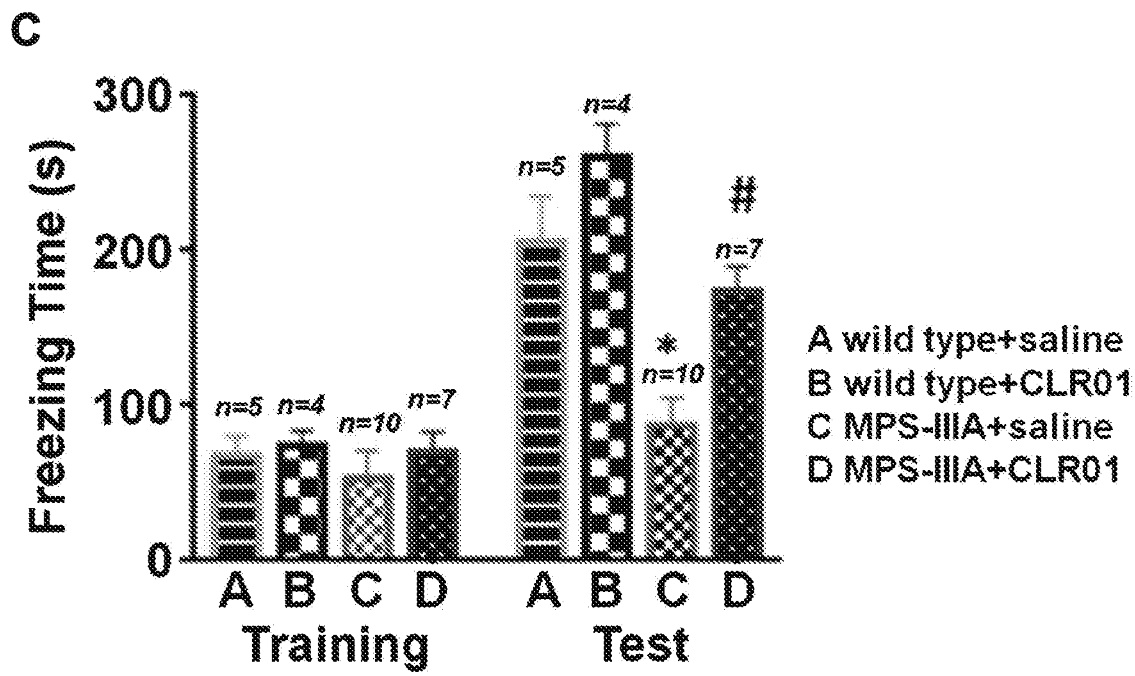
FIG. 8. Panel A) Graphic representation of percentage of Thioflavin S positive staining colocalizing with different organelle markers (Calnexin, GM130, CoxIV, Eaal and Lamp1) in the brain of MPS-IIIA mice (9 months of age). Panel B) Confocal super-resolution images showing the colocalization between the Thioflavin S and Lamp1 in the brain of MPS-IIIA mice (9 months of age). Panel C) IHC anti-Lamp-on brain sagittal sections derived from the four experimental groups of mice (WT saline-injected, WT CLR01-injected, MPS-IIIA-saline injected and MPS-IIIA CLR01-injected). Images from cerebral cortex shown. Lamp 1 immuno-reactivity quantified in 10 different fields from the cortical regions for each group. Three mice for each experimental group. ***p<0.001 vs WT; ###P<0.001 vs MPS-IIIA+saline, One-way ANOVA analysis with Bonferroni's multiple comparison test. Panels D and E) TEM analysis to quantify the number/size of lysosomes in the four experimental group of mice. Three mice for each experiment group. Representative TEM images were shown on the left panel. *, , * p<0.05, 0.01, 0.001 vs WT; ##, ###, P<0.01, 0.001 vs MPS-IIIA+saline, One-way ANOVA analysis with Bonferroni's multiple comparison test.
Figure 8:
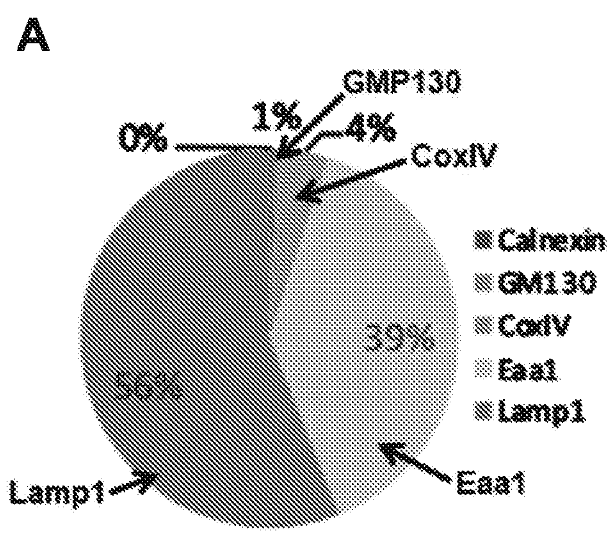

Confocal analysis of Thioflavin S with different organelle markers demonstrated that such perikaryal amyloid accumulation largely occurred in close proximity of the lysosomal compartment, prevalently inside the lysosomal lumen (FIG. 8, panels A, B). Such compartmentalized build-up of amyloids prompted the inventors to evaluate a possible relationship between amyloid accumulation and disturbed the autophagy-Lysosomal Pathway (ALP) in MPS-IIIA. Consistent with the large expansion of lysosomal compartment, a hallmark of LSDs, IHC anti-LAMP1 showed increased signal in MPS-IIIA mouse brain compared to WT (FIG. 8, panel C). CLR01 treatment markedly reduced LAMP1-positive immunostaining in MPS-IIIA brain while did not modify LAMP1 compartment volume in WT mice (FIG. 8, panel C). EM analysis revealed that lysosomal expansion in MPS-IIIA brain reflected an increase in the average lysosomal size, while the total number of lysosomes only slightly increased compared to WT brain (FIG. 8, panel D). However, while in WT brain lysosomes were mostly normal-sized (~400 nm), in MPS-IIIA brain they were predominantly abnormal-sized (>800 nm) (FIG. 8, panel E). CLR01 treatment led to a significant reduction in the average lysosomal size and to a decreased number of abnormal-sized lysosomes (FIG. 8, panel E). Remarkably, the total number of lysosomes in CLR01-treated MPS-IIIA brain remained significantly higher than control MPS-IIIA mice, this reflecting an increase in the number of normal-sized lysosomes vs abnormal-sized lysosomes (FIG. 8, panel E). Consistent with IHC data, CLR01 did not affect lysosome size/number in WT mice FIG. 8, panel E).

Figure 9:
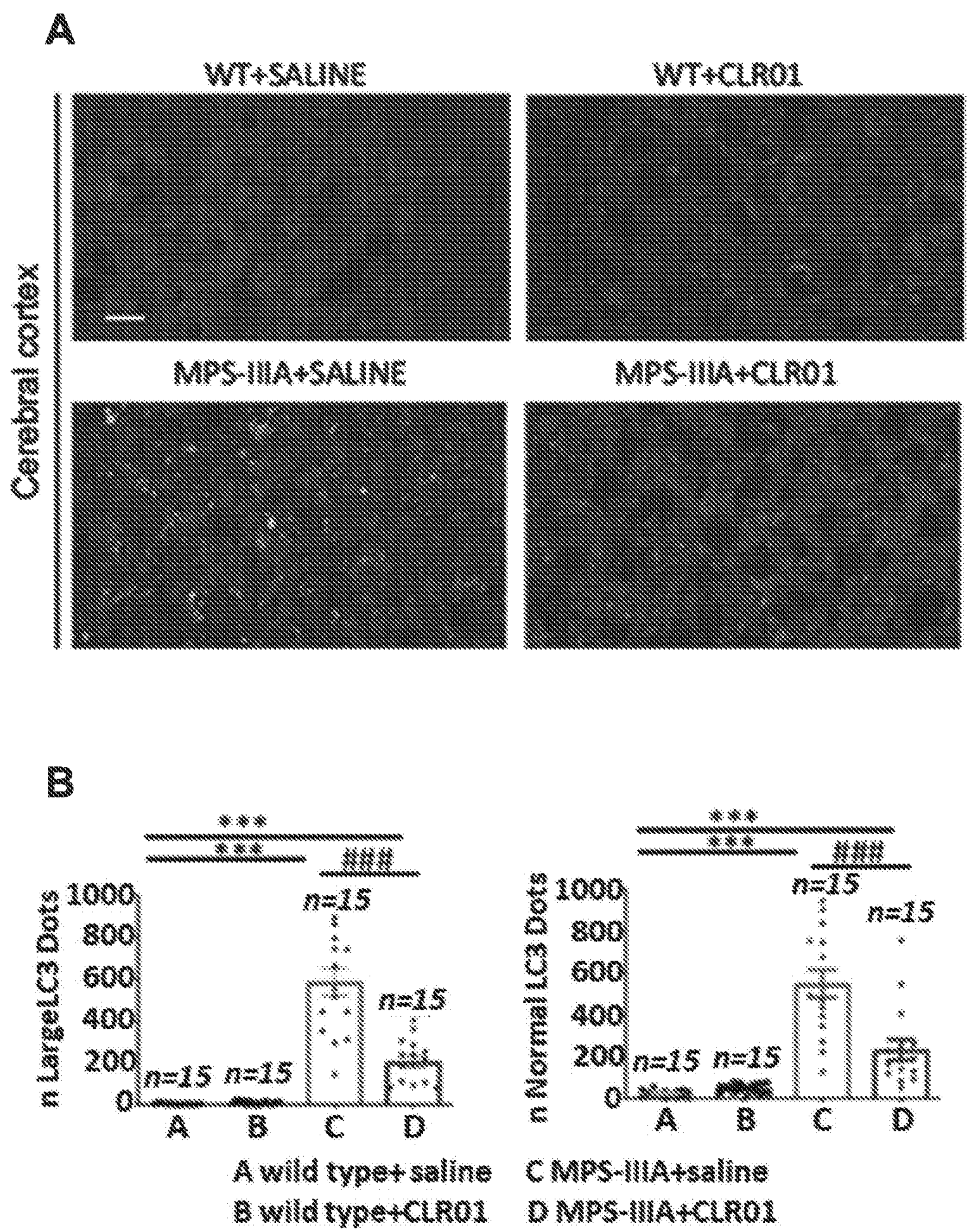
FIG. 9. Panels A and B, show anti-LC3 immunofluorescence on brain sagittal sections from the four experimental groups of mice. The number of LC3-positive dots (either total or large dots) were quantified in 15 different fields from the cortical regions for each group. Three mice for each experimental group. Representative images from cerebral cortex ***p<0.001 vs WT; ###p<vs MPS-IIIA+saline, One-way ANOVA analysis with Bonferroni's multiple comparison test. Panel C) Immunofluorescence analysis of colocalization in MPS-IIIA mice brain sagittal sections between LC3 (green) and Lamp1 (red), LC3 (green) and Neurofilament (red). Panel D) Western Blot analysis of ALP markers LC3-II and p62 reveals a significant increase of both markers in MPS-IIIA+saline respect WT with a reduction in MPS-IIIA+CLR01 values are normalized to β-actin. *, **p<0.05, 0.01 vs WT, One-way ANOVA analysis with Bonferroni's multiple comparison test. Panel E) Immunohistochemistry analysis of anti-Ubiquitin K63 signal on brain sagittal sections derived from the four experimental groups of mice. Images from cerebral cortex shown. UbK63 immuno-reactivity quantified in 10 different fields from the cortical regions from each group. Three mice for each experimental group. *, ***p<0.05, 0.001vs WT; ##p<0.01 vs MPS-IIIA+saline, One-way ANOVA analysis with Bonferroni's multiple comparison test.

To evaluate whether the normalization of the lysosomal compartment mediated by amyloid deposition inhibition was also associated to a functional recovery of lysosomes, the ALP was analyzed in MPS-IIIA mouse brain upon CLR01 treatment. In healthy neurons autophagosomes are efficiently cleared upon axonal retrograde transport and lysosomal encountering and, therefore, are rarely found in neurites or cell bodies unless lysosomal-dependent autophagosome clearance is disrupted (Boland et al. (2008) *J. Neurosci.* 28: 6926-6937; Maday et al. (2012) *J. Cell Biol.* 196: 407-417; Lie & Nixon (2019) *Neurobiol. Dis.* 122: 94-105). Immunofluorescence analysis of LC3 showed a striking increase of LC3-positive puncta in MPS-IIIA brain compared to WT (FIG. 9, panels A, B), thus resembling a block of autophagic flux as expected by previous findings (Settembre et al. (2008) *Hum. Mol. Genet.* 17: 119-129). Consistently, the increase in LC3 dots was mainly due to an accumulation of LAMP1-negative and peripheral/neurites (FIG. 9, panel C), localized large LC3 dots (>0.8 $\mu m^2$), thus suggesting that in MPS-IIIA neurons lysosomes are prevented to encounter autophagosomes, thus hampering their clearance. CLR01 treatment significantly reduced large LC3 dots in MPS-IIIA brain demonstrating that autophagic flux was re-activated by CLR01 treatment (FIG. 9, panel A). However, the number of LC3 dots (both large and normal sized) remained significantly higher compared to WT brain, thus indicating that although autophagosomes are cleared more efficiently, autophagy remained activated in MPS-IIIA brain upon treatment. Importantly, a significant change in LC3 staining was observed in CLR01-treated WT mice (FIG. 9, panel A). the level of lipidated form of LC3 (LC3-II) was also monitored through two different autophagy substrates, p62, and UbK63 (Klionsky et al. (2016) *Autophagy* 12: 1-222). Western blot on brain lysates showed increased levels of LC3-II associated to p62 accumulation in MPS-IIIA brain (FIG. 4*d*). Both LC3-II and p62 protein levels were damped down upon CLR01 treatment (FIG. 9, panels G). Consistently with immufluorescence data, LC3-II levels remained significantly higher than WT (FIG. 9, panel G). Moreover, IHC anti-UbK63 also showed a significant signal reduction in CLR01-treated MPS-IIIA brain compared to control MPS-IIIA brain (FIG. 9, panel E). These results further support the conclusion that the autophagic flux is reactivated in MPS-IIIA brain upon CLR01 treatment.

Data disclosed herein show that CLR01 was able to relief autophagy block in MPS-IIIA brain. Such effect was mediated by the inhibition of amyloid deposition since no significant change in lysosomal autophagic axis was observed in WT mice upon CRL01 treatment, thus ruling out a direct effect of CRL01 on the autophagy-Lysosomal Pathway (ALP). Therefore, the present data support a model in which progressive amyloid build-up into lysosomes impairs autophagic flux. Mechanisms underlying such effect involve the negative impact of amyloids on autophagosome clearance through the prevention of lysosome encountering. A possibility might be that amyloid interferes with lysosomal positioning, a process that has been shown to be critical for efficient autophagosome clearance in neurons (Pu et al. (2016) *J. Cell Sci.* 129: 4329-4339). The finding that CLR01-mediated inhibition of lysosomal amyloid deposition in MPS-IIIA was also associated to an increased number of lysosomes/autophagosomes indicates that ALP is somehow induced in such context. This might be a consequence of the relief of the autophagy block and/or might be a result of a more specific effect of CLR01 on lysosomal-mediated signaling pathways inducing ALP, signaling that may be impaired by amyloid deposition in MPS-IIIA.

Without being bound to a particular theory, it is believed that primary lysosomal storage induces amyloid protein deposition. Supporting this hypothesis it has been reported that GAGs provide a scaffold promoting amyloid aggregation (Iannuzzi et al. (2015) *Molecules,* 20: 2510-2528). Moreover, it is also likely that autophagy block might, in turn, boost amyloid build-up, thus generating a vicious circle, that can be interrupted by CLR01 treatment.

In conclusion, the present findings demonstrate that amyloid aggregation plays a key role in the onset of neuropathology in MPS-IIIA and likely in other LSDs thus, identifying LSDs as new class of amyloid disorders. Data herein also show that the molecular tweezers, namely CLR01, are a particularly attractive compound in the treatment of neuropathology in these disorders. Moreover, the recovery of efficient lysosomal-mediated autophagosome clearance represents a critical mechanism mediating CLR01 therapeutic effectiveness, thus putting more insights into the processes mediating gain of toxic function of amyloid deposition and providing new evidence linking common neurodegenerative diseases to LSDs.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a lysosomal storage disease in a mammal, said method comprising:

administering to said mammal an effective amount of a molecular tweezers that is capable of inhibiting protein aggregation, wherein said effective amount is an amount effective to slow the progression, or stop, or reverse protein accumulation/aggregation associated with said lysosomal storage disease, and/or said effective amount is an amount effective to ameliorate one or more symptoms of the pathology associated with said lysosomal storage disease and/or to reduce neurodegeneration and/or neuro-inflammation associated with said lysosomal storage disease;

wherein said lysosomal storage disease is Sanfilippo syndrome, and said method is effective to reactivate autophagic flux in the neurons of the mammal.

2. The method of claim 1, wherein said effective amount is an amount effective to delay the onset, or to slow, or to stop, or to reverse progression of a pathology associated with said lysosomal storage disease.

3. The method of claim 1, wherein said administration is before appearance of symptoms in said mammal and said mammal is identified as having the lysosomal storage disease by the presence of a genetic marker for said lysosomal storage disease.

4. The method of claim 1, wherein said amelioration of one or more symptoms comprises a reduction of neuroinflammation and/or slowing, stopping, or reversing progression of neuro-inflammation.

5. The method of claim 4, wherein a reduction of neuroinflammation and/or slowing, stopping, or reversing progression of neuro-inflammation is characterized by a reduction in one or more markers of neuroinflammation, wherein said marker(s) of neuroinflammation are selected from the group consisting of Iba1 (marker of microglial activation), GFAP (marker for astrocytic response), TNF-alpha, interleukins, and TGF-beta.

6. The method of claim 1, wherein said method is effective to slow, or to stop, or to reverse neuronal loss (neurodegeneration) in said mammal.

7. The method of claim 1, wherein said method is effective to reduce memory deficit, and/or to reduce abnormal lysosome size and/or number of abnormal sized lysosomes in said mammal.

8. The method of claim 1, wherein said molecular tweezers is a molecular tweezers according to any one of formulas I to IV:

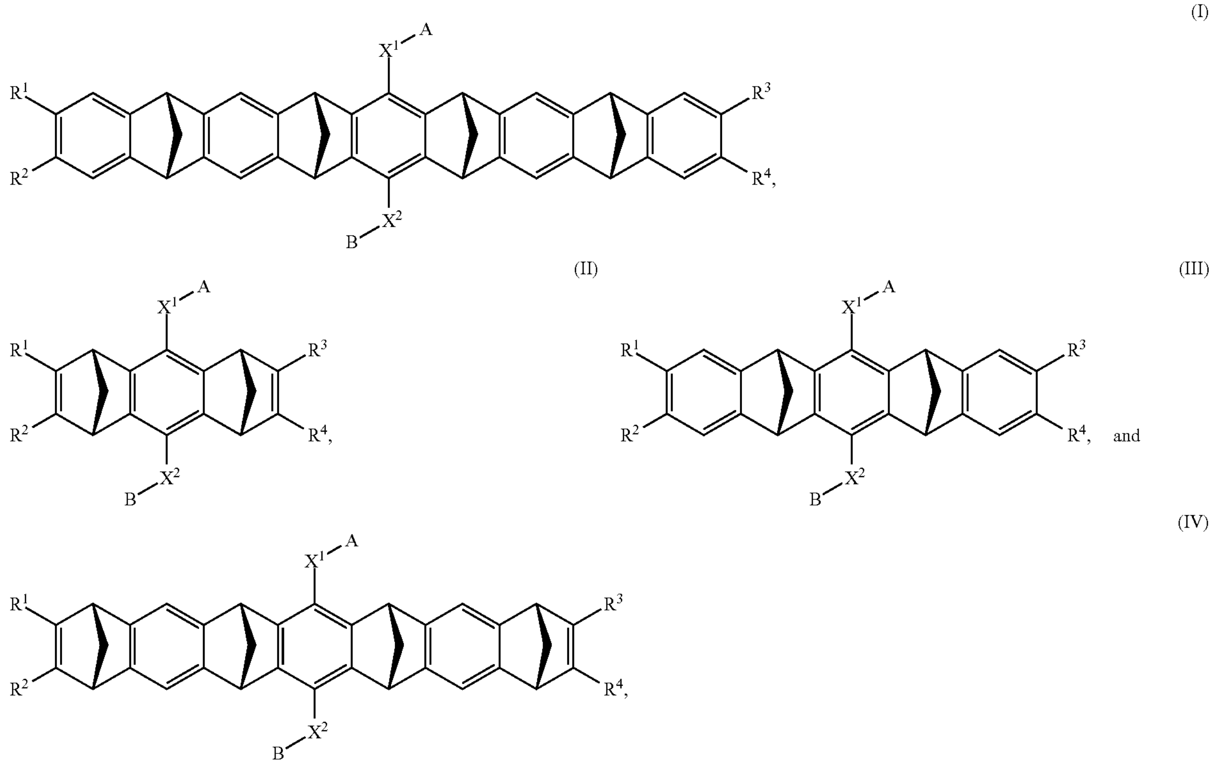

or a pharmaceutically acceptable salt, ester, amide, or prodrug thereof, wherein:

$X^1$ and $X^2$ are both O;

A alone, or A combined with $X^1$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate, and

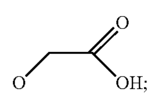

B alone, or B combined with $X^2$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate and

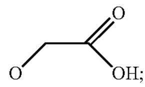

and each of $R^1$, $R^2$, $R^3$, and $R^4$ is, independently, selected from the group consisting of H, Cl, Br, I, OR, $NR_2$, $NO_2$, $CO_2H$, and $CO_2R^5$, wherein $R^5$ is alkyl, aryl or H, or $R^1$ and $R^2$ combine to form an aliphatic or aromatic ring, and/or $R^3$ and $R^4$ combine to form an aliphatic or aromatic ring.

9. The method of claim 8, wherein A and B are independently selected from the group consisting of

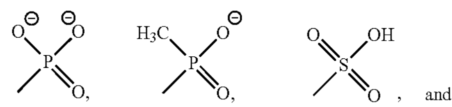

-continued

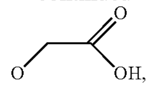

wherein A and B are optionally the same.

10. The method of claim 8, wherein A and B are independently selected from the group consisting of

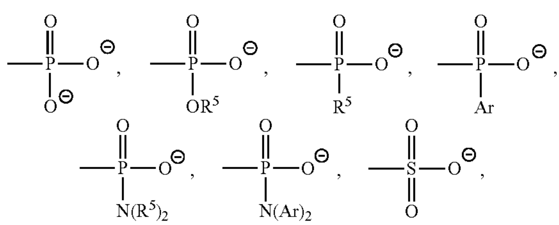

and —$(CH_2)_n$—$CO_2^-$, where $R^5$ is alkyl or H; n ranges from 1 to 10, and Ar is aryl, where A and B are optionally the same.

11. The method of claim 8, wherein said molecular comprises a compound according to a formula selected from the group consisting of:

(TW1/CLR01)

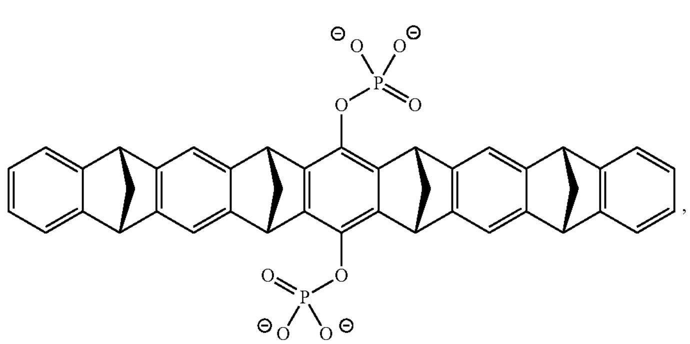

(TW2)

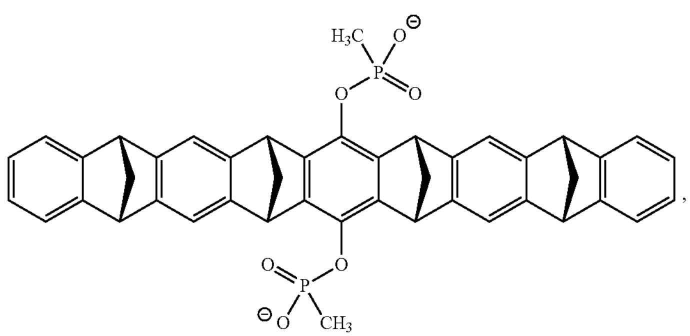

(TW4)

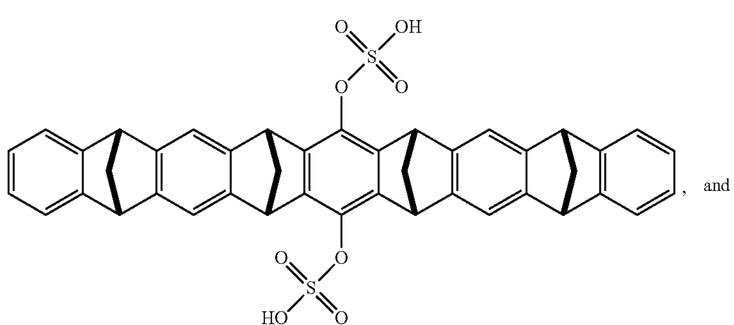

-continued
(TW5)
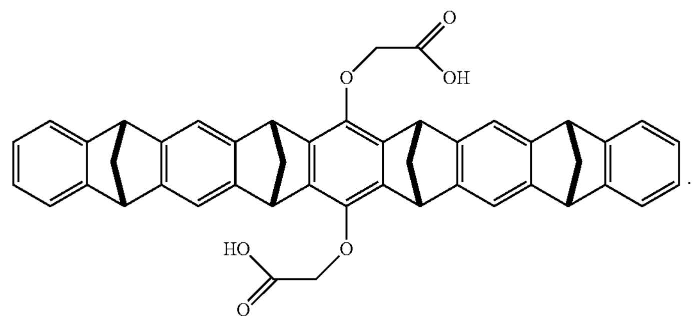
12. The method of claim 1, wherein said method is effective to rescue a memory deficit in said mammal.
* * * * *